United States Patent
Yasri et al.

(10) Patent No.: US 8,580,815 B2
(45) Date of Patent: Nov. 12, 2013

(54) DERIVATIVES OF AZAINDOLES AS INHIBITORS OF PROTEIN KINASES ABL AND SRC

(75) Inventors: Abdelaziz Yasri, Castelnau le Lez (FR); Gwénaël Cheve, Saturargues (FR); Cédric Bories, Montpellier (FR); Louis Delon, Montpellier (FR)

(73) Assignee: Oribase Pharma, Montpellier (FR)

( * ) Notice: Subject to any disclaimer, the term of this patent is extended or adjusted under 35 U.S.C. 154(b) by 0 days.

(21) Appl. No.: 13/148,988

(22) PCT Filed: Feb. 12, 2010

(86) PCT No.: PCT/IB2010/000593
§ 371 (c)(1), (2), (4) Date: Aug. 11, 2011

(87) PCT Pub. No.: WO2010/092489
PCT Pub. Date: Aug. 19, 2010

(65) Prior Publication Data
US 2011/0312959 A1    Dec. 22, 2011

Related U.S. Application Data

(60) Provisional application No. 61/202,279, filed on Feb. 12, 2009.

(30) Foreign Application Priority Data

Feb. 12, 2009 (FR) .................................... 09 00631

(51) Int. Cl.
*A61K 31/437* (2006.01)
*C07D 471/04* (2006.01)

(52) U.S. Cl.
USPC .......................................... 514/300; 546/113

(58) Field of Classification Search
USPC .......................................... 546/113; 514/300
See application file for complete search history.

(56) References Cited

U.S. PATENT DOCUMENTS

| 7,361,763 B2 | 4/2008 | Arnold et al. |
| 7,361,764 B2 | 4/2008 | Arnold et al. |
| 7,582,637 B2 | 9/2009 | Arnold et al. |
| 7,601,839 B2 | 10/2009 | Arnold et al. |
| 7,709,645 B2 | 5/2010 | Arnold et al. |
| 7,728,140 B2 * | 6/2010 | Salom et al. ............ 546/113 |
| 7,888,508 B2 | 2/2011 | Salom et al. |
| 7,906,648 B2 | 3/2011 | Arnold et al. |
| 2006/0217369 A1 * | 9/2006 | Gavai et al. ............ 514/217.06 |
| 2009/0318428 A1 | 12/2009 | Honold et al. |
| 2011/0136857 A1 | 6/2011 | Salom et al. |

FOREIGN PATENT DOCUMENTS

| WO | WO2005063746 | * 7/2005 |
| WO | WO 2008/144253 | 11/2008 |
| WO | WO2010/062171 | 6/2010 |

OTHER PUBLICATIONS

Patani et. al., "Bioisosterism: A Rational Approach in Drug Design", Chem. Rev. 1996, 96, 3147-3176.*
Freshney ( Culture of Animal Cells, A Manual of Basic Technique, Alan R. Liss, Inc., 1983, New York, p4).*
Dermer (Bio/Technology, 1994, 12:320).*
International Search Report for PCT/IB2010/000593.
U.S. Appl. No. 61/110,765, filed Nov. 3, 2008, Beusker.
U.S. Appl. No. 61/140,213, filed Dec. 23, 2008, Beusker.
European Search Report dated Jun. 26, 2012 in corresponding EP10710439.0.

* cited by examiner

*Primary Examiner* — Rita Desai
(74) *Attorney, Agent, or Firm* — B. Aaron Schulman; Stites & Harbison, PLLC

(57) ABSTRACT

The present invention relates to compounds of general formula I and use thereof as inhibitors of protein kinases Abl and Src and the method of production thereof. The present invention also relates to pharmaceutical compositions and medicinal products comprising these compounds.

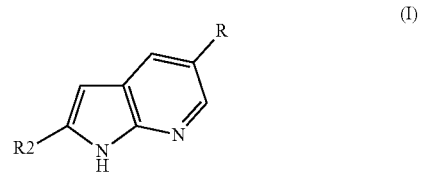

(I)

10 Claims, 6 Drawing Sheets

DERIVATIVES OF AZAINDOLES AS INHIBITORS OF PROTEIN KINASES ABL AND SRC

CROSS REFERENCE TO RELATED APPLICATIONS

This is a §371 National Stage of International Application No. PCT/IB2010/000593 filed Feb. 12, 2010 (which is hereby incorporated by reference), which claims benefit of U.S. Provisional Application No. 61/202,279, filed Feb. 12, 2009 (which is hereby incorporated by reference).

The present invention relates to compounds that are inhibitors of protein kinases, the method of preparation thereof and the therapeutic application thereof.

Dysfunction of protein kinases (PK) is the cause of a large number of pathologies. In fact, a high proportion of the oncogenes and proto-oncogenes involved in human cancers code for PK.

It has also been discovered that increased activity of the PK is involved in many non-malignant diseases such as benign prostatic hyperplasia, familial adenomatosis, polyposis, neuro-fibromatosis, psoriasis, proliferation of smooth cells of blood vessels associated with atherosclerosis, pulmonary fibrosis, glomerulonephritis and stenoses and post-operative restenoses.

The PK are involved in the inflammatory response and the multiplication of viruses and parasites. The PK are also known to have a major role in the pathogenesis and development of neurodegenerative disorders.

Chronic myeloid leukaemia (CML) is due to the malignant transformation of a haematopoietic stem cell characterized by an acquired genetic abnormality: the oncogene BCR-ABL, produced by the chromosome Philadelphia (Ph) 22q (Deininger et al., *Blood*, 2000, 96, 3343-3356). This fusion gene codes for a chimeric protein Bcr-AbI displaying constitutively activated tyrosine kinase AbI activity.

Expression of a Bcr-AbI fusion protein arising from a different translocation of the BCR gene is also the cause of Ph-positive acute lymphoblastic leukaemia (ALL Ph+), for Philadelphia-chromosome positive (Chan et al., *Nature*, 1987, 325, 635-637; Melo et al., *Leukemia*, 1994, 8, 208-211; Ravandi et al., *Br. J. Haematol.*, 1999, 107, 581-586). CML represents about 15 to 20% of leukaemias in adults. This disease, characterized by excessive proliferation of the cells of the myeloid line, is regarded by many specialists as a reference model for understanding the mechanisms of proliferation of haematopoietic stem cells, as well as for the development of new medicinal products against cancers.

One of the first inhibitors discovered to be active against kinase AbI is Imatinib (Gleevec/Glivec, STI-571; Novartis Pharma AG), a molecule of the phenylaminopyrimidine type. Imatinib was developed for the therapeutic treatment of cancers (Druker et al., *Nat. Med.*, 1996, 2, 561-566). Druker demonstrated selective inhibition of the kinase AbI by Imatinib with an $IC_{50}$ between 0.038 and 0.025 µM.

It was demonstrated that this molecule not only inhibits the kinase AbI, but also plays the role of inhibitor of c-KIT, PDGFR (platelet-derived growth factor receptor) or also of other proteins (Bantscheff et al., *Nat. Biotechnol.*, 2007, 25, 1035-1044; Okuda et al., *Blood*, 2001, 97, 2440-2448; Dewar et al., *Blood*, 2005, 105, 3127-3332). Clinical trials have shown that Imatinib induces rapid remission in patients in the chronic phase, expressing the Bcr-AbI fusion protein, while displaying negligible toxicity (O'Brien et al., *N. Engl. J. Med*, 2003, 384, 994-1004; Apperley et al., *N. Engl. J. Med*, 2002, 347, 471-487).

Imatinib has also been tested successfully in phase II clinical trials on gastrointestinal stromal tumours (GIST) expressing KIT and PDGFRα and has shown promising efficacy on a certain number of diseases in which deregulation of the kinase activity of PDGFR has been demonstrated including a dermatofibrosarcoma, a hypereosinophilic syndrome and chronic myelomonocytic leukaemia; (Rubin et al., *J. Clin. Oncol*, 2002, 20, 3586-3591; Maki et al., *Int. J. Cancer*, 2002, 100, 623-626[2]; Apperley et al., *N. Engl. J. Med*, 2002, 347, 471-487; Gotlib et al., *Blood*, 2004, 103, 2879-2891).

However, some patients with CML or ALL Ph+ at an advanced stage develop resistance to Imatinib, generally reflected in the appearance of mutations at the catalytic site or in the regions near Bcr-AbI or in amplification of the BCR-ABL gene (Gorre et al., *Science*, 2001, 293, 876-80; Le Coutre et al., *Blood*, 2000, 95, 1758-66; Weisberg et al., *Blood*, 2000, 95, 3498-505; Mahon et al., 2000, *Blood*, 96, 1070-9; Campbell et al., *Cancer Genet Cytogenet*, 2002, 139, 30-3; Hochhaus et al., *Leukemia*, 2002, 16, 2190-6).

The protein kinases of the Src family are involved in leukaemias mediated by Bcr-AbI and have been implicated in several cases of resistance to Imatinib. In this connection, several Src/AbI inhibitors have been developed, such as 4-anilo-3-quinolinecarbonitrile, 2,6,9 trisubstituted purine analogues, and pyrido[2,3-d]pyrimidines, to offer alternative treatments for patients with Chronic Myeloid Leukaemia or Acute Lymphoblastic Leukaemia (Martinelli et al., *Leukemia*, 2005, 19, 1872-1879).

The kinases of the Src family also regulate key routes of metastatic progression of malignant tumours including adhesion, invasion, cellular motility and angiogenesis (Brunton et al., *Curr Opin Pharmacol.*, 2008, 8, 427-432). Overexpression of the protein c-Src as well as increase in its activity were observed in several types of cancers including colorectal cancer, various gastrointestinal cancers (hepatic, pancreatic, gastric and oesophageal) as well as breast, ovarian and lung cancers (Yeatman et al., *Nat Rev Cancer*, 2004, 4, 470-80).

Moreover, crystallographic studies have revealed that Imatinib binds to the kinase domain of AbI only when the latter assumes an inactive conformation (Nagar et al., *Cancer Res*, 2002, 62, 4236-43; Schindler et al., *Science*, 2000, 289, 1938-42). These results were at the origin of the development of alternative therapies in order to overcome resistance to Imatinib but also at the origin of the design of new molecules capable of binding specifically to the kinase domain of AbI in active conformation (Cowan-Jacob et al., *Acta Crystallogr D Biol Crystallogr*, 2007, 63, 80-93; Weisberg et al., *Nat Rev Cancer*, 2007, 7, 345-56). The classes of new inhibitors developed include selective inhibitors of AbI, inhibitors of the AbI kinases and of the kinases of the Src family, inhibitors of Aurora kinases and inhibitors of Bcr-AbI non-competitive for ATP.

Among the new classes of inhibitors we may mention (Weisberg et al., *Nat Rev Cancer*, 2007, 7, 345-56): Nilotinib which mainly inhibits AbI as well as KIT and PDGFRβ, Dasatinib which inhibits kinases of the Src family as well as KIT, Bcr-AbI, PDGFR, Bosutinib which inhibits kinases of the Src family and Bcr-AbI and Dasatinib which attaches, in contrast to the other inhibitors, on the active conformation of the AbI kinase domain. However, side effects are observed with Dasatinib, of fluid retention (including pleural effusion), diarrhoea, etc.

However, as suggested by Weisberg et al. (Weisberg et al., *Nat Rev Cancer*, 2007, 7, 345-56), it can be assumed, as for Imatinib, Nilotinib or some other inhibitors of kinases, that some patients may develop resistance to the new classes of inhibitors. It is therefore necessary to find new molecules that are inhibitors of protein kinases.

The object of the present invention is to offer novel inhibitors of kinases, having an original backbone, which can be used therapeutically in the treatment of pathologies associated with deregulation of protein kinases.

The inhibitors of the present invention can be used for the treatment of numerous cancers and more particularly in the case of chronic or acute myeloproliferative disorders such as certain leukaemias and in the case of colorectal cancer, various gastrointestinal cancers (hepatic, pancreatic, gastric and oesophageal), as well as breast, ovarian and lung cancers.

Another object of the invention is to offer novel selective inhibitors of the kinases Abl and Src.

Yet another objective of the invention is to offer a method of preparation of said inhibitors.

The present invention relates to compounds of general formula I:

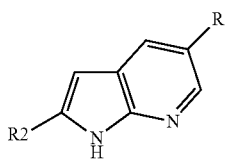

Formula I in which R represents:
  a group NHCOR$^1$, or
  a group NR$^3$R$^4$
  where
R$^1$ represents:
  an aryl, preferably phenyl, group optionally mono- or polysubstituted with:
    a halogen atom, preferably bromine, fluorine, chlorine, or iodine
    a nitro group,
    a cyano group,
    a methylthiazyl group,
    an alkoxy, preferably methoxy, group,
    a trifluoroalkoxy, preferably trifluoromethoxy, group,
    an aryloxy, preferably phenyloxy, group,
    a trifluoroalkyl, preferably trifluoromethyl, group,
    a substituted or unsubstituted sulphonamide group, preferably N-methyl sulphonamide,
    a heteroaryl, preferably pyridazyl group, or pyridazinyl group optionally mono- or poly-substituted with a halogen atom, preferably chlorine,
    a linear or branched C1-C6 alkyl group, preferably methyl, or a group selected from the groups A, B, C, D or E as defined below:

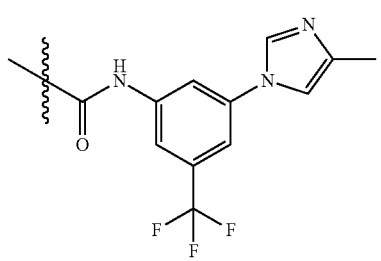

A

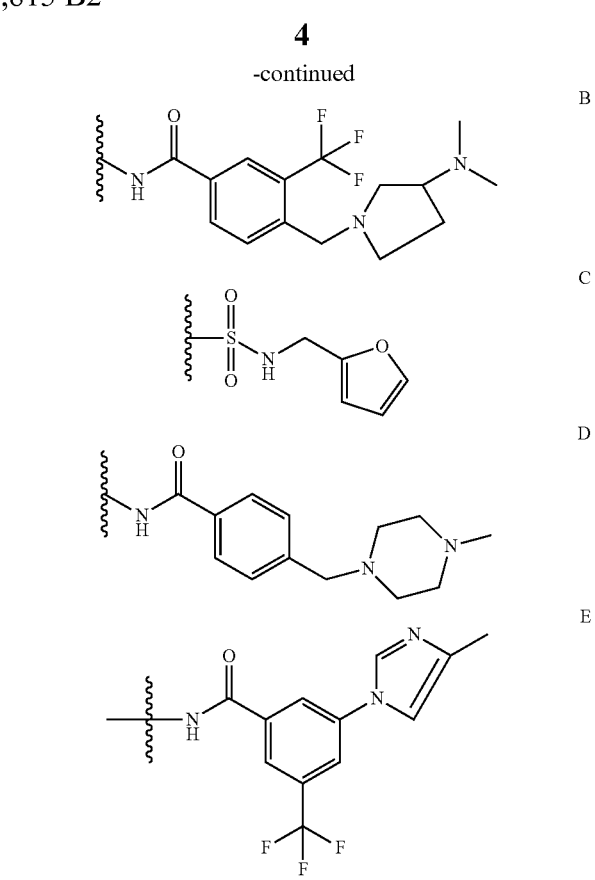

a heteroaryl group, preferably
  a pyridyl group optionally mono- or poly-substituted with
    a sulphanyl, preferably propylsulphanyl, group,
  a thiophenyl group,
  a thiazyl group,
  an imidazyl group,
  a pyrazyl group optionally mono- or polysubstituted with
    an alkyl group, preferably methyl,
  a quinoxaline group,
  a dihydrobenzofuranyl group, or
  an indyl group,
  a cycloalkyl group, preferably cyclopropyl,
  a linear or branched C$_1$-C$_6$ alkyl group, preferably ethyl, isopropyl, or
  a C$_1$-C$_6$ aralkyl group, preferably phenylalkyl, preferably phenylmethyl, optionally mono- or poly-substituted with an alkoxy group, preferably methoxy, and/or a halogen atom, preferably bromine.
R$^2$ represents:
  an ester group COOR$^{14}$,
  an alkyl group CH$_2$R$^9$, CH$_2$OCOR$^{10}$, CH$_2$NR$^{11}$R$^{12}$,
  an amide group CONR$^7$R$^8$, or
  a group COR$^{13}$,
R$^7$ and R$^8$, which may be identical or different, represent:
  a hydrogen atom,
  a C$_1$-C$_6$ aminoalkyl group, preferably N,N-dimethylaminopropyl, or
  a C$_1$-C$_6$ morpholinoalkyl group, preferably N-morpholinoethyl,
R$^9$ represents:
  a heteroaryl group, preferably imidazyl or pyrryl,
  a heterocyclic group, preferably N-morpholinyl or tetrahydrofuranyl, an alkoxy group, preferably methoxy, or
a hydroxyl group, $R^{10}$ represents:
a heteroaryl group, preferably quinoxaline, $R^{11}$ and $R^{12}$, which may be identical or different, represent:
a hydrogen atom,
a linear or branched $C_1$-$C_6$ alkyl group, preferably tert-butyl,
an aralkyl group, preferably phenylalkyl, preferably phenylmethyl,
a $C_1$-$C_6$ alkoxyalkyl group, preferably methoxyethyl,
a cycloalkyl group, preferably cyclohexyl, optionally mono- or polysubstituted with a $C_1$-$C_6$ alkyl group, preferably methyl,
an aryl, preferably phenyl, group, optionally mono- or polysubstituted with:
a halogen atom, preferably bromine,
a cyano group,
a sulphonamide group,
a nitro group,
a $C_1$-$C_6$ alkyl group, preferably methyl,
an alkoxy, preferably methoxy, group, or
a hydroxyl group,
or a heteroaryl group, preferably a pyridyl group, $R^{13}$ represents a heterocyclic group, preferably N-morpholyl, $R^{14}$ represents:
a linear or branched $C_1$-$C_6$ alkyl group, preferably methyl, or
an aryl group, preferably phenyl, optionally substituted with an alkoxy, preferably methoxy, group, $R^3$, $R^4$, which may be identical or different, represent:
a hydrogen atom,
a group $CH_2R^{15}$,
a heteroaryl group, preferably pyridyl, indyl, benzimidazyl, or pyrazyl optionally substituted with a $C_1$-$C_6$ alkyl group, preferably methyl, or
an aryl, preferably phenyl, group optionally mono- or polysubstituted with:
an alkoxy, preferably methoxy, group,
a trifluoroalkoxy, preferably trifluoromethoxy, group,
a halogen atom, preferably bromine, chlorine or iodine
a trifluoroalkyl, preferably trifluoromethyl, group,
a CONHalkyl group, preferably CONHmethyl,
an NHCOalkyl group, preferably NHCOmethyl,
a sulphonamide group,
a linear or branched $C_1$-$C_6$ alkyl group, preferably methyl, or
a methanesulphonamide group, $R^{15}$ represents:
an aryl, preferably phenyl, group optionally mono- or polysubstituted with:
a halogen atom preferably bromine, chlorine,
an alkoxy, preferably methoxy, group,
a trifluoroalkoxy, preferably trifluoromethoxy, group,
a linear or branched $C_1$-$C_6$ alkyl group, preferably methyl,
a $C_1$-$C_6$ trifluoroalkyl group, preferably trifluoromethyl,
a heteroaryl group, preferably pyridazinyl, optionally mono- or poly-substituted with a halogen atom, preferably chlorine,
a sulphonamide group, or
a methanesulphonamide group,
a group selected from the groups A, B, C, D or E as defined above, or a heteroaryl group, preferably:
a thiophenyl group,
a thiazyl group, optionally mono- or polysubstituted, preferably with a group selected from the groups A, B, C, D or E as defined above,
an imidazyl group,
an indyl group, optionally mono- or polysubstituted, preferably with a linear or branched C1-C6 alkyl group, preferably methyl,
a pyrazyl group, optionally mono- or polysubstituted, preferably with a linear or branched C1-C6 alkyl group, preferably ethyl, or with a group selected from A, B, C, D or E groups as defined above,
a pyridyl group optionally mono- or polysubstituted with an alkoxy, preferably methoxy, group, or a group selected from the groups A, B, C, D or E as defined above,
a group selected from the groups A, B, C, D or E as defined above,
a pyrimidinyl group optionally mono- or polysubstituted, preferably with a group selected from the groups A, B, C, D or E as defined above,
a benzimidazyl group, optionally mono- or polysubstituted, preferably with a linear or branched C1-C6 alkyl group, preferably methyl, or
a 1-H pyrrolo[2,3-b]pyridyl group In one embodiment the present invention relates to compounds of general formula I:

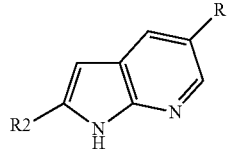

Formula I in which R represents:
a group $NHCOR^1$, or
a group $NR^3R^4$
where
$R^1$ represents:
an aryl, preferably phenyl, group optionally mono- or polysubstituted with:
a halogen atom, preferably bromine, fluorine or chlorine,
a nitro group,
a cyano group,
a methylthiazyl group,
an alkoxy, preferably methoxy, group,
a trifluoroalkoxy, preferably trifluoromethoxy, group,
an aryloxy, preferably phenyloxy, group,
a trifluoroalkyl, preferably trifluoromethyl, group,
a substituted or unsubstituted sulphonamide group, preferably N-methyl sulphonamide,
a heteroaryl, preferably pyridazyl, group, optionally mono- or poly-substituted with a halogen atom, preferably chlorine,
a linear or branched alkyl group, preferably $C_1$-$C_6$, preferably methyl, isopropyl
or a group selected from the groups A, B, C or D as defined below:

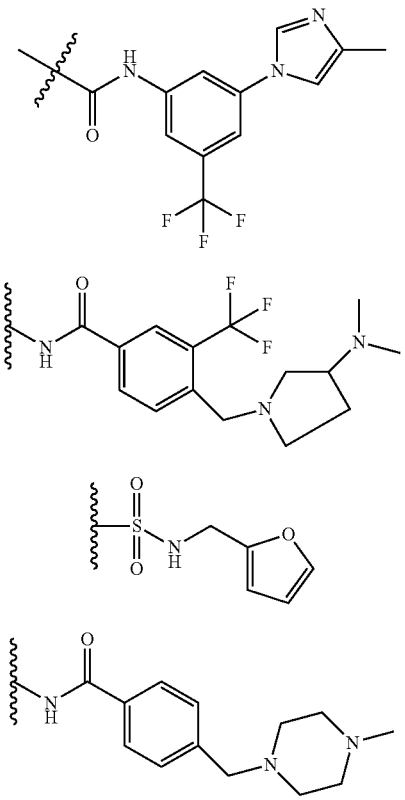

a heteroaryl group, preferably
a pyridyl group optionally mono- or poly-substituted with
  a sulphanyl, preferably propylsulphanyl, group,
a thiophenyl group,
a thiazyl group,
an imidazyl group,
a pyrazyl group optionally mono- or polysubstituted with
  an alkyl group, preferably methyl,
a quinoxaline group,
a dihydrobenzofuranyl group, or
an indyl group,
a cycloalkyl group, preferably cyclopropyl,
a linear or branched $C_1$-$C_6$ alkyl group, preferably ethyl, isopropyl, or
a $C_1$-$C_6$ aralkyl group, preferably phenylalkyl, preferably phenylmethyl, optionally mono- or poly-substituted with an alkoxy group, preferably methoxy, and/or a halogen atom, preferably bromine,
$R^2$ represents:
  an ester group $COOR^{14}$,
  an alkyl group $CH_2R^9$, $CH_2OCOR^{10}$, $CH_2NR^{11}R^{12}$,
  an amide group $CONR^7R^8$, or
  a group $COR^{13}$,
$R^7$ and $R^8$, which may be identical or different, represent:
  a hydrogen atom,
  a $C_1$-$C_6$ aminoalkyl group, preferably N,N-dimethylaminopropyl, or
  a $C_1$-$C_6$ morpholinoalkyl group, preferably N-morpholinoethyl,
$R^9$ represents:
  a heteroaryl group, preferably imidazyl or pyrryl,
  a heterocyclic group, preferably N-morpholinyl or tetrahydrofuranyl,
  an alkoxy group, preferably methoxy, or
  a hydroxyl group,
$R^{10}$ represents:
  a heteroaryl group, preferably quinoxaline,
$R^{11}$ and $R^{12}$, which may be identical or different, represent:
  a hydrogen atom,
  a linear or branched $C_1$-$C_6$ alkyl group, preferably tert-butyl,
  an aralkyl group, preferably phenylalkyl, preferably phenylmethyl,
  a $C_1$-$C_6$ alkoxyalkyl group, preferably methoxyethyl,
  a cycloalkyl group, preferably cyclohexyl, optionally mono- or polysubstituted with a $C_1$-$C_6$ alkyl group, preferably methyl,
  an aryl, preferably phenyl, group, optionally mono- or polysubstituted with:
    a halogen atom, preferably bromine,
    a cyano group,
    a sulphonamide group,
    a nitro group,
    a $C_1$-$C_6$ alkyl group, preferably methyl,
    an alkoxy, preferably methoxy, group, or
    a hydroxyl group,
    or a heteroaryl group, preferably a pyridyl group,
$R^{13}$ represents a heterocyclic group, preferably N-morpholyl,
$R^{14}$ represents:
  a linear or branched $C_1$-$C_6$ alkyl group, preferably methyl, or
  an aryl group, preferably phenyl, optionally substituted with an alkoxy, preferably methoxy, group,
$R^3$, $R^4$, which may be identical or different, represent:
  a hydrogen atom,
  a group $CH_2R^{15}$,
  a heteroaryl group, preferably pyridyl, indyl, benzimidazyl, or pyrazyl optionally substituted with a $C_1$-$C_6$ alkyl group, preferably methyl, or
  an aryl, preferably phenyl, group optionally mono- or polysubstituted with:
    an alkoxy, preferably methoxy, group,
    a trifluoroalkoxy, preferably trifluoromethoxy, group,
    a halogen atom, preferably bromine,
    a trifluoroalkyl, preferably trifluoromethyl, group,
    a CONHalkyl group, preferably CONHmethyl,
    an NHCOalkyl group, preferably NHCOmethyl,
    a sulphonamide group, or
    a methanesulphonamide group,
$R^{15}$ represents:
  an aryl, preferably phenyl, group optionally mono- or polysubstituted with:
    a halogen atom preferably bromine, chlorine,
    an alkoxy, preferably methoxy, group,
    a trifluoroalkoxy, preferably trifluoromethoxy, group,
    a $C_1$-$C_6$ alkyl group, preferably methyl,
    a $C_1$-$C_6$ trifluoroalkyl, preferably trifluoromethyl,
    a heteroaryl group, preferably pyridazinyl, optionally mono- or poly-substituted with a halogen atom, preferably chlorine,
    a sulphonamide group, or
    a methanesulphonamide group,
    or a heteroaryl group, preferably:
      a thiophenyl group,
      a thiazyl group,
      an imidazyl group,
      an indyl group,
      a pyrazyl group,
      a pyridyl group optionally mono- or polysubstituted with
        an alkoxy, preferably methoxy, group, or
      a group selected from the groups A, B, C and D as defined above.

According to one embodiment, the compounds of the present invention are represented by the compounds of formula II:

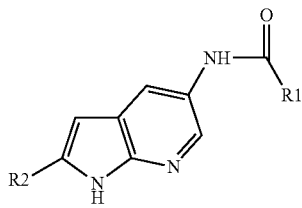

Formula II in which $R^1$ and $R^2$ represent the groups as previously defined, with respect to formula I or to its first embodiment presented above.

According to one embodiment, the compounds of the present invention are represented by the compounds of formula III:

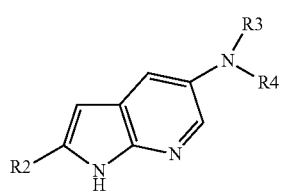

Formula III in which $R^2$, $R^3$ and $R^4$ represent the groups as previously defined, with respect to formula I or to its first embodiment presented above.

According to one embodiment, the compounds of the present invention are represented by the compounds of formula IV:

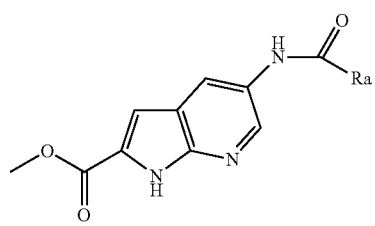

Formula IV in which $R^a$ represents:
 a cycloalkyl group, preferably cyclopropyl,
 a linear or branched $C_1$-$C_6$ alkyl group, preferably ethyl, isopropyl,
 an aryl group, preferably phenyl, optionally mono- or polysubstituted with:
  a cyano group,
  a halogen atom, preferably fluorine, bromine or chlorine,
  a methylthiazyl group,
  an alkoxy, preferably methoxy, group,
  a trifluoroalkoxy, preferably trifluoromethoxy, group,
  an aryloxy, preferably phenyloxy, group,
  a heteroaryl group, preferably pyridazinyl optionally mono- or polysubstituted with a halogen atom, preferably chlorine,
  an alkyl group, preferably $C_1$-$C_6$, preferably methyl,
  a trifluoroalkyl, preferably trifluoromethyl, group,
  a substituted or unsubstituted sulphonamide group, preferably N-methyl sulphonamide, or
  a group selected from the groups A, B, C and D as defined above,
 a heteroaryl group, preferably:
  a pyridyl group optionally substituted with a suiphanyl, preferably a propylsulphanyl, group,
  a thiophenyl group,
  a thiazyl group,
  an imidazyl group,
  a pyrazyl group optionally mono- or polysubstituted with an alkyl group, preferably methyl,
  a dihydrobenzofuranyl group, or
  an indyl group,
 or a $CH_2$-phenyl group, optionally substituted with an alkoxy group, preferably methoxy; a halogen atom, preferably bromine, According to one embodiment, the compounds of the present invention are represented by the compounds of formula V:

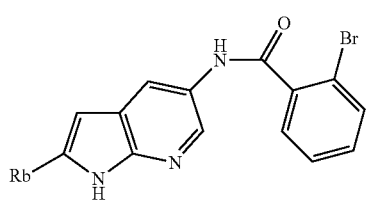

Formula V in which Rb represents:
 an ester group, preferably methyl ester,
 a group $CH_2E$,
 a group $CH_2OCOG$, or
 an amide group CONHI,
E represents:
 a hydroxyl group,
 an alkoxy, preferably methoxy, group,
 a secondary amine group substituted with:
  a linear or branched $C_1$-$C_6$ alkyl group, preferably tert-butyl,
  a cycloalkyl group, preferably cyclohexyl, unsubstituted or substituted with a $C_1$-$C_6$ alkyl group, a methyl,
  an aryl, preferably phenyl, group optionally mono- or polysubstituted with:
   a halogen atom, preferably fluorine or bromine,
   a cyano group,
   a nitro group,
   a $C_1$-$C_6$ alkyl group, preferably methyl,
   a hydroxyl group,
   an alkoxy, preferably methoxy, group,
   a tertiary amine group dimethylamine, or
   a sulphonamide group,
  a heteroaryl group preferably pyridyl, and/or
  an aralkyl group, preferably phenylalkyl, preferably phenylmethyl,
 a tertiary amine group disubstituted with an alkoxyalkyl group, preferably methoxypropyl,
 a heterocyclic group, preferably morpholyl, tetrahydrofuranyl,
 or a heteroaryl group, preferably pyrryl, imidazyl,
 G represents a heteroaryl group, preferably quinoxaline,
 I represents an aminoalkyl group, preferably N-dimethylaminopropyl.

According to one embodiment, the compounds of the present invention are represented by the compounds of formula VI:

Formula VI

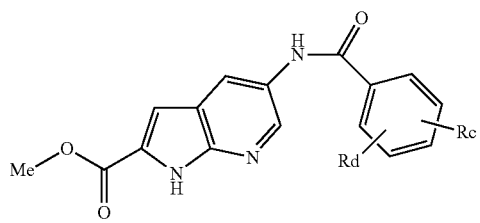

in which
Rd and Rc, which may be identical or different, represent:
- a hydrogen atom,
- a nitro group,
- a cyano group,
- a halogen atom, preferably fluorine, bromine or chlorine,
- a methylthiazyl group,
- a linear or branched $C_1$-$C_6$ alkyl group, preferably methyl or isopropyl,
- a trifluoroalkyl, preferably trifluoromethyl, group,
- a substituted or unsubstituted sulphonamide group, preferably N-methyl sulphonamide,
- a heteroaryl group, preferably pyridazinyl optionally mono- or polysubstituted with a halogen atom, preferably chlorine,
- an alkoxy, preferably methoxy, group,
- a trifluoroalkoxy, preferably trifluoromethoxy, group,
- a group selected from the groups A, B, C or D as defined above, or
- an aryloxy group, preferably phenyloxy, or Rd and Rc form, with the phenyl, a dihydrobenzofuran or indole ring.

According to one embodiment, the compounds of the present invention are represented by the compounds of formula VII:

Formula VII

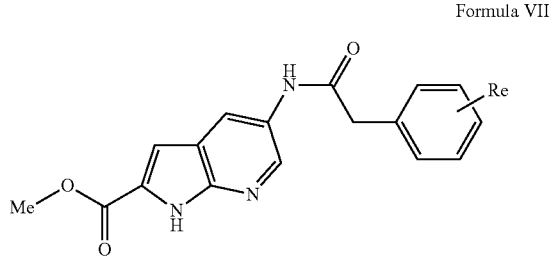

in which
Re represents:
- an alkoxy, preferably methoxy, group, or
- a halogen atom, preferably bromine.

According to one embodiment, the compounds of the present invention are represented by the compounds of formula VIII:

Formula VIII

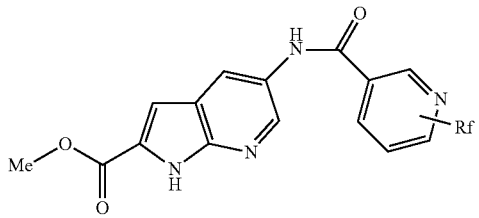

in which
Rf represents:
- a hydrogen atom, or
- a sulphenyl group, preferably propylsulphenyl.

According to one embodiment, the compounds of the present invention are represented by the compounds of formula IX:

Formula IX

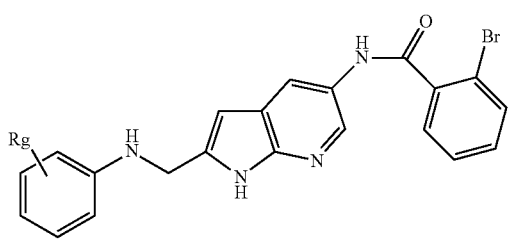

in which
Rg represents:
- a halogen atom, preferably bromine,
- a nitro group,
- a cyano group,
- a sulphonamide group,
- a hydrogen atom,
- a $C_1$-$C_6$ alkyl group, preferably methyl,
- a hydroxyl group, or
- an alkoxy group, preferably methoxy.

According to one embodiment, the compounds of the present invention are represented by the compounds of formula X:

Formula X

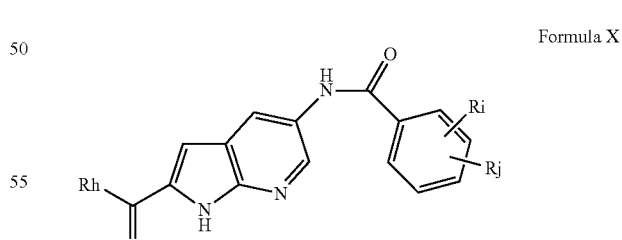

in which
Ri and Rj, which may be identical or different, represent:
- a halogen atom, preferably bromine, fluorine or chlorine,
- a nitro group,
- a methylthiazyl group,
- a hydrogen atom,
- an aryloxy, preferably phenyloxy, group,
- an alkoxy, preferably methoxy, group, a trifluoroalkoxy, preferably trifluoromethoxy, group,
a $C_1$-$C_6$ alkyl group, preferably methyl,
a trifluoroalkyl group, preferably trifluoromethyl,
a substituted or unsubstituted sulphonamide group, preferably N-methyl sulphonamide,
a heteroaryl group, preferably pyridazinyl, optionally mono- or polysubstituted with a halogen atom, preferably chlorine,
a group selected from the groups A, B, C or D as defined above, or
a cyano group,
or Ri and Rj form, with the phenyl, a dihydrobenzofuran, indole or quinoxaline ring.
Rh represents:
    an N-morpholyl group,
    a primary amine group,
    a secondary amine group NHJ, or
    OK,
J represents:
    an aminoalkyl group, preferably N,N-dimethylaminopropyl, or
    an N-morpholinoalkyl group, preferably N-morpholinoethyl,
K represents:
    an aryl group, preferably phenyl, optionally substituted with an alkoxy, preferably methoxy, or
    a $C_1$-$C_6$ alkyl group, preferably methyl.

According to one embodiment, the compounds of the present invention are represented by the compounds of formula XI:

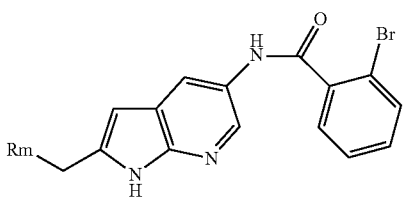

Formula XI in which
Rm represents:
    a hydroxyl group,
    a heteroaryl group, preferably pyrryl or imidazyl,
    a heterocyclic group, preferably trihydrofuranyl or N-morphoiyl,
    an alkoxy group, preferably methoxy,
    a secondary amine group substituted with:
        a linear or branched $C_1$-$C_6$ alkyl group, preferably tert-butyl,
        a cycloalkyl group, preferably cyclohexyl, optionally substituted with an alkyl group, preferably methyl,
        an aryl group, preferably phenyl, optionally substituted with:
            a halogen atom, preferably bromine,
            a cyano group,
            a sulphonamide group,
            a nitro group,
            a $C_1$-$C_6$ alkyl group, preferably methyl,
            a hydroxyl group, or
            an alkoxy, preferably methoxy, group,
        a heteroaryl group preferably pyridyl, or
        a phenylalkyl group, preferably phenylmethyl,
    a tertiary amine group N,N-dimethoxypropylamine, or
    a group OCOL
L represents a heteroaryl group, preferably quinoxaline.

According to one embodiment, the compounds of the present invention are represented by the compounds of formula XII:

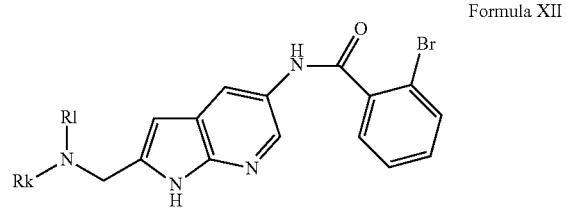

Formula XII in which
Rl and Rk, which may be identical or different, represent:
    an alkoxyalkyl group, preferably methoxypropyl,
    a hydrogen atom,
    a cycloalkyl group, preferably cyclohexyl, optionally substituted with a $C_1$-$C_6$ alkyl group, preferably methyl,
    an aryl group, preferably phenyl, optionally substituted with:
        a halogen atom, preferably bromine,
        a cyano group,
        a nitro group,
        a sulphonamide group,
        a $C_1$-$C_6$ alkyl group, preferably methyl,
        a hydroxyl group, or
        an alkoxy, preferably methoxy, group,
    a heteroaryl group, preferably pyridyl,
    an aralkyl group, preferably a phenylmethyl, or
    a linear or branched $C_1$-$C_6$ alkyl group, preferably tert-butyl; or
Rl and Rk form, with N, a morpholyl group.

According to one embodiment, the compounds of the present invention are represented by the compounds of formula XIII:

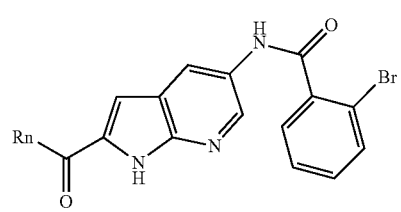

Formula XIII in which
Rn represents:
    an alkoxy, preferably methoxy, group, or
    a secondary amine group, preferably N,N-dimethylpropylamine.

According to one embodiment, the compounds of the present invention are represented by the compounds of formula XIV:

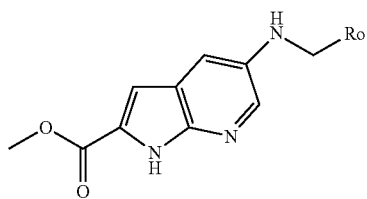

Formula XIV

In which Ro represents:

an aryl group, preferably phenyl, optionally mono- or polysubstituted, preferably with:

a halogen atom, preferably bromine or chlorine, an alkoxyl group, preferably methoxy, a linear or branched alkyl group, preferably C1-C6 alkyl group, preferably methyl group, a C1-C6 trifluoroalkyl group, preferably trifluoromethyl, a trifluoroalkoxy group, preferably trifluoromethoxy, a sulphonamide group, a methylsulphonamide group, a group chosen from the group A, B, C, D or E as defined above, a heteroaryl group, preferably:

a thiazyl group, substituted or not, preferably substituted by a group chosen from A, B, C, D or E groups as defined above, a thiophenyl group, an imidazyl group, an indyl group, optionally mono- or polysubstituted, preferably with a linear or branched C1-C6 alkyl group, preferably methyl, a pyrazyl group, optionally mono- or polysubstituted, preferably with a group chosen from A, B, C, D or E groups as defined above, or by a linear or branched C1-C6 alkyl, preferably ethyl, a benzimidazyl group, optionally mono- or polysubstituted, preferably with a C1-C6 alkyl group, preferably methyl, a piridyl group, optionally mono- or polysubstituted, preferably with a a group chosen from A, B, C, D or E groups as defined above, a pirimidinyl group, optionally mono- or polysubstituted, preferably with a group chosen from A, B, C, D or E groups as defined above, a 1-Hpyrrolo[2,3-b]pyridyl group In one embodiment the compound of formula XIV are chosen among:

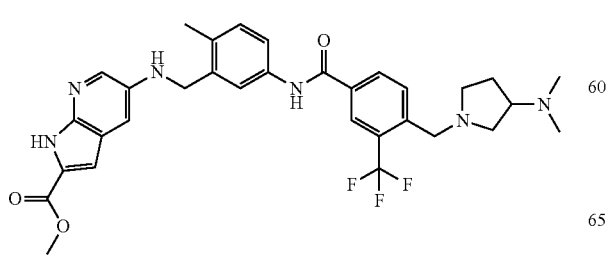

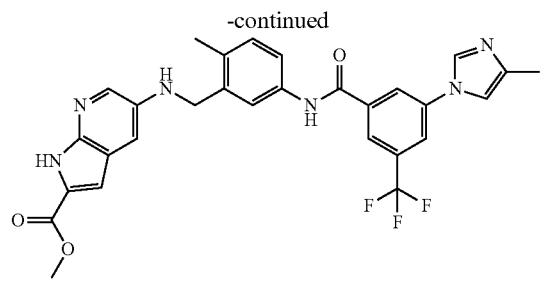

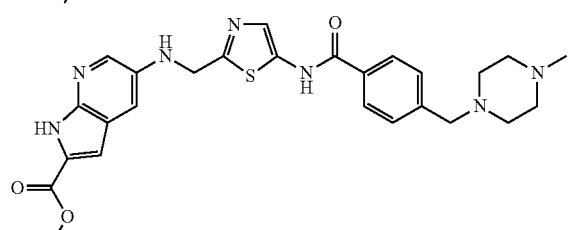

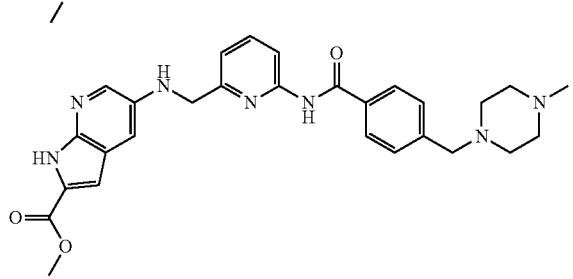

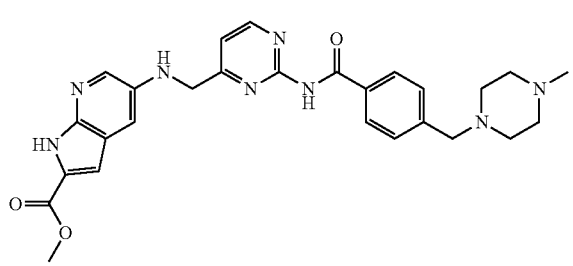

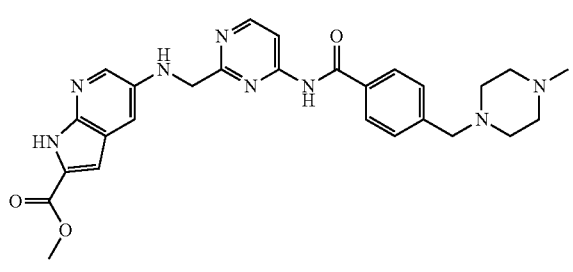

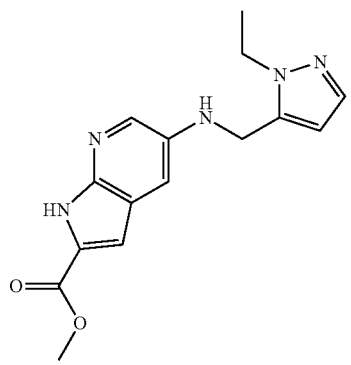

-continued

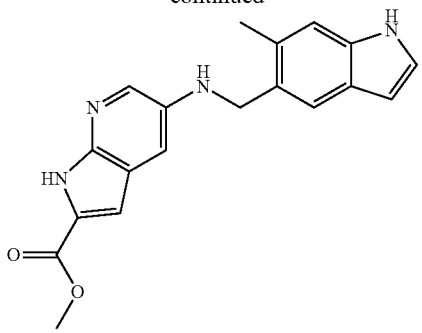

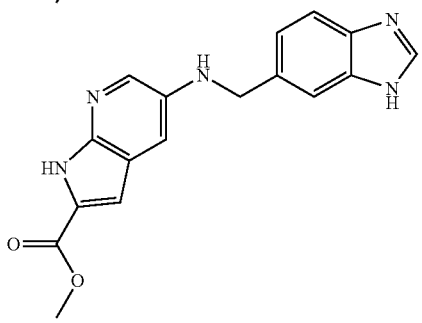

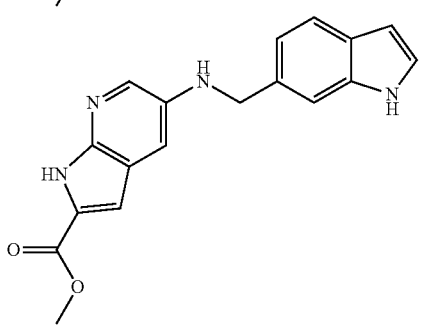

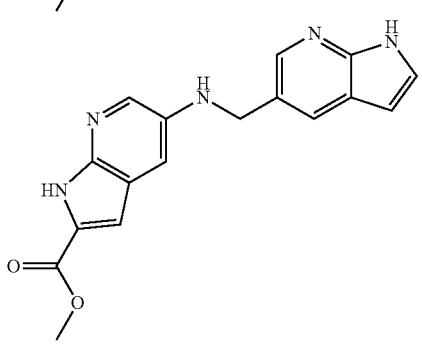

According to one embodiment, the compounds of the present invention are represented by the compounds of formula XV:

Formula XV

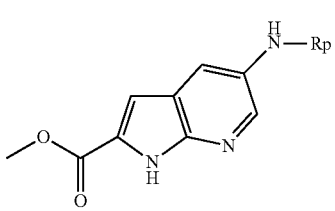

In which Rp represents:
  a heteroaryl group, preferably a pyridyl group,
  an aryl group, optionally mono- or polysubstituted, preferably with a:
    an alkoxyl group, preferably a methoxy,
    a halogen atom, preferably bromine or iodine,
    a —CONHalkyl group, preferably —CONHmethyl,
    a C1-C6 alkyl group, preferably Methyl According to one embodiment, the compounds of the present invention are represented by the compounds of formula XVI:

Formula XVI

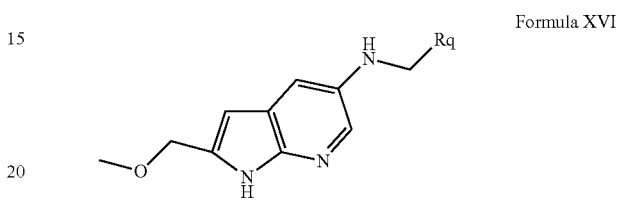

In which Rq represents:
  an aryl group, preferably phenyl, optionally mono- or poly substituted, preferably with:
    a linear or branched alkyl group, preferably C1-C6 alkyl group, preferably methyl group,
    a group chosen from the group A, B, C, D or E as defined above.

In one embodiment the compounds of formula XVI are chosen among:

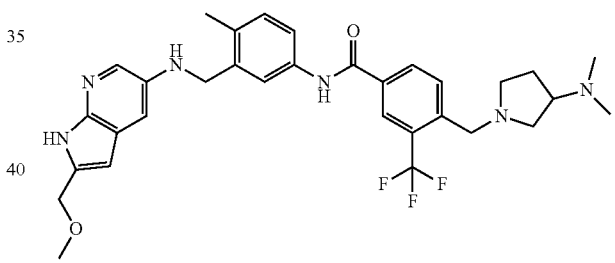

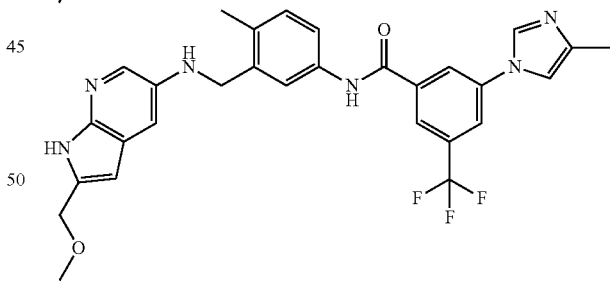

In general, the following definitions are used:
  "alkyl group": a linear or branched saturated aliphatic group with 1 to 6 carbon atoms. As examples, we may mention methyl, ethyl, propyl, butyl, tert-butyl, isopropyl, etc.
  "cycloalkyl group": a cyclic alkyl group with 3 to 10 carbon atoms. As examples, we may mention cyclopropyl, cyclobutyl, cyclopentyl, cyclohexyl, methylcyclohexyl, etc.
  "aryl group": a cyclic (mono- or polycyclic) aromatic group comprising between 5 and 10 carbon atoms. As examples, we may mention phenyl, naphthyl, etc.

"heteroaryl group": a cyclic (mono- or polycyclic) aromatic group comprising between 5 and 10 carbon atoms and between 1 and 3 heteroatoms, such as nitrogen, oxygen or sulphur. As examples, we may mention: pyridine, thiophene, thiazole, imidazole, pyrazole, pyrrole, quinoline, indole, pyridazine, quinoxaline, dihydrobenzofuran etc.

"heterocyclic group": a saturated cyclic group comprising between 5 and 10 carbon atoms and between 1 and 3 heteroatoms, such as nitrogen, oxygen and sulphur. As examples, we may mention: morpholine, tetrahydrofuran, etc.

"halogen atom": fluorine, chlorine, bromine or iodine.

"alkoxy group": an alkyl group bound to an oxygen. As examples, we may mention methoxy, ethoxy etc.

"aryloxy group": an aryl group bound to an oxygen. As examples, we may mention phenyloxy, etc.

"sulphonamide group":

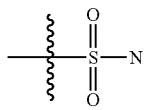 [SMILES: *S(N)(=O)=O]

"N-methyl sulphonamide group":

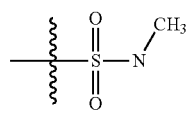

"methanesulphonamide group":

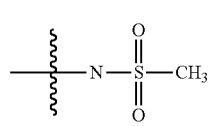 [SMILES: *NS(C)(=O)=O]

"aralkyl group": an alkyl group substituted with an aryl group

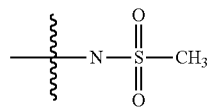

"aminoalkyl group": an alkyl group substituted with an amine group

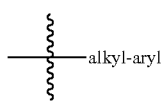

"hydroxyl group": OH

"alkoxyalkyl group": an alkyl group substituted with an alkoxy group

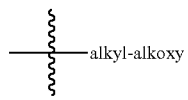

"sulphanyl group":

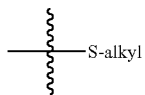

"substituted phenyl": a phenyl mono- or poly-substituted with:
a halogen atom,
a nitro group —(NO$_2$),
a cyano group (CN),
a methylthiazyl group,

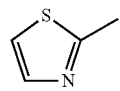

an alkoxy group,
an aryloxy group,
an alkyl group,
a sulphonamide group,
an N-methyl sulphonamide group,
a methanesulphonamide group,
a heteroaryl group,
a hydroxyl group,
a tertiary amine group,
a group —CONHalkyl,
a group —NHCOalkyl, or
a group selected from the groups A, B, C and D as defined above, "pyridyl": radical derived from pyridine

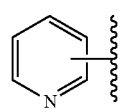

"thiophenyl": radical derived from thiophene

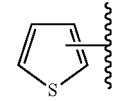

"thiazyl": radical derived from thiazole

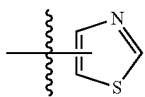

"imidazyl": radical derived from imidazole

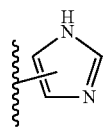

"pyrazyl": radical derived from pyrazole

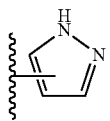

"quinoxaline":

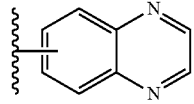

"dihydrobenzofuranyl": radical derived from dihydrobenzofuran

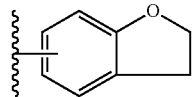

"pyrryl": radical derived from pyrrole

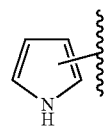

"indyl": radical derived from indole

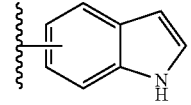

"pyridazinyl": radical derived from pyridazine

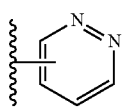

"N-morpholyl": radical derived from morpholine

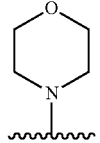 [SMILES: *N1CCOCC1]

"benzimidazyl": radical derived from benzimidazole

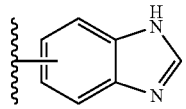

"pyrimidinyl": radical derived from pyrimidine

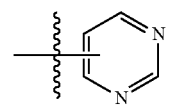

"1-Hpyrrolo[2,3-b]pyridyl: radical derived from 1-Hpyrrolo[2,3-b]pyridine

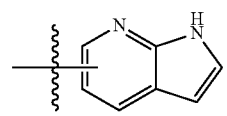

———, such a single bond in the represented compound corresponds to a methyl group In one embodiment, the invention relates to compounds chosen from the group consisting of: ND0009, ND0019, ND0020, ND0021, ND0029, ND0031, ND0033, ND0037, ND0038, ND0045, ND0047, ND0057, ND0072, ND0074, ND0076, ND0077, ND0082, ND0085, ND0087, ND0088, ND0089, ND0090, ND0091, ND0093, ND0094, ND0096, ND0098, ND0101, ND0117, ND0118, ND0119. Those compounds, which are represented below are characterized in that they present an inhibition percentage greater than 50% for kinase.

In one embodiment, the invention relates to compounds chosen from the group consisting of: ND0009, ND0019, ND0020, ND0021, ND0029, ND0031, ND0033, ND0037, ND0038, ND0045, ND0047, ND0057, ND0072, ND0074, ND0076, ND0077, ND0082, ND0085, ND0087, ND0088, ND0089, ND0090, ND0091, ND0093, ND0094, ND0096, ND0098, ND0101, ND0117, ND0118, ND0119. Those compounds, which are represented below are characterized in that they present an inhibition percentage greater than 50% for the AbI WT kinase.

In one embodiment, the invention relates to compounds chosen from the group consisting of ND0118, ND0119, ND0096. Those compounds, which are represented below are characterized in that they present an inhibition percentage greater than 50% for the AbI T315I kinase.

In one embodiment, the invention relates to compounds chosen from the group consisting of: ND009, ND0020, ND0021, ND0037, ND0038, ND0047, ND0057, ND0072, ND0074, ND0076, ND0077, ND0087, ND0088, ND0089, ND0090, ND0091, ND0093, ND0094, ND0096, ND0098, ND0117, ND0118, ND0119. Those compounds, which are represented below are characterized in that they present an inhibition percentage greater than 50% for the Src kinase.

In one embodiment, the invention relates to compounds chosen from the group consisting of: ND0117, ND0118, ND0119. Those compounds, which are represented below are characterized in that they present an IC50 inferior to $1\cdot10^{-9}$M for the kinase.

In one embodiment the invention relates to compounds chosen from the group consisting of: ND0117, ND0118, ND0119. Those compounds, which are represented below are characterized in that they present an IC50 inferior to $1\cdot10^{-9}$M for AbI WT kinase.

In one embodiment the invention relates to compounds is ND0118. This compound, which is represented below is characterized in that it presents an IC50 inferior to $1\cdot10^{-9}$M for Src kinase.

In one embodiment the invention relates to compounds chosen from the group consisting of: ND0072, ND0074, ND0077, ND0087, ND0089, ND0090, ND0096, ND0117, ND0119. Those compounds, which are represented below are characterized in that they present an IC50 comprised between $1\cdot10^{-7}$ to $1\cdot10^{-9}$M for the kinase.

In one In one embodiment the invention relates to compounds chosen from the group consisting of: ND0072, ND0074, ND0077, ND0087, ND0089, ND0090, ND0096. Those compounds, which are represented below are characterized in that they present an IC50 comprised between $1\cdot10^{-7}$ to $1\cdot10^{-9}$M for the AbI WT kinase.

In one embodiment the invention relates to compounds chosen from the group consisting of: ND0072, ND0074, ND0077, ND0087, ND0089, ND0090, ND0117, ND0119. Those compounds, which are represented below are characterized in that they present an IC50 comprised between $1\cdot10^{-7}$ to $1\cdot10^{-9}$M for the Src kinase.

In one In one In one embodiment the invention relates to compounds chosen from the group consisting of: ND0009, ND0019, ND0020, ND0021, ND0031, ND0037, ND0038, ND0047, ND0057, ND0076, ND0082, ND0085, ND0088, ND0091, ND0093, ND0094, ND0098, ND0096, ND0118, ND0119, ND0077. Those compounds, which are represented below are characterized in that they present an 1050 comprised between $1\cdot10^{-5}$ to $1\cdot10^{-7}$M for the kinase.

In one embodiment the invention relates to compounds chosen from the group consisting of: ND0009, ND0019, ND0020, ND0021, ND0031, ND0037, ND0038, ND0047, ND0057, ND0076, ND0082, ND0085, ND0088, ND0091, ND0093, ND0094, ND0098. Those compounds, which are represented below are characterized in that they present an IC50 comprised between $1\cdot10^{-5}$ to $1\cdot10^{-7}$M for the AbI WT kinase.

In one embodiment the invention relates to compounds chosen from the group consisting of: ND0096, ND0118, ND0119. Those compounds, which are represented below are characterized in that they present an IC50 comprised between $1\cdot10^{-5}$ to $1\cdot10^{-7}$ M for the AbI T315I kinase.

In one embodiment the invention relates to compounds chosen from the group consisting of: ND0009, ND0057, ND0077, ND0088, ND0091, ND0093, ND0094, ND0096, ND0098. Those compounds, which are represented below are characterized in that they present an IC50 comprised between $1\cdot10^{-5}$ to $1\cdot10^{-7}$ M for the Src T315I kinase.

In one embodiment the invention relates to compounds chosen from the group consisting of: ND0006, ND0010, ND0011, ND0029. Those compounds, which are represented below are characterized in that they present an IC50 greater than $1\cdot10^{-5}$M for the AbI WT kinase.

In one embodiment the invention relates to compounds chosen from the group consisting of: ND0117, ND0118, ND0119. Those compounds, which are represented below are characterized in that they present an IC50 inferior to $1\cdot10^{-8}$ M at 72 hours for the K562 Bcr-AbI kinase.

In one embodiment the invention relates to compounds chosen from the group consisting of: ND0117, ND0119, ND0076, ND0087, ND0090, ND0096, ND0072, ND 0074, ND0089. Those compounds, which are represented below are characterized in that they present an IC50 comprised between $1\cdot10^{-8}$ and $1\cdot10^{-8}$ M for the K562 Bcr-AbI kinase.

In one embodiment the invention relates to compounds chosen from the group consisting of: ND0117, ND0119. Those compounds, which are represented below are characterized in that they present an IC50 comprised between $1\cdot10^{-8}$ and $1\cdot10^{-8}$ M for the K562 Bcr-AbI kinase at 24 h.

In one embodiment the invention relates to compounds chosen from the group consisting of: N00076, ND0087, ND0090, ND0096, ND0072, ND 0074, ND0089. Those compounds, which are represented below are characterized in that they present an IC50 comprised between $1\cdot10^{-8}$ and $1\cdot10^{-6}$ M for the K562 Bcr-AbI kinase at 72 h.

In one embodiment the invention relates to compounds chosen from the group consisting of: ND0020, ND0076, ND0087, ND0090, ND0096, ND0118. Those compounds, which are represented below are characterized in that they present an IC50 comprised between $1\cdot10^{6}$ and $1\cdot10^{-5}$ M for the K562 Bcr-AbI kinase.

In one embodiment the invention relates to compounds chosen from the group consisting of: ND0020, ND0076, ND0087, ND0090, ND0096, ND0118. Those compounds, which are represented below are characterized in that they present an IC50 comprised between $1\cdot10^{-6}$ and $1\cdot10$ M for the K562 Bcr-AbI kinase at 24 h.

In one embodiment the invention relates to compound ND0020. This compound, which is represented below are characterized in that it presents an IC50 comprised between $1\cdot10^{-6}$ and $1\cdot10^{-5}$ M for the K562 Bcr-AbI kinase at 72 h.

In one embodiment the present invention relates to compound chosen from the group consisting of: ND0072, ND0074, ND0089, ND0009. Those compounds, which are represented below are characterized in that they present an IC50 greater than $1\cdot10^{-5}$ for the K562 Bcr-AbI kinase.

In one embodiment the present invention relates to compound chosen from the group consisting of: ND0072, ND0074, ND0089. Those compounds, which are represented below are characterized in that they present an IC50 greater than $1\cdot10^{-5}$ for the K562 Bcr-AbI kinase at 24 h.

In one embodiment the present invention relates to compound ND0009. This compound, which is represented below is characterized in that it presents an IC50 greater than $1\cdot10^{-5}$ for the K562 Bcr-AbI kinase at 72 h.

In one embodiment the present invention relates to compound ND0009. This compound, which is represented below is characterized in that it presents an IC50 greater than $1\cdot10^{-5}$ for the U937 Bcr-AbI kinase at 72 h.

In one embodiment, the invention relates to compounds, characterized in that they are selected from the group constituted by methyl 5-(2-bromobenzamido)-1H-pyrrolo[2,3-b]pyridine-2-carboxylate, methyl 5-(2-fluoro-6-methoxybenzamido)-1H-pyrrolo[2,3-b]pyridine-2-carboxylate, N-(2-((4-hydroxyphenylamino)methyl)-1H-pyrrolo[2,3-b]pyridin-5-yl)-2-bromobenzamide, N-(2-((1H-pyrrol-2-yl)methyl)-1H-pyrrolo[2,3-b]pyridin-5-yl)-2-bromobenzamide, 2-bromo-N-(2-(methoxymethyl)-1H- pyrrolo[2,3-b]pyridin-5-yl)benzamide, or 5-(2-bromobenzamido)-N-(3-(dimethylamino) propyl)-1H-pyrrolo[2,3-b]pyridine-2-carboxamide.

When the compounds according to the invention comprise one or more asymmetric carbons, the compounds according to the invention can be obtained in the form of isomers and the invention relates to the compounds in all their forms, namely the enantiomeric, diastereoisomeric, racemic forms or mixtures.

When the compounds comprise bonds that can give geometric isomers, the present invention relates to all the geometric isomers, isolated or as a mixture of the compounds according to the invention.

The compounds according to the invention can be in solvated form and in non-solvated form.

According to the invention, all the pharmaceutically acceptable salts of the compounds according to the invention are included within the scope of the invention, in particular the salts of weak acids and of weak bases.

The present invention also relates to the use of the compounds according to the invention as inhibitors of protein kinases.

In one embodiment, the compounds according to the invention are used as inhibitor of protein kinase Abl.

In another embodiment, the compounds according to the invention are used as inhibitors of protein kinases Src.

The compounds of the invention can be used in the treatment of pathologies associated with deregulation of protein kinases:
- in the case of chronic or acute myeloproliferative disorders such as certain leukaemias,
- in the case of hepatic, pancreatic, gastric, oesophageal and colorectal gastrointestinal cancers,
- in the case of breast cancer and ovarian cancer,
- in the case of lung cancer.

According to another aspect, the invention relates to a medicinal product comprising a compound according to the invention as active principle. Thus, the compounds according to the invention can be used as medicinal products in the treatment of pathologies associated with deregulation of protein kinases:
- in the case of chronic or acute myeloproliferative disorders such as certain leukaemias,
- in the case of hepatic, pancreatic, gastric, oesophageal and colorectal gastrointestinal cancers,
- in the case of breast cancer and ovarian cancer,
- in the case of lung cancer.

The present invention also relates to pharmaceutical compositions comprising, as active principle, a compound of the invention and a pharmaceutically acceptable excipient.

"Pharmaceutical composition" means any composition comprising an effective dose of a compound of the invention and at least one pharmaceutically acceptable excipient. Said excipients are selected, depending on the pharmaceutical form and the desired method of administration, from the usual excipients known by a person skilled in the art.

The compositions according to the invention can be used in the treatment of pathologies associated with deregulation of protein kinases:
- in the case of chronic or acute myeloproliferative disorders such as certain leukaemias,
- in the case of hepatic, pancreatic, gastric, oesophageal and colorectal gastrointestinal cancers,
- in the case of breast cancer and ovarian cancer,
- in the case of lung cancer.

The invention also relates to the method of preparation of the compounds starting from methyl 5-nitro-1H-pyrrolo[2,3-b]pyridine-2-carboxylate (commercially available from the company Azasynth).

In a first embodiment, the method according to the invention is represented by scheme 1.

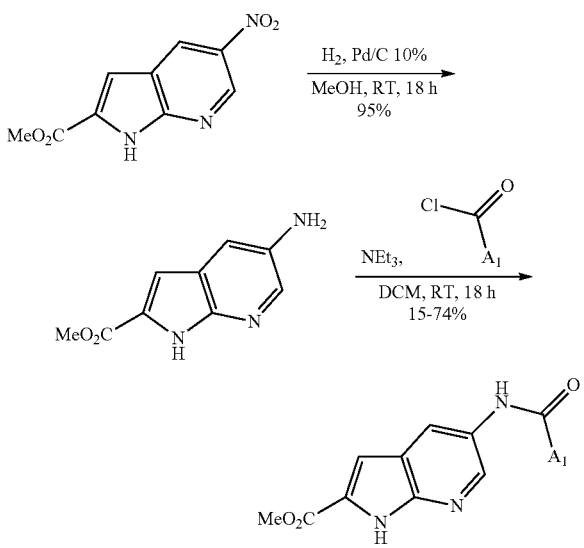

In one embodiment the method according to the invention is represented by scheme 1bis.

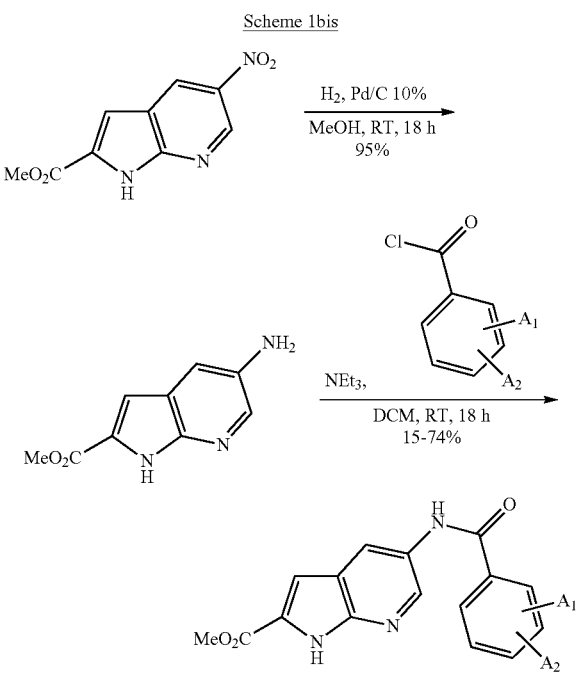

The method comprises at least the stages of:

a) catalytic hydrogenation of methyl 5-nitro-1H-pyrrolo[2,3-b]pyridine-2-carboxylate, in the presence of palladium on charcoal and under hydrogen atmosphere (Seela, F., Gumbiowski, R. *Heterocycles*, 1989, 29 (4), 795-805)

b) reaction of the amine formed with various acyl chlorides to give the corresponding amides at yields ranging from 15 to 74% after purification on silica gel (Mouaddib, A., Joseph, B. et al., *Synthesis*, 2000, (4), 549-556) and c) production and characterization of the compound.

In a second embodiment, the method is represented by scheme 2
Scheme 2
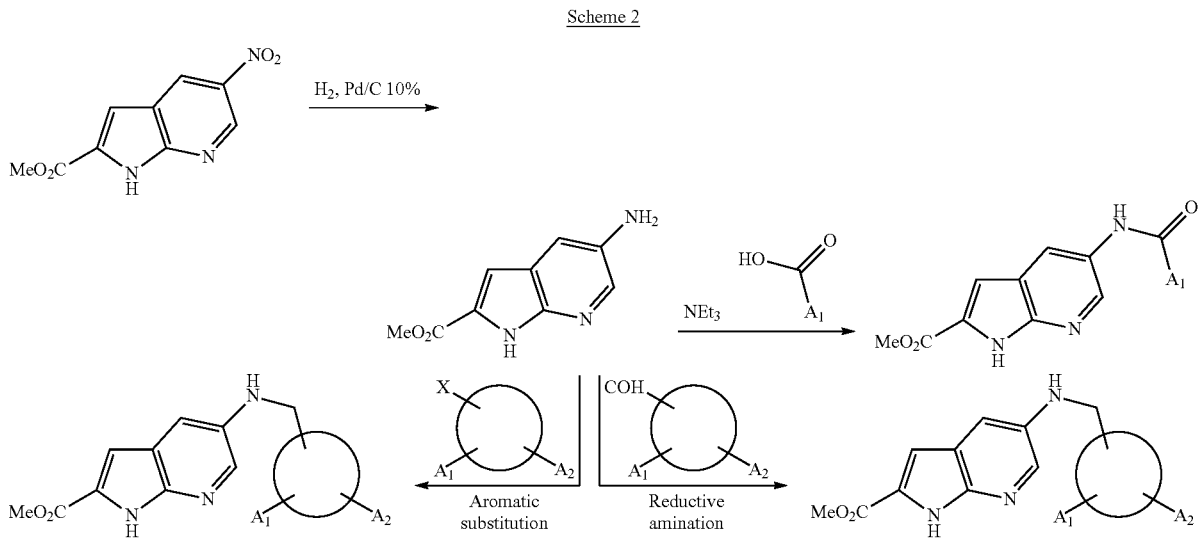
Wherein
represents an aryl or heteroaryl group.
In one embodiment
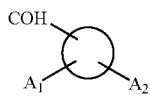
represents
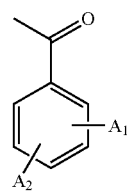
In one embodiment
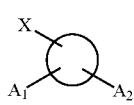
represents
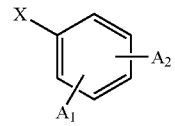
In one embodiment
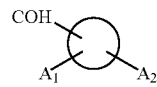
represents
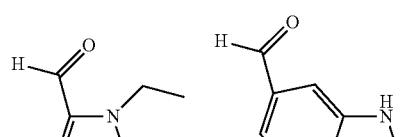
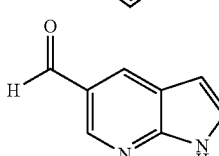 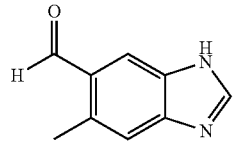
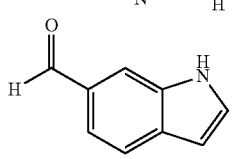 or 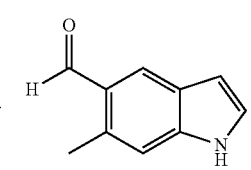
The process comprises the following steps:
a) catalytic hydrogenation of methyl 5-nitro-1H-pyrrolo[2,3-b]pyridine-2-carboxylate, in the presence of palladium on charcoal and under hydrogen atmosphere (Seela, F., Gumbiowski, R. *Heterocycles*, 1989, 29 (4), 795-805), following by step b, c or d, b) reaction of the amine formed with various acyl chlorides or carboxylic acids to give the corresponding amides at yields ranging from 15 to 74% after purification on silica gel (Mouaddib, A., Joseph, B. et al., *Synthesis*, 2000, (4), 549-556), c) aromatic substitution of various aromatic halide by the methyl 5-amino-1H-pyrrolo[2,3-b]pyridine-2-carboxylate to give the corresponding amino-aromatic (Zhu, Xiao-Qing et al *Journal of Physical Chemistry B*, 2008, 112(37), 11694-11707), d) reductive amination of the methyl 5-amino-1H-pyrrolo [2,3-b]pyridine-2-carboxylate with various aromatic aldehyde in the presence of boron hydride to give corresponding benzylic amines (Wang, Dong Mei et al *Journal of Combinatorial Chemistry*, 2009, 11(4), 556-575), and e) production and characterization of the compound.

In a third embodiment, the method is represented by scheme 3.

fication on silica gel (Nagarathnam, D., *Journal of Heterocyclic Chemistry*, 1992, 29 (6), 1371-3) and e) production and characterization of the compound.

In a fourth embodiment of the invention, the method is represented by scheme 4.

Scheme 4

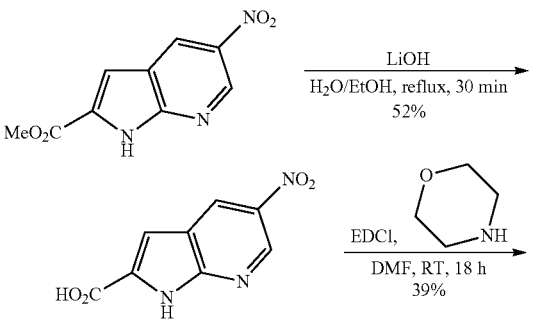

Scheme 3

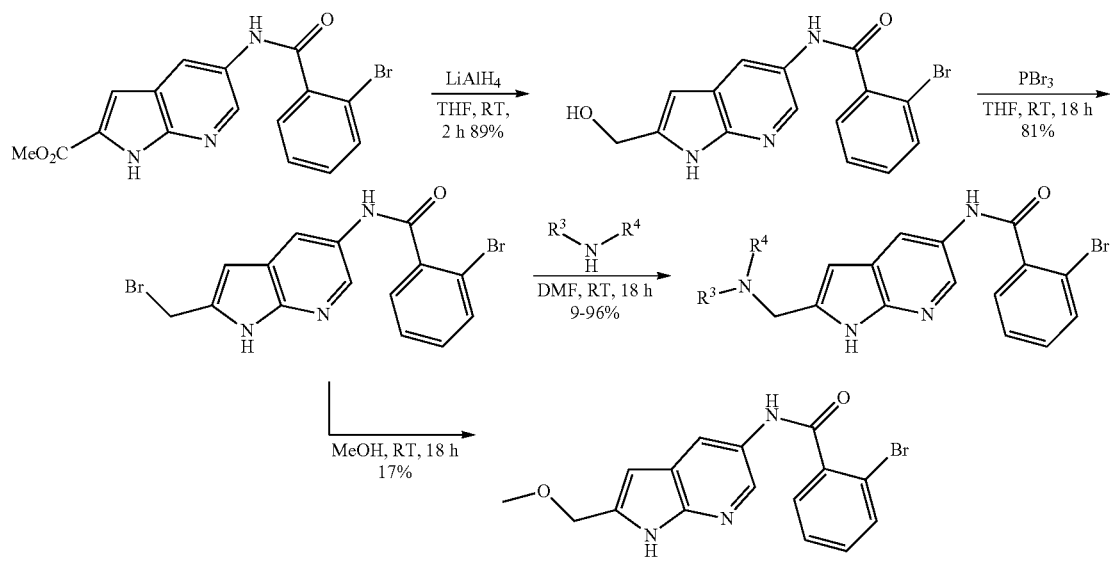

The method comprises at least the stages of:

a) selective reduction of the ester function of methyl 5-(2-bromobenzamido)-1H-pyrrolo[2,3-b]pyridine-2-carboxylate by lithium aluminium hydride at room temperature (Karrer, P., Boettcher, Augusta, *Helvetica Chimica Acta*, 1953, 36, 570-2), b) conversion of the alcohol to alkane bromide by PBr$_3$, at room temperature for 18 h in THF (raw yield of 81%) (Ku, Jin-Mo; J. et al., *Journal of Org Chemistry*, 2007, 72 (21), 8115-8118). This reaction is followed by the following stages c) or d)

c) dissolution in methanol, to give the methoxyazaindole obtained by reaction of the solvent on the halogenated function, at room temperature d) reaction of the alkane bromide with a primary or secondary amine in anhydrous dimethylformamide, at room temperature for 18 h, to give the corresponding 7-azaindoles at yields ranging from 9 to 96% after puri- -continued

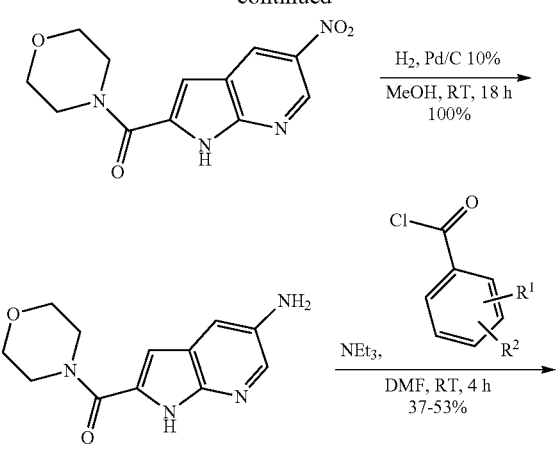

-continued

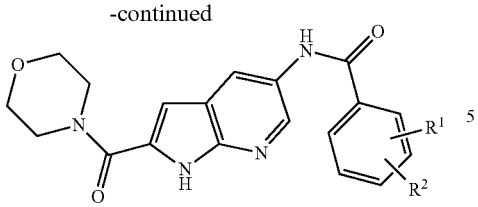

The method comprises at least the stages of:
a) saponification of the ester of methyl 5-nitro-1H-pyrrolo [2,3-b]pyridine-2-carboxylate by lithium hydroxide (Kanth, Sribhashyam R. et al., *Heterocycles* 2005, 65 (6), 1415-1423),
b) peptide coupling by means of N-(3-dimethylaminopropyl)-N'-ethylcarbodiimide (EDCl) hydrochloride and morpholine,
c) hydrogenation of the amide obtained by catalytic palladium,
d) reaction of the compound obtained with various acyl chlorides, in the presence of triethylamine in dimethylformamide, to obtain the desired 7-azaindoles, and
e) production and characterization of the compound.

In a fifth embodiment the method of the invention is represented by scheme 5.

Scheme 5

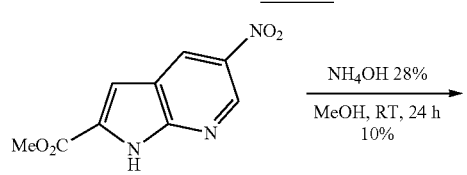

-continued

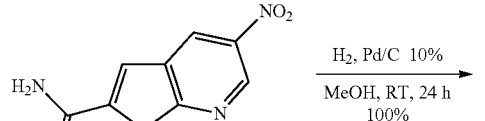

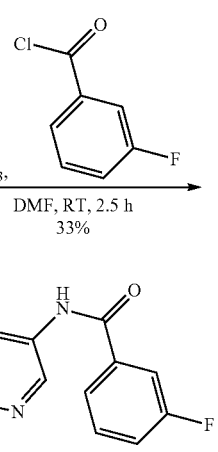

The method comprises at least the stages of:
a) reaction of methyl 5-nitro-1H-pyrrolo[2,3-b]pyridine-2-carboxylate with aqueous ammonia at room temperature for 24 hours to obtain the primary amide of azaindole,
b) hydrogenation of the compound obtained on Pd/C,
c) reaction with 3-fluorobenzoyl to give the desired compound, and
d) production and characterization of the compound.

In a sixth embodiment, the method of the invention is represented by scheme 6.

Scheme 6

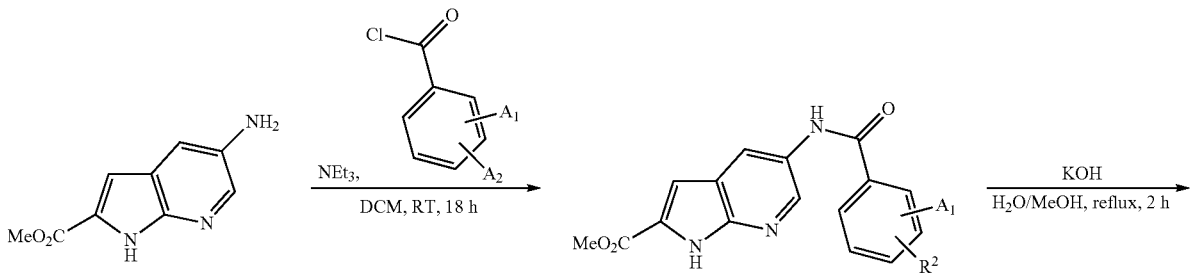

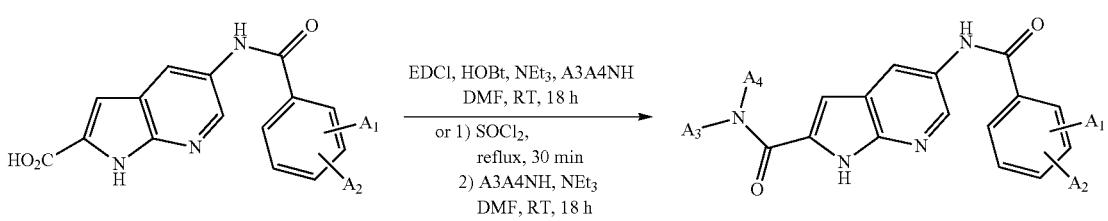

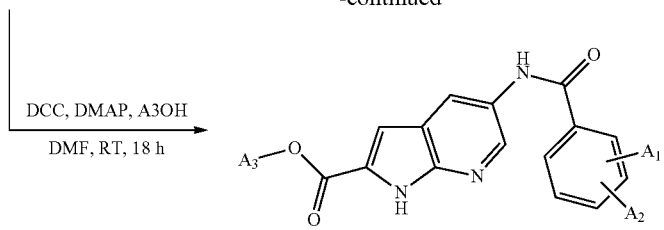

The method comprises at least the stages of:
a) reaction of methyl 5-amino-1H-pyrrolo[2,3-b]pyridine-2-carboxylate with various acyl chlorides,
b) saponification of the compounds obtained by the action of potassium hydroxide under reflux in a water-methanol mixture,
c) reaction of the compound obtained on various alcohols or amines, and
d) production and characterization of the compound.

In a seventh embodiment, the method of the invention is represented by scheme 7.

Scheme 7

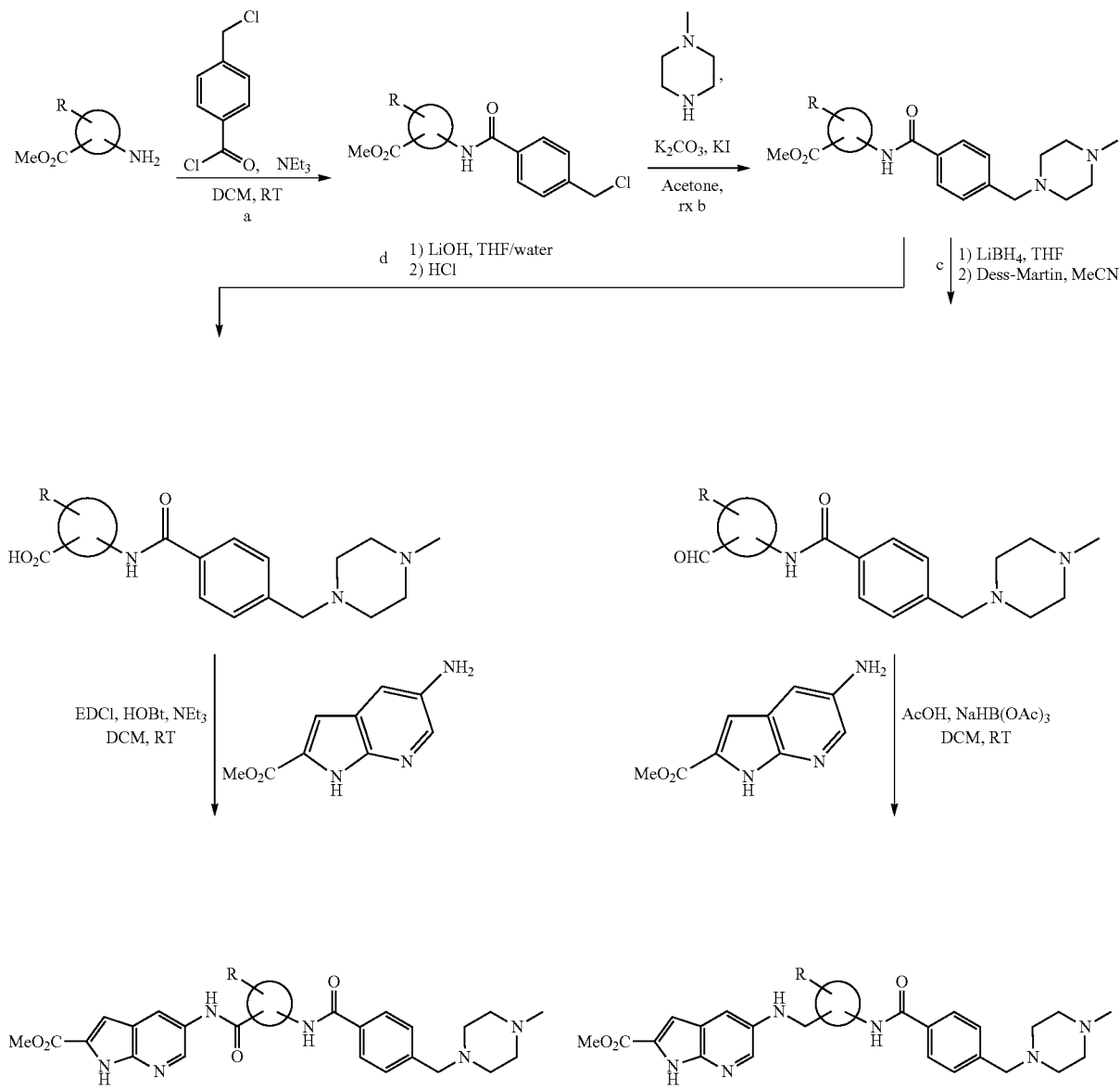

Wherein

represents various aromatic amines carrying an ester function on the aromatic ring.

In one embodiment

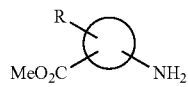

represents:

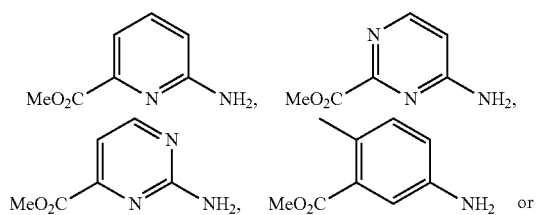

-continued

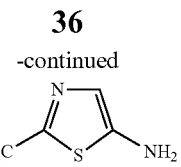

The method comprises at least the stages of:

a) Reaction between various aromatic amines carrying an ester function on the aromatic ring and 4-(chloromethyl) benzoyle chloride to give the desired amine (Ding, Qiang et al, WO2005034869), b) Substitution of the alkyl chloride by N-methylpiperazine (Liu, Yi-Feng et a, *Organic Process Research & Development*, 2008, 12(3), 490-495), this step is following by step c or d c) Saponification of the methylic ester followed by the peptidic coupling to give the desired inhibitor, d) Reduction of the methylic ester into primary alcohol by lithium borohydride (Rosen, Brad M. et al, Journal of the American Chemical Society, 2009, 131(47), 17500-17521), followed by the oxidation of the alcohol into aldehyde by the Dess-Martin reagent (Bonneau, Anne-Laure et al., WO2008146174), and followed by the reductive amination to give the desired inhibitor.

In a eighth embodiment, the method of the invention is represented by scheme 8.

Scheme 8

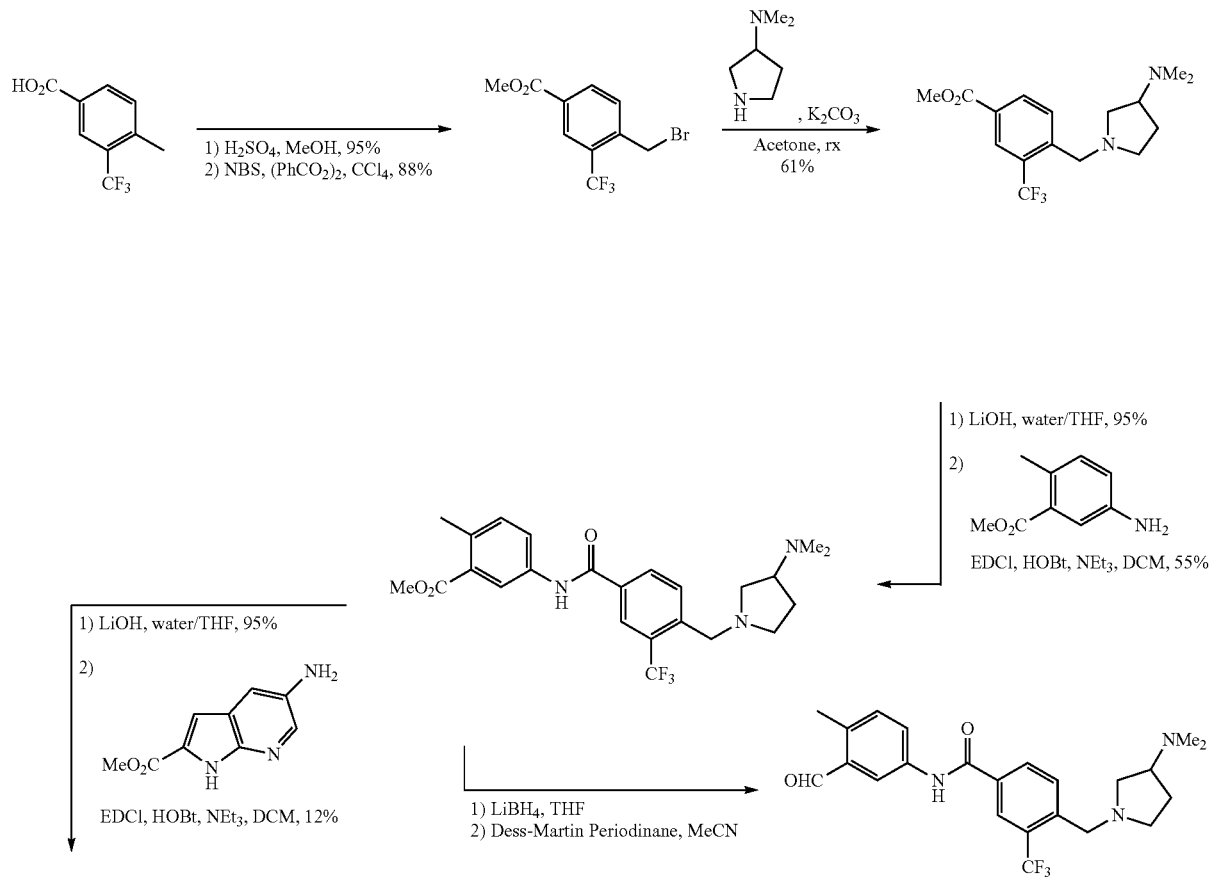

-continued

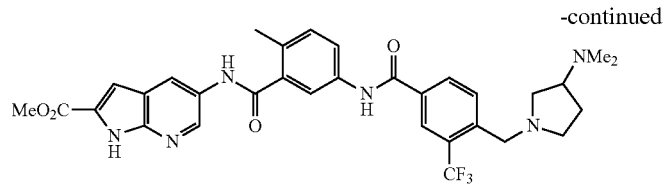

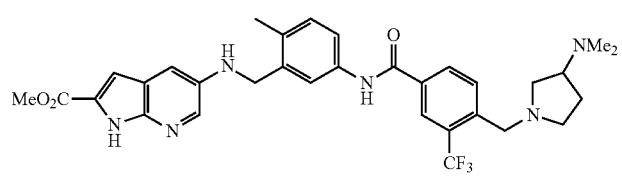

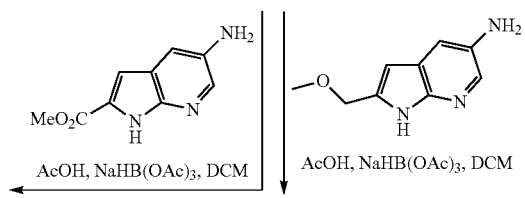

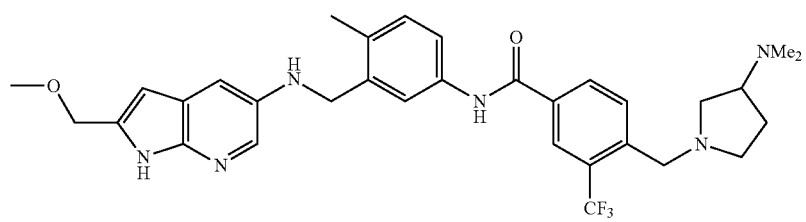

The method comprises at least the stages of:
a) esterification of 3-(trifluoromethyl)-4-methylbenzoic acid in methanol in an acid medium to give the methylic ester,
b) radical bromination of the methyl group (Sun, Yewei et al, *Bioorganic & Medicinal Chemistry*, 2008, 16(19), 8868-8874),
c) brome substitution by dimethylpyrrolidine,
d) saponification of the methylic ester,
e) peptidic coupling with methyl 5-amino-2-methylbenzoate, this stage is followed by step f, g or h,
f) new saponification of the methylic ester and peptidic coupling with the methyl 5-amino-1H-pyrrolo[2,3-b]pyridine carboxylate to give the desired inhibitor,
g) reduction of the methylic ester into aldehyde followed by the reductive amination with methyl 5-amino-1H-pyrrolo[2,3-b]pyridine-2-carboxylate to give the desired inhibitor,
h) reduction of the methylic ester into aldehyde followed by the reductive amination with 5-amino-2-methoxymethyl-1H-pyrrolo[2,3-b]pyridine, In a ninth embodiment, the method of the invention is represented by scheme 9.

Scheme 9

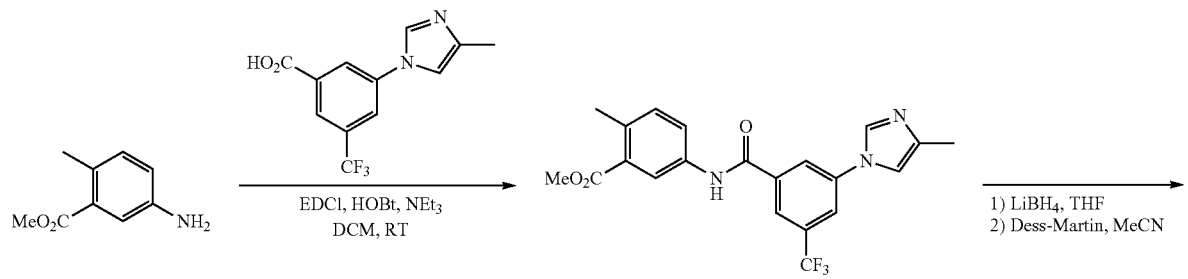

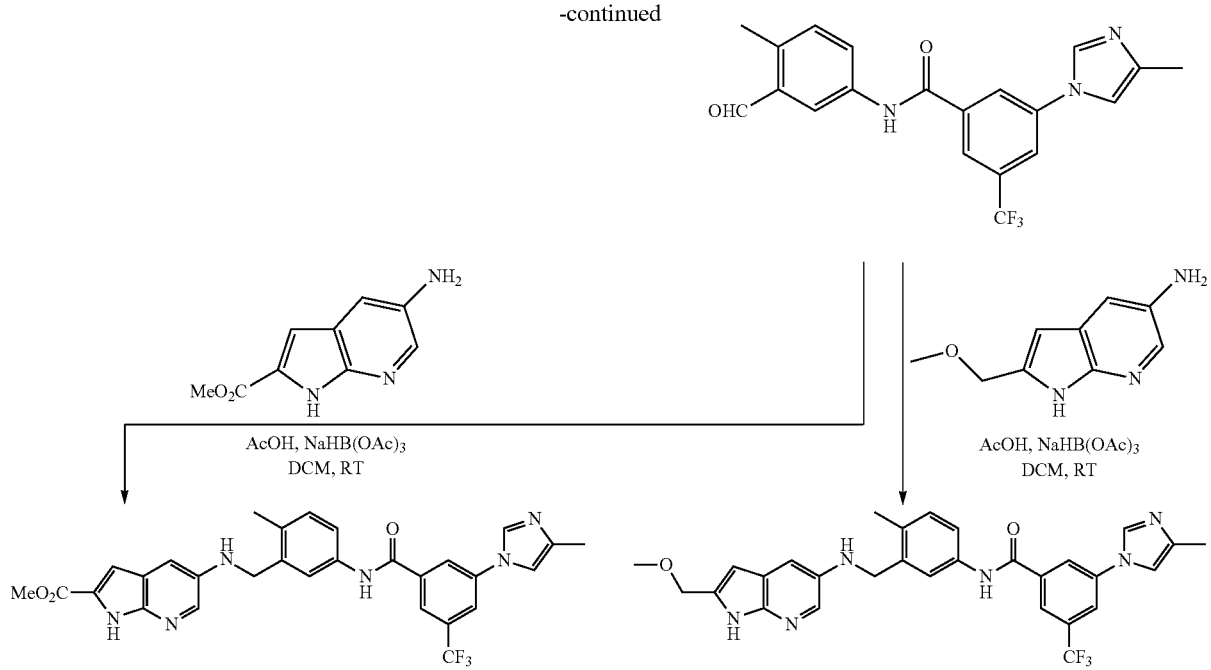

The method comprises at least the stages of:

a) peptidic coupling between methyl 5-amino-2-methyl-benzoate and 3-(trifluoromethyl)-5-(4-methyl-1H-imidazol-1-yl)benzoic acid (Ding, Qiang et al, WO2005039486);

b) reduction of the methylic ester into primary alcohol with lithium borohydride, c) oxidation of the alcohol into aldehyde with the Dess-Martin reagent, this stage is followed by step d or e d) reductive amination with methyl 5-amino-1H-pyrrolo[2,3-b]pyridine-2-carboxylate, e) reductive amination with 5-amino-2-methoxymethyl-1H-pyrrolo[2,3-b]pyridine.

The invention will be better understood on reading the following examples.

The compounds of the invention were obtained from methyl 5-nitro-1H-pyrrolo[2,3-b]pyridine-2-carboxylate (commercially available from the company Azasynth) in multi-stage synthesis, if necessary employing parallel synthesis apparatus ("Synthesis 1", Heidolph). The various synthesis protocols are detailed below together with the physicochemical characteristics of the compounds of the 7-azaindole type obtained.

The syntheses and analyses were carried out in the following conditions:

$^1$H and $^{13}$C Nuclear Magnetic Resonance:
Equipment:
Bruker Avance 300 (300 MHz); Bruker DPX 200 (200 MHz)
Conditions of Use:
Room temperature, chemical shifts expressed in parts per million (ppm), internal reference trimethylsilane (TMS), multiplicity of the signals indicated by lower-case letters (singlet s, doublet d, triplet t, quadruplet q, multiple m), dimethylsulphoxide $d_6$, methanol $d_4$, chloroform $d_1$ as deuterated solvents.

High-Performance Liquid Chromatography (HPLC):
Equipment:
Waters Alliance 2790 chromatographic system, UV 996 detector
Conditions of Use:
Thermo Hypersil $C_1$ column (50×2.1 mm), Water/Acetonitrile/Trifluoroacetic acid elution gradient (99.9%/0%/0.1% to 19.9%/80%/0.1%)
Mass Spectrometry (MS):
Equipment:
Micromass Q-T of
Conditions of Use:
ElectroSpray (ESI) in positive mode.
Weighings:
Equipment:
Denver Instrument TP214 (precision 0.1 mg)
Conditions of Use:
Weighings carried out to the nearest milligram.
Parallel Synthesis:
Equipment:
Heidolph Synthesis 1 (16 reactors)
Conditions of Use:
16 reactions in parallel, room temperature, multiple evaporation.
Reactions Under Pressure:
Equipment:
Parr 300 mL autoclave.
Conditions of Use:
Hydrogenation under 20 bar of hydrogen.

EXAMPLE A

Synthesis of Inhibitors in 2 Stages Starting from the Commercial Reagent From the Company Azasynth Scheme 10 represents a general method of synthesis of inhibitors of protein kinases.

Scheme 10 - General synthesis scheme of example A

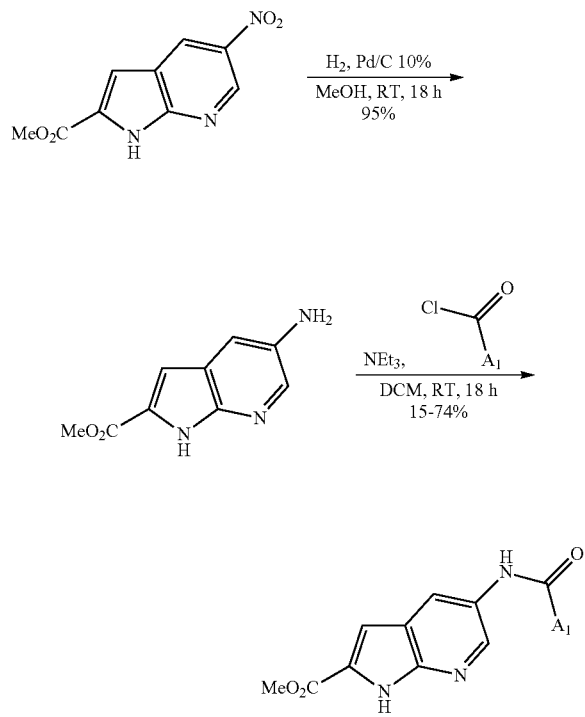

The first stage is a catalytic hydrogenation of methyl 5-nitro-1H-pyrrob[2,3-b]pyridine-2-carboxylate, in the presence of palladium on charcoal and under hydrogen atmosphere (Seela, F.; Gumbiowski, R., *Heterocycles* 1989, 29 (4), 795-805). The product is obtained at a raw yield of 95%. The second stage was carried out by parallel synthesis. The amine formed during the first stage is reacted with various acyl chlorides to give the corresponding amides at yields ranging from 15 to 74% after purification on silica gel (Mouaddib, A.; Joseph, B. et al., *Synthesis* 2000, (4), 549-556).

Stage 1: Preparation of methyl 5-amino-1H-pyrrolo[2,3-b]pyridine-2-carboxylate

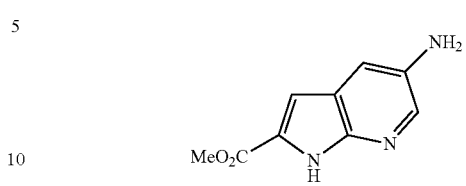

An autoclave is charged with 2.9 g (13.12 mmol) of methyl 5-nitro-1H-pyrrolo[2,3-b]pyridine-2-carboxylate (Azasynth), 290 mg of palladium on charcoal 10% and 200 mL of methanol. The reaction mixture is placed under 20 bar of hydrogen, and stirred for 18 h at room temperature. The solution is then filtered on Celite, and the Celite is rinsed with 3×100 mL of hot methanol. The filtrate is evaporated under reduced pressure. 2.38 g of a yellow solid is obtained at a yield of 95%.

$^1$H NMR (300 MHz, DMSO $d_6$): 11.98 (br s, 1H), 7.95 (d, 1H), 7.14 (d, 1H), 6.90 (s, 1H), 3.84 (s, 3H).

Stage 2: Preparation of the inhibitor starting from methyl 5-amino-1H-pyrrolo[2,3-b]pyridine-2-carboxylate A reactor is charged with 50 mg of methyl 5-amino-1H-pyrrolo[2,3-b]pyridine-2-carboxylate (0.26 mmol), the reagent (acyl chlorides) and 5 mL of dichloromethane. 56 µL (0.39 mmol) of triethylamine is added to the reaction mixture and it is stirred at room temperature for 18 hours. Then 60 mL of a saturated solution of sodium hydrogen carbonate is added to the reaction mixture. The precipitate that forms is filtered and rinsed with a little water. The filtrate is extracted with 3×50 ml of dichloromethane. The organic phases are combined, dried over sodium sulphate and evaporated under reduced pressure. A precipitate is obtained, which is combined with the filtered precipitate, then purified by silica gel chromatography (ethyl acetate/petroleum ether eluent).

Table 1 shows the various inhibitors synthesized according to the synthesis scheme described above.

TABLE 1

Inhibitors obtained by Example A

| Example No. | Reagents used | Inhibitors synthesized (mass and analytical data) |
|---|---|---|
| Example 1 ND0044 | cyclopropane-carbonyl chloride 26 µl (0.028 mmol) | Methyl 5-(cyclopropanecarboxamido)-1H-pyrrolo [2,3-b]pyridine-2-carboxylate<br><br>31 mg of a beige solid (46%);<br>$^1$H NMR (300 MHz, DMSO $d_6$): 12.43 (br s, 1H), 10.41 (br s, 1H), 8.48 (d, 1H), 8.41 (d, 1H), 7.14 (s, 1H), 3.87 (s, 3H), 1.81 (m, 1H), 0.87 (m, 4H);<br>HPLC: 97%; MS (ESI): 260.0 (M + 1) |

TABLE 1-continued

Inhibitors obtained by Example A

| Example No. | Reagents used | Inhibitors synthesized (mass and analytical data) |
|---|---|---|
| Example 2 ND0045 | 30 μL of isobutyryl chloride | Methyl 5-(isobutyramido)-1H-pyrrolo[2,3-b]pyridine-2-carboxylate 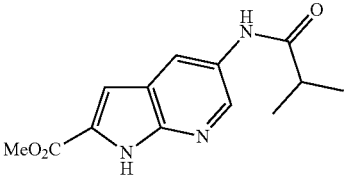 [SMILES: COC(=O)c1cc2cc(NC(=O)C(C)C)cnc2[nH]1] 38 mg beige solid (54%). HPLC: 97%. MS (ESI): 262.2 (M + 1) |
| Example 3 ND0046 | 25 μL or propionyl chloride | Methyl 5-(propionamido)-1H-pyrrolo[2,3-b]pyridine-2-carboxylate 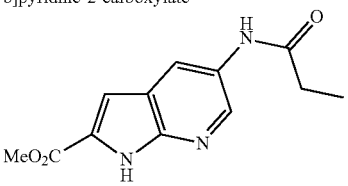 22 mg of white solid (54%). HPLC: 83%. MS (ESI): 247.2 (M + 1) |
| Example 4 ND0051 | 48 mg of 3-cyanobenzoyl chloride | Methyl 5-(3-cyanobenzamido)-1H-pyrrolo[2,3-b]pyridine-2-carboxylate 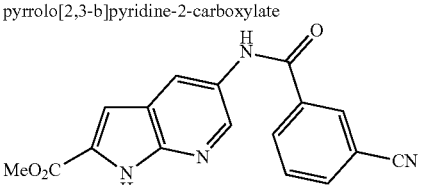 18 mg of yellow solid (22%). $^1$H NMR (300 MHz, DMSO d$_6$): 12.54 (br s, 1H), 10.67 (br s, 1H), 8.68 (d, 1H), 8.56 (d, 1H), 8.46 (s, 1H), 8.30 (m, 1H), 8.10 (m, 1H), 7.78 (m, 1H), 7.22 (s, 1H), 3.89 (s, 3H). HPLC: 96%. MS (ESI): 321.2 (M + 1) |
| Example 5 ND0053 | 45 mg of 3-fluorobenzoyl chloride | Methyl 5-(3-fluorobenzamido)-1H-pyrrolo[2,3-b]pyridine-2-carboxylate 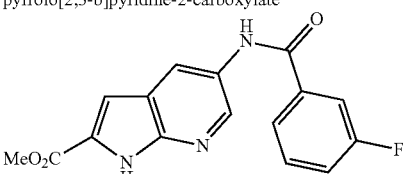 19 mg of yellow solid (23%). HPLC: 100%. MS (ESI): 314.2 (M + 1) |
| Example 6 ND0020 | 63 mg of 2-bromobenzoyl chloride | Methyl 5-(2-bromobenzamido)-1H-pyrrolo[2,3-b]pyridine-2-carboxylate 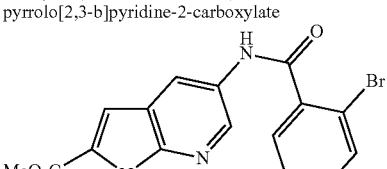 33 mg of beige solid (74%). $^1$H NMR (300 MHz, DMSO d$_6$): 12.52 (br s, 1H), 10.65 (br s, 1H), 8.58 (s, 2H), 7.74 (m, 1H), 7.62-7.41 (m, 3H), 7.22 (s, 1H), 3.89 (s, 3H). HPLC: 95%. MS (ESI): 373.8; 375.8 (M + 1) 338.2 (M + 1) |

TABLE 1-continued

Inhibitors obtained by Example A

| Example No. | Reagents used | Inhibitors synthesized (mass and analytical data) |
|---|---|---|
| Example 7 ND0061 | using 51 mg of 2,3-difluorobenzoyl chloride | Methyl 5-(2,3-difluorobenzamido)-1H-pyrrolo[2,3-b]pyridine-2-carboxylate 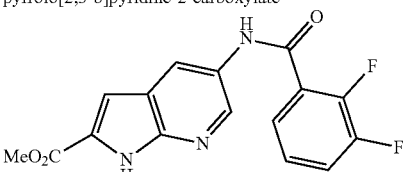 26 mg of beige solid (59%). $^1$H NMR (300 MHz, DMSO $d_6$): 12.61 (br s, 1H), 10.76 (br s, 1H), 8.65 (d, 1H), 8.62 (d, 1H), 7.75-7.58 (m, 2H), 7.48-7.35 (m, 1H), 7.28 (s, 1H), 3.95 (s, 3H). HPLC: 100%. MS (ESI): 332.2 (M + 1) |
| Example 8 ND0054 | 68 mg of 4-(2-methylthiazol-4-yl)benzoyl chloride | Methyl 5-(4-(2-methylthiazol-4-yl)benzamido)-1H-pyrrolo[2,3-b]pyridine-2-carboxylate 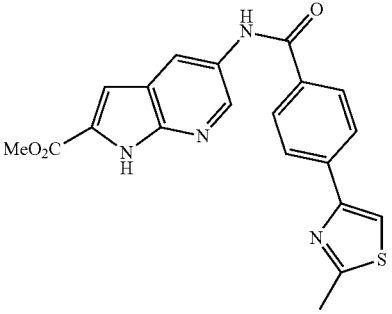 [SMILES: COC(=O)c1cc2cc(NC(=O)c3ccc(-c4csc(C)n4)cc3)cnc2[nH]1] 26 mg of beige solid (25%). HPLC: 75%. MS (ESI): 393.2 (M + 1) |
| Example 9 ND0062 | 52 mg of 2,3-dihydrobenzofuran-7-carbonyl chloride | Methyl 5-(2,3-dihydrobenzofuran-7-carboxamido)-1H-pyrrolo[2,3-b]pyridine-2-carboxylate 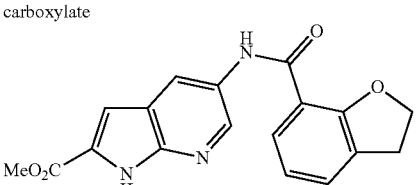 24 mg of brown solid (15%). HPLC: 100%. MS (ESI): 338.2 (M + 1) |
| Example 10 ND0047 | 54 mg of 2-fluoro-6-methoxybenzoyl chloride | Methyl 5-(2-fluoro-6-methoxybenzamido)-1H-pyrrolo[2,3-b]pyridine-2-carboxylate 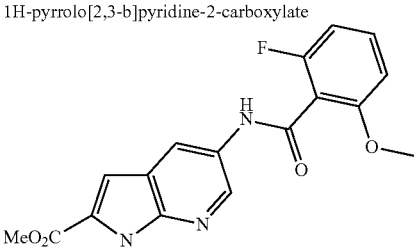 30 mg of white solid (33%). $^1$H NMR (300 MHz, DMSO $d_6$): 12.50 (br s, 1H), 10.47 (br s, 1H), 8.60 (d, 1H), 8.53 (d, 1H), 7.47 (m, 1H), 7.21 (s, 1H), 7.00-6.90 (m, 2H), 3.39 (s, 3H), 3.84 (s, 3H). HPLC: 99%. MS (ESI): 344.2 (M + 1) |

TABLE 1-continued

Inhibitors obtained by Example A

| Example No. | Reagents used | Inhibitors synthesized (mass and analytical data) |
|---|---|---|
| Example 11 ND0059 | 67 mg of 2-phenoxybenzoyl chloride | Methyl 5-(2-phenoxybenzamido)-1H-pyrrolo[2,3-b]pyridine-2-carboxylate 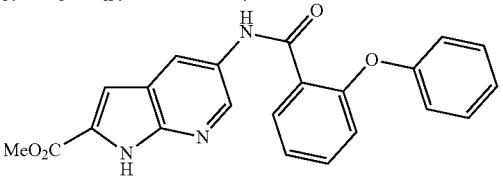 28 mg of brown solid (28%). HPLC: 91%. MS (ESI): 388.2 (M + 1) |
| Example 12 ND0050 | 51 mg of nicotinoyl chloride hydrochloride | Methyl 5-(nicotinamido)-1H-pyrrolo[2,3-b]pyridine-2-carboxylate 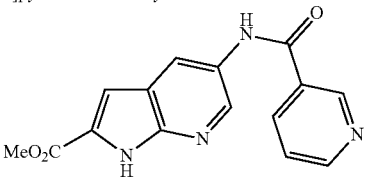 15 mg of brown solid (20%). HPLC: 100%. MS (ESI): 297.2 (M + 1) |
| Example 13 ND0060 | 62 mg of 2-(propylthio)pyridine-3-carbonyl chloride | Methyl 5-(2-(propylthio)pyridine-3-carboxamido)-1H-pyrrolo[2,3-b]pyridine-2-carboxylate 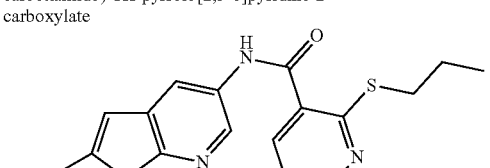 60 mg of beige solid (28%). HPLC: 98%. MS (ESI): 373.1 (M + 1) |
| Example 14 ND0063 | 45 μL of 2-(3-methoxyphenyl)-acetyl chloride | Methyl 5-(2-(3-methoxyphenyl)acetamido)-1H-pyrrolo[2,3-b]pyridine-2-carboxylate 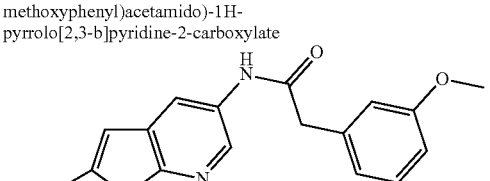 22 mg of beige solid (27%). HPLC: 100%. MS (ESI): 340.2 (M + 1) |
| Example 15 ND0064 | 43 μL of 2-(2-bromophenyl)-acetyl chloride | Methyl 5-(2-(2-bromophenyl)acetamido)-1H-pyrrolo[2,3-b]pyridine-2-carboxylate 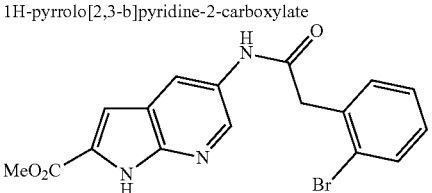 19 mg of brown solid (24%). HPLC: 93%. MS (ESI): 388.1; 390.1 (M + 1) |

TABLE 1-continued

Inhibitors obtained by Example A

| Example No. | Reagents used | Inhibitors synthesized (mass and analytical data) |
|---|---|---|
| Example 44 ND0072 | 2,6-dichlorobenzoyl chloride | Methyl 5-(2,6-dichlorobenzamido)-1H-pyrrolo[2,3-b]pyridine-2-carboxylate<br><br>12 mg of product (12%);<br>1H NMR (400 MHz, DMSO d6): 12.55 (br s, 1H), 10.92 (br s, 1H), 8.57 (d, 1H), 8.52 (d, 1H), 7.63-7.50 (m, 3H), 7.23 (s, 1H), 3.90 (s, 3H);<br>HPLC: 97%; MS: 365.9 (M + 1) |
| Example 45 ND0073 | 2-methoxybenzoyl chloride | Methyl 5-(2-methoxybenzamido)-1H-pyrrolo[2,3-b]pyridine-2-carboxylate<br><br>30 mg of product (35%);<br>1H NMR (400 MHz, DMSO d6): 12.48 (br s, 1H), 10.21 (br s, 1H), 8.6 (s, 2H), 7.69 (m, 1H), 7.52 (m, 1H), 7.21 (m, 2H), 7.09 (m, 1H), 3.92 (s, 3H), 3.88 (s, 3H);<br>HPLC: 97%; MS: 326.0 (M + 1) |
| Example 46 ND0074 | 2-chloro-6-methylbenzoyl chloride | Methyl 5-(2-chloro-6-methylbenzamido)-1H-pyrrolo[2,3-b]pyridine-2-carboxylate<br><br>10 mg of product (20%);<br>1H NMR (400 MHz, DMSO d6): 12.53 (br s, 1H), 10.70 (br s, 1H), 8.56 (m, 2H), 8.39 (m, 2H), 7.32 (m, 1H), 7.21 (s, 1H), 3.88 (s, 3H), 2.32 (s, 3H);<br>HPLC: 96%; MS: 343.6 (M + 1) |
| Example 47 ND0075 | 3-bromobenzoyl chloride | Methyl 5-(3-bromobenzamido)-1H-pyrrolo[2,3-b]pyridine-2-carboxylate<br><br>30 mg of product (30%);<br>1H NMR (400 MHz, DMSO d6): 12.50 (br s, 1H), 10.48 (br s, 1H), 8.65 (d, 1H), 8.54 (d, 1H), 8.19 (s, 1H), 8.00 (d, 1H), 7.82 (d, 1H), 7.53 (t, 1H), 7.21 (s, 1H), 3.90 (s, 3H);<br>HPLC: 95%; MS: 375.9 (M + 1) |

TABLE 1-continued

Inhibitors obtained by Example A

| Example No. | Reagents used | Inhibitors synthesized (mass and analytical data) |
|---|---|---|
| Example 48 ND0076 | 2-methylbenzoyl chloride | Methyl 5-(2-methylbenzamido)-1H-pyrrolo[2,3-b]pyridine-2-carboxylate<br>40 mg of product (49%);<br>1H NMR (400 MHz, DMSO d6): 12.50 (br s, 1H), 10.43 (br s, 1H), 8.60 (s, 2H), 7.52 (m, 1H), 7.41 (m, 1H), 7.32 (m, 2H), 7.20 (s, 1H), 3.91 (s, 3H);<br>HPLC: 95%; MS: 310.1 (M + 1) |
| Example 49 ND0077 | 2-(trifluoromethyl)benzoyl chloride | Methyl 5-(2-(trifluoromethyl)benzamido)-1H-pyrrolo[2,3-b]pyridine-2-carboxylate<br>20 mg of product (21%);<br>1H NMR (400 MHz, DMSO d6): 12.53 (br s, 1H), 10.68 (br s, 1H), 8.54 (s, 2H), 7.90-7.70 (m, 4H), 7.21 (s, 1H), 3.92 (s, 3H);<br>HPLC: 97%; MS: 364.0 (M + 1) |
| Example 50 ND0078 | 2-(trifluoromethoxy)benzoyl chloride | Methyl 5-(2-(trifluoromethoxy)benzamido)-1H-pyrrolo[2,3-b]pyridine-2-carboxylate<br>40 mg of product (40%);<br>1H NMR (400 MHz, DMSO d6): 12.52 (br s, 1H), 10.62 (br s, 1H), 8.55 (s, 2H), 7.78 (m, 1H), 7.67 (m, 1H), 7.54 (m, 2H), 7.22 (s, 1H), 3.90 (s, 3H);<br>HPLC: 98%; MS: 380.0 (M + 1) |
| Example 51 ND0079 | thiophene-2-carbonyl chloride | Methyl 5-(thiophene-2-carboxamido)-1H-pyrrolo[2,3-b]pyridine-2-carboxylate<br>30 mg of product (40%);<br>1H NMR (400 MHz, DMSO d6): 12.50 (br s, 1H), 10.40 (br s, 1H), 8.63 (d, 1H), 8.46 (d, 1H), 8.04 (d, 1H), 7.88 (d, 1H), 7.25 (t, 1H), 7.20 (s, 1H), 3.87 (s, 3H);<br>HPLC: 95%; MS: 302.1 (M + 1) |

EXAMPLE A1
Synthesis of Inhibitors in 2 Stages Starting from the Commercial Reagent From the Company Azasynth
Scheme 11 represents a general method of synthesis of inhibitors of protein kinases.
Scheme 11
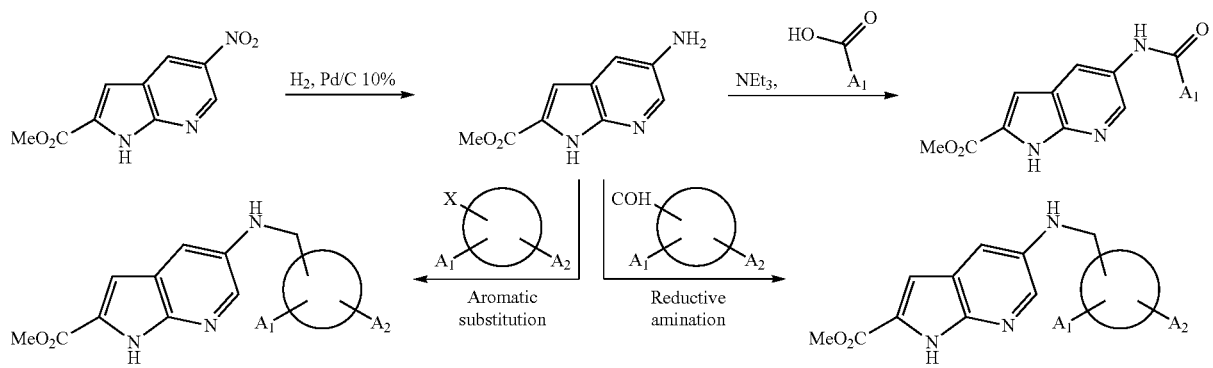
Wherein
represents an aryl or heteroaryl group.
In one embodiment
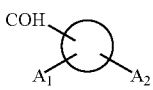
represents
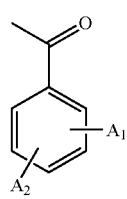
In one embodiment
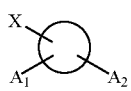
represents
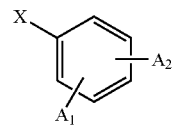
In one embodiment
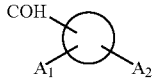
represents
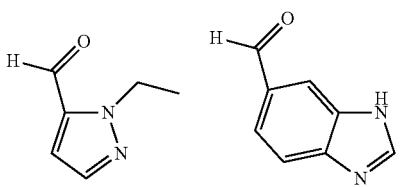
represents
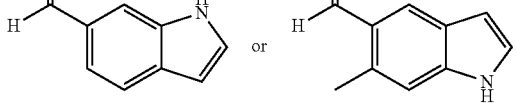

The first stage is a catalytic hydrogenation of methyl 5-nitro-1H-pyrrolo[2,3-b]pyridine-2-carboxylate, in the presence of palladium on charcoal and under hydrogen atmosphere (Seela, F.; Gumbiowski, R., *Heterocycles* 1989, 29 (4), 795-805). The product is obtained at a raw yield of 95%. The second stage was carried out by parallel synthesis and could be either the formation of amidoazaindol by peptidic coupling, or the formation of arylaminoazaindol or hétéroarylaminoazaindol by nucleophilic aromatic substitution, or the formation of, benzylaminoazaindol by reductive amination. The following examples will enable to better understand the invention.

The first stage is the same as in previous example A.

Option 1 Step 2: Preparation of the inhibitor starting from methyl 5-amino-1H-pyrrolo[2,3-b]pyridine-2-carboxylate with carboxylic acids (peptidic coupling)

A reactor is charged with 25 mg (0.13 mmol) of methyl 5-amino-1H-pyrrolo[2,3-b]pyridine-2-carboxylate, one equivalent of a carboxylic acid, 1.5 equivalents of hydroxybenzotriazole, 1.5 equivalents of N-(3-dimethylaminopropyl)-N'-ethylcarbodiimide hydrogen carbonate, 2 equivalents of N,N-diisopropylethylamine into 1 ml of dimethylformamide. The solution is mixed at room temperature for 12 hours. The solvent is then evaporated under reduced pressure and the raw product is purified directly on preparative HPLC.

The following table 2 regroups the inhibitor synthesized following this protocol.

TABLE 2

| Example No. | Reagents used | Inhibitors synthesized (mass and analytical data) |
|---|---|---|
| Example 52 ND0082 | (indole-5-carboxylic acid structure) | Methyl 5-(1H-indole-5-carboxamido)-1H-pyrrolo[2,3-b]pyridine-2-carboxylate<br><br>40 mg of product (91%);<br>$^1$H NMR (400 MHz, DMSO d$_6$): 12.45 (br s, 1H), 11.40 (br s, 1H), 10.25 (br s, 1H), 8.68 (d, 1H), 8.56 (d, 1H), 8.31 (s, 1H), 7.77 (m, 1H), 7.50 (m, 2H), 7.19 (s, 1H), 6.58 (s, 1H), 3.87 (s, 3H);<br>HPLC: 98%; MS: 335.2 (M + 1) |
| Example 53 ND0085 | (3-methyl-1H-pyrazole-5-carboxylic acid structure) | Methyl 5-(3-methyl-1H-pyrazole-5-carboxamido)-1H-pyrrolo[2,3-b]pyridine-2-carboxylate<br><br>20 mg of product (51%);<br>$^1$H NMR (400 MHz, DMSO d$_6$): 12.44 (br s, 1H), 10.18 (br s, 1H), 8.68 (d, 1H), 8.53 (d, 1H), 7.18 (s, 1H), 6.55 (s, 1H), 3.86 (s, 3H), 2.25 (s, 3H);<br>HPLC: 91%; MS: 300.2 (M + 1) |

TABLE 2-continued

| Example No. | Reagents used | Inhibitors synthesized (mass and analytical data) |
|---|---|---|
| Example 54 ND0086 | (3-carboxybenzenesulfonyl furfurylamide structure) | Methyl 5-(3-{[(2-furylmethyl)amino]sulfonyl}benzamido)-1H-pyrrolo[2,3-b]pyridine-2-carboxylate<br><br>(product structure)<br><br>15 mg of product (25%);<br>¹H NMR (400 MHz, DMSO d₆): 12.50 (br s, 1H), 10.62 (br s, 1H), 8.66 (d, 1H), 8.54 (d, 1H), 8.37 (s, 1H), 8.22 (d, 1H), 7.96 (d, 1H), 7.74 (t, 1H), 7.46 (s, 1H), 7.22 (s, 1H), 6.29 (d, 1H), 6.18 (d, 1H), 4.05 (s, 2H), 3.88 (s, 3H);<br>HPLC: 94%; MS: 455.1 (M + 1) |

Option 2: Step 2: General protocol for the preparation of benzylic acid by reductive amination A reactor is charged with 25 mg (0.13 mmol) of methyl 5-amino-1H-pyrrolo[2,3-b]pyridine-2-carboxylate, 1 equivalent of aldehyde and 1 ml of methanol, 1 equivalent of acetic acid is added and the reaction mixture is then mixed at room temperature for 2 hours. Once the Shiff base is confirmed by MS analysis, 1.5 equivalents of sodium cyanoborohydride is added and the mixture is then mixed at room temperature for 12 hours. The reacting medium is then purified by preparative HPLC.

The following table 3 regroups the inhibitor synthesized following this protocol.

TABLE 3

| Example No. | Reagents used | Inhibitors synthesized (mass and analytical data) |
|---|---|---|
| Example 55 ND0087 | (2,6-dichlorobenzaldehyde structure) | Methyl 5-(2,6-dichlorobenzylamino)-1H-pyrrolo[2,3-b]pyridine-2-carboxylate<br><br>(product structure)<br><br>15 mg of product (33%);<br>¹H NMR (400 MHz, DMSO d₆): 12.07 (br s, 1H), 8.09 (d, 1H), 7.52 (m, 2H), 7.39 (m, 1H), 7.24 (m, 1H), 6.95 (d, 1H), 5.71 (br s, 1H), 4.40 (s, 2H), 3.82 (s, 3H);<br>HPLC: 92%; MS: 352.1 (M + 1) |

TABLE 3-continued

| Example No. | Reagents used | Inhibitors synthesized (mass and analytical data) |
|---|---|---|
| Example 56 ND0088 | 2-methoxybenzaldehyde | Methyl 5-(2-methoxybenzylamino)-1H-pyrrolo[2,3-b]pyridine-2-carboxylate<br><br>30 mg of product (73%);<br>$^1$H NMR (400 MHz, DMSO d$_6$): 12.00 (br s, 1H), 8.05 (d, 1H), 7.30-7.18 (m, 2H), 7.08-6.85 (m, 4H), 6.02 (br s, 1H), 4.23 (s, 2H), 3.84 (s, 3H), 3.82 (s, 3H); HPLC: 92%; MS: 312.1 (M + 1) |
| Example 57 ND0089 | 2-chloro-6-methylbenzaldehyde | Methyl 5-(2-chloro-6-methylbenzylamino)-1H-pyrrolo[2,3-b]pyridine-2-carboxylate<br><br>25 mg of product (58%);<br>$^1$H NMR (400 MHz, DMSO d$_6$): 12.05 (br s, 1H), 8.09 (d, 1H), 7.36-7.20 (m, 4H), 6.95 (d, 1H), 5.58 (br s, 1H), 4.25 (s, 2H), 3.82 (s, 3H), 2.40 (s, 3H); HPLC: 92%; MS: 330.1 (M + 1) |
| Example 58 ND0057 | 2-bromobenzaldehyde | Methyl 5-(2-bromobenzylamino)-1H-pyrrolo[2,3-b]pyridine-2-carboxylate<br><br>20 mg of product (42%);<br>$^1$H NMR (400 MHz, DMSO d$_6$): 12.02 (br s, 1H), 8.09 (d, 1H), 7.64 (d, 1H), 7.42 (m, 1H), 7.33 (m, 1H), 7.21 (m, 1H), 6.92 (d, 1H), 6.89 (s, 1H), 6.46 (br s, 1H), 4.32 (s, 2H), 3.82 (s, 3H); HPLC: 94%; MS: 361.0 (M + 1) |

TABLE 3-continued

| Example No. | Reagents used | Inhibitors synthesized (mass and analytical data) |
| --- | --- | --- |
| Example 59 ND0090 | 2-methylbenzaldehyde | Methyl 5-(2-methylbenzylamino)-1H-pyrrolo[2,3-b]pyridine-2-carboxylate<br><br>15 mg of product (38%);<br>$^1$H NMR (400 MHz, DMSO $d_6$): 12.02 (br s, 1H), 8.08 (d, 1H), 7.31 (m, 1H), 7.22-7.08 (m, 3H), 7.01 (d, 1H), 6.89 (s, 1H), 5.99 (br s, 1H), 4.22 (s, 2H), 3.82 (s, 3H), 2.36 (s, 3H);<br>HPLC: 93%; MS: 296.2 (M + 1) |
| Example 60 ND0091 | 2-trifluoromethylbenzaldehyde | Methyl 5-(2-trifluoromethylbenzylamino)-1H-pyrrolo[2,3-b]pyridine-2-carboxylate<br><br>18 mg of product (39%);<br>$^1$H NMR (400 MHz, DMSO $d_6$): 12.02 (br s, 1H), 8.06 (d, 1H), 7.78 (m, 1H), 7.63 (m, 2H), 7.46 (m, 1H), 6.89 (m, 2H), 6.33 (br s, 1H), 4.45 (s, 2H), 3.81 (s, 3H);<br>HPLC: 95%; MS: 350.2 (M + 1) |
| Example 61 ND0092 | 2-(trifluoromethoxy)benzaldehyde | Methyl 5-(2-(trifluoromethoxy)benzamido)-1H-pyrrolo[2,3-b]pyridine-2-carboxylate<br><br>15 mg of product (31%);<br>$^1$H NMR (400 MHz, DMSO $d_6$): 12.22 (br s, 1H), 8.13 (d, 1H), 7.68 (m, 1H), 7.53 (m, 1H), 7.40 (m, 3H), 7.22 (m, 1H), 6.80 (br s, 1H), 4.43 (s, 2H), 3.88 (s, 3H);<br>HPLC: 96%; MS: 366.2 (M + 1) |

TABLE 3-continued

| Example No. | Reagents used | Inhibitors synthesized (mass and analytical data) |
|---|---|---|
| Example 62 ND0093 | thiophene-2-carbaldehyde | Methyl 5-((thiophen-2-yl)methylamino)-1H-pyrrolo[2,3-b]pyridine-2-carboxylate<br><br>25 mg of product (66%);<br>$^1$H NMR (400 MHz, DMSO $d_6$): 12.09 (br s, 1H), 8.04 (d, 1H), 7.37 (m, 1H), 7.17 (m, 1H), 7.09 (m, 1H), 6.97 (m, 1H), 6.92 (s, 1H), 6.20 (br s, 1H), 4.45 (s, 2H), 3.84 (s, 3H);<br>HPLC: 93%; MS: 288.1 (M + 1) |
| Example 63 ND0094 | thiazole-2-carbaldehyde | Methyl 5-((thiazol-2-yl)methylamino)-1H-pyrrolo[2,3-b]pyridine-2-carboxylate<br><br>15 mg of product (39%);<br>$^1$H NMR (400 MHz, DMSO $d_6$): 12.09 (br s, 1H), 8.32 (s, 1H), 8.07 (d, 1H), 7.76 (d, 1H), 7.59 (d, 1H), 7.07 (d, 1H), 6.91 (s, 1H), 6.55 (br s, 1H), 4.63 (s, 2H), 3.82 (s, 3H);<br>HPLC: 96%; MS: 289.0 (M + 1) |
| Example 64 ND0095 | 1H-imidazole-2-carbaldehyde | Methyl 5-((1H-imidazol-2-yl)methylamino)-1H-pyrrolo[2,3-b]pyridine-2-carboxylate<br><br>20 mg of product (39%);<br>$^1$H NMR (400 MHz, DMSO $d_6$): 12.05 (br s, 1H), 8.19 (d, 1H), 8.07 (d, 1H), 7.12 (d, 1H), 6.92 (m, 2H), 6.00 (br s, 1H), 4.25 (s, 2H), 3.82 (s, 3H);<br>HPLC: 95%; MS: 272.1 (M + 1) |

TABLE 3-continued

| Example No. | Reagents used | Inhibitors synthesized (mass and analytical data) |
|---|---|---|
| Example 65 ND0096 | 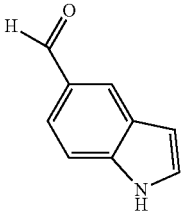 [SMILES: O=Cc1ccc2[nH]ccc2c1] | Methyl 5-((1H-indol-5-yl)methylamino)-1H-pyrrolo[2,3-b]pyridine-2-carboxylate<br>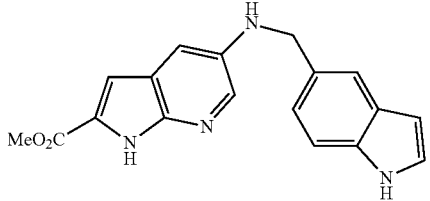<br>12 mg of product (28%);<br>$^1$H NMR (400 MHz, DMSO d$_6$): 11.98 (br s, 1H), 11.01 (br s, 1H), 8.08 (d, 1H), 7.54 (s, 1H), 7.31 (m, 2H), 7.13 (m, 1H), 7.03 (d, 1H), 6.86 (s, 1H), 6.36 (s, 1H), 6.10 (br s, 1H), 4.36 (s, 2H), 3.82 (s, 3H);<br>HPLC: 95%; MS: 321.2 (M + 1) |
| Example 66 ND0098 | 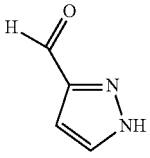 | Methyl 5-((1H-pyrazol-3-yl)methylamino)-1H-pyrrolo[2,3-b]pyridine-2-carboxylate<br>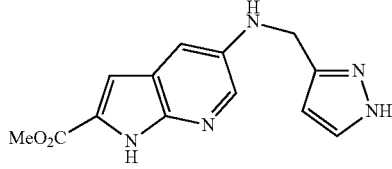<br>13 mg of product (36%);<br>$^1$H NMR (400 MHz, DMSO d$_6$): 12.60 (br s, 1H), 12.01 (br s, 1H), 8.06 (d, 1H), 7.60 (d, 1H), 7.14 (d, 1H), 6.88 (s, 1H), 6.21 (d, 1H), 5.89 (br s, 1H), 4.22 (s, 2H), 3.82 (s, 3H);<br>HPLC: 94%; MS: 272.1 (M + 1) |
| Example 67 ND0101 | 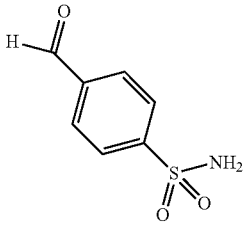 [SMILES: NS(=O)(=O)c1ccc(C=O)cc1] | Methyl 5-(3-(aminosulfonyl)benzylamino)-1H-pyrrolo[2,3-b]pyridine-2-carboxylate<br>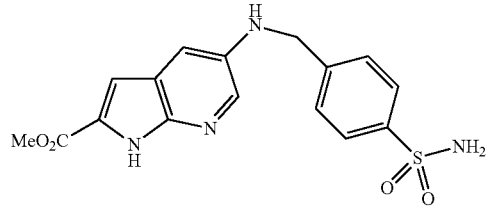<br>10 mg of product (21%);<br>$^1$H NMR (400 MHz, DMSO d$_6$): 12.02 (br s, 1H), 8.05 (d, 1H), 7.77 (d, 2H), 7.56 (d, 2H), 7.28 (br s, 2H), 6.97 (d, 1H), 6.87 (s, 1H), 6.33 (br s, 1H), 4.40 (s, 2H), 3.83 (s, 3H);<br>HPLC: 94%; MS: 361.2 (M + 1) |

TABLE 3-continued

| Example No. | Reagents used | Inhibitors synthesized (mass and analytical data) |
|---|---|---|
| Example 68 ND0133 | | Methyl 5-((1-ethyl-1H-pyrazol-5-yl)methylamino)-1H-pyrrolo[2,3-b]pyridine-2-carboxylate |
| Example 69 ND0134 | | Methyl 5-((1H-indol-6-yl)methylamino)-1H-pyrrolo[2,3-b]pyridine-2-carboxylate |
| Example 70 ND0135 | | Methyl 5-((6-methyl-1H-indol-5-yl)methylamino)-1H-pyrrolo[2,3-b]pyridine-2-carboxylate |
| Example 71 ND0139 | | Methyl 5-((1H-benzo[d]imidazol-6-yl)methylamino)-1H-pyrrolo[2,3-b]pyridine-2-carboxylate |
| Example 72 ND0140 | | Methyl 5-((5-methyl-1H-benzo[d]imidazol-6-yl)methylamino)-1H-pyrrolo[2,3-b]pyridine-2-carboxylate |

TABLE 3-continued

| Example No. | Reagents used | Inhibitors synthesized (mass and analytical data) |
|---|---|---|
| Example 73 ND0141 | (1H-pyrrolo[2,3-b]pyridine-5-carbaldehyde) | Methyl 5-((1H-pyrrolo[2,3-b]pyridin-5-yl)methylamino)-1H-pyrrolo[2,3-b]pyridine-2-carboxylate |

Option 3: Step 2: General Protocol for the Preparation of Aromatic Amine by Aromatic Substitution A reactor is charged with 25 mg (0.13 mmol) of methyl 5-amino-1H-pyrrolo[2,3-b]pyridine-2-carboxylate, 0.2 equivalents of copper iodide and 6 equivalents of potassium carbonate in 2 ml of dioxane. 1.5 equivalents of a halogenated reagent, 0.2 equivalents of trans-N,N-dimethylcyclohexane-1,2-diamine are then added and the mixture is stirred at 130-140° C. for 2 days. The reacting medium is then filtered on celite, evaporated and then purified by preparative HPLC to give the expected product. The following table 4 regroups the inhibitor synthesized following this protocol.

TABLE 4

| Example No. | Reagents used | Inhibitors synthesized (mass and analytical data) |
|---|---|---|
| Example 74 ND0102 | 1-iodo-3-methoxybenzene | Methyl 5-(3-methoxyphenylamino)-1H-pyrrolo[2,3-b]pyridine-2-carboxylate<br><br>28 mg of product (72%);<br>$^1$H NMR (400 MHz, CD$_3$OD): 7.94 (d, 1H), 7.43 (d, 1H), 7.38 (t, 1H), 7.21 (s, 1H), 7.03 (m, 1H), 6.90 (m, 1H), 6.86 (m, 1H), 3.83 (s, 3H), 3.74 (s, 3H);<br>HPLC: 96%; MS: 297.6 |
| Example 75 ND0103 | 1-bromo-3-iodobenzene | Methyl 5-(3-iodophenylamino)-1H-pyrrolo[2,3-b]pyridine-2-carboxylate<br><br>30 mg of product (58%);<br>$^1$H NMR (400 MHz, CDCl$_3$): 8.04 (d, 1H), 7.78 (m, 1H), 7.70 (m, 1H), 7.37 (m, 1H), 7.31 (d, 1H), 7.24 (s, 1H), 7.20 (m, 1H), 3.80 (s, 3H);<br>HPLC: 98%; MS: 393.5 |

TABLE 4-continued

| Example No. | Reagents used | Inhibitors synthesized (mass and analytical data) |
|---|---|---|
| Example 76 ND0058 | 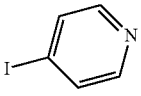 | Methyl 5-(pyridin-4-ylamino)-1H-pyrrolo[2,3-b]pyridine-2-carboxylate<br>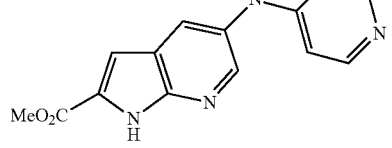<br>20 mg of product (57%);<br>$^1$H NMR (400 MHz, CD$_3$OD): 8.66 (m, 2H), 7.99 (d, 1H), 7.51 (m, 2H), 7.42 (d, 1H), 7.32 (s, 1H), 3.81 (s, 3H);<br>HPLC: 98%; MS: 268.6 |
| Example 77 ND0108 | 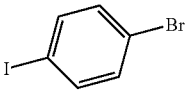 | Methyl 5-(4-iodophenylamino)-1H-pyrrolo[2,3-b]pyridine-2-carboxylate<br>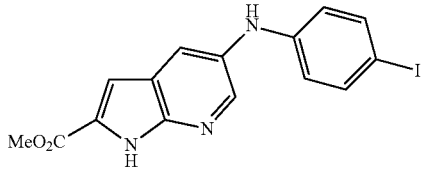<br>20 mg of product (39%);<br>$^1$H NMR (400 MHz, CDCl$_3$): 8.03 (d, 1H), 7.82 (d, 2H), 7.31 (d, 1H), 7.21 (s, 1H), 7.12 (d, 2H), 3.80 (s, 3H);<br>HPLC: 98%; MS: 393.5 |
| Example 78 ND0109 | 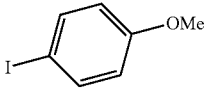 | Methyl 5-(4-methoxyphenylamino)-1H-pyrrolo[2,3-b]pyridine-2-carboxylate<br>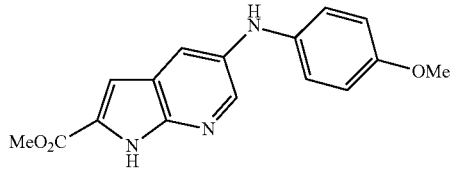<br>18 mg of product (46%);<br>$^1$H NMR (400 MHz, CDCl$_3$): 8.05 (s, 1H), 7.31 (d, 1H), 7.28 (d, 2H), 7.18 (s, 1H), 7.02 (d, 2H), 3.84 (s, 3H), 3.80 (s, 3H);<br>HPLC: 96%; MS: 298.0 |

TABLE 4-continued

| Example No. | Reagents used | Inhibitors synthesized (mass and analytical data) |
|---|---|---|
| Example 79 ND0113 | (4-iodo-N-methylbenzamide structure) | Methyl 5-(4-(methylcarbamoyl)phenylamino)-1H-pyrrolo[2,3-b]pyridine-2-carboxylate<br><br>17 mg of product (40%);<br>$^1$H NMR (400 MHz, DMSO d$_6$): 8.51 (s, 1H), 7.89 (m, 3H), 7.43 (m, 2H), 7.14 (m, 2H), 5.05 (br s, 2H), 6.36 (s, 1H), 3.71 (s, 3H), 2.80 (s, 3H);<br>HPLC: 91%; MS: 324.6 |
| Example 80 ND0104 | (1,3-dibromobenzene structure) | Methyl 5-(3-bromophenylamino)-1H-pyrrolo[2,3-b]pyridine-2-carboxylate<br><br>10 mg of product (22%);<br>$^1$H NMR (400 MHz, CDCl$_3$): 8.04 (d, 1H), 7.58 (m, 1H), 7.53 (m, 1H), 7.40-7.29 (m, 3H), 7.21 (s, 1H), 3.79 (s, 3H);<br>HPLC: 96%; MS: 347.0 |
| Example 81 ND0107 | (1-bromo-4-bromobenzene structure) | Methyl 5-(4-iodophenylamino)-1H-pyrrolo[2,3-b]pyridine-2-carboxylate<br><br>15 mg of product (33%);<br>$^1$H NMR (400 MHz, CDCl$_3$): 8.03 (d, 1H), 7.65 (d, 2H), 7.31 (d, 1H), 7.24 (d, 2H), 7.21 (s, 1H), 3.80 (s, 3H);<br>HPLC: 98%; MS: 347.0 |

EXAMPLE B

Synthesis of Inhibitors in 3 Stages Starting from the Inhibitor from Example 6

Scheme 12 shows the reaction scheme of Example B.

The first stage is selective reduction of the ester function by lithium aluminium hydride at room temperature to give the corresponding alcohol at a yield of 89% (Karrer, P., Boettcher, Augusta, *Helvetica Chimica Acta*, 1953, 36, 570-2). The alcohol formed is then converted to alkane bromide by PBr$_3$, at room temperature for 18 h in THF (raw yield of 81%) (Ku, Jin-Mo., J. et al., *Journal of Organic Chemistry*, 2007, 72 (21), 8115-8118). The intermediate alkane bromide is very reactive and cannot be purified without decomposition. When dissolved in methanol, it leads to the methoxyazaindole obtained by reaction of the solvent on the halogenated function, at room temperature (yield of 17%). To obtain the desired amines, the alkane bromide is therefore reacted directly without purification during the third and last stage. The latter is carried out by parallel synthesis using Heidolph's synthesis 1. Two equivalents of primary or secondary amine are added to the alkane bromide in anhydrous dimethylformamide, at room temperature for 18 h, to give the corresponding 7-azaindoles at yields ranging from 9 to 96% after purification on silica gel (Nagarathnam D., *Journal of Heterocyclic Chemistry*, 1992, 29 (6), 1371-3).

Scheme 12 - General synthesis scheme of Example B

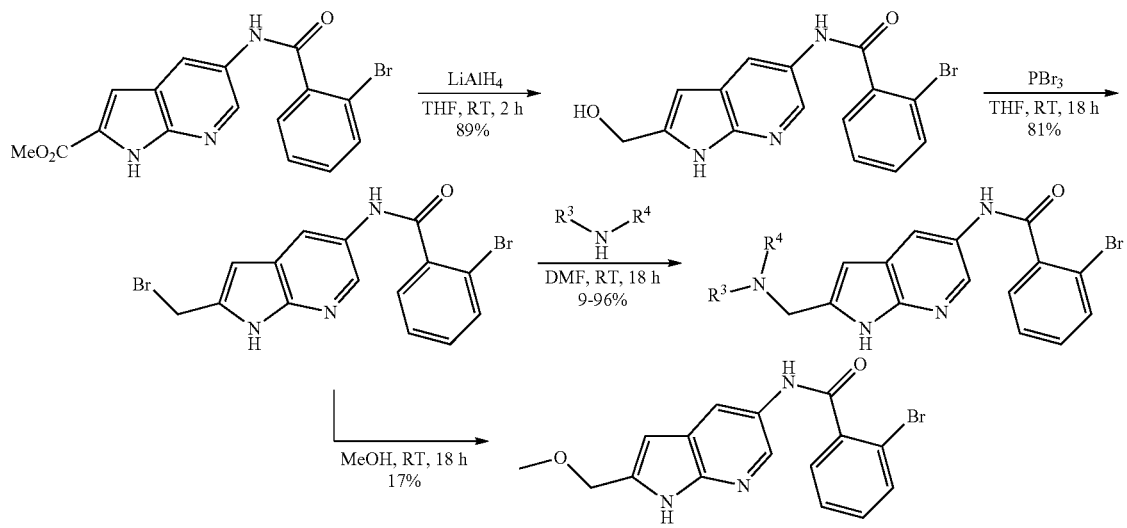

EXAMPLE 16

Preparation of 2-bromo-N-(2-(hydroxymethyl)-1H-pyrrolo[2,3-b]pyridin-5-yl)benzamide (ND0019)

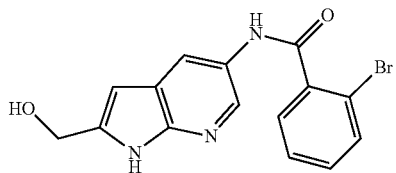 [SMILES: O=C(Nc1cnc2[nH]c(CO)cc2c1)c1ccccc1Br]

A flask is charged with 4.6 g (12.3 mmol) of methyl 5-(2-bromobenzamido)-1H-pyrrolo[2,3-b]pyridine-2-carboxylate (example 6) in 180 mL of anhydrous tetrahydrofuran under argon atmosphere. The reaction mixture is kept at 0° C. by means of a cold ethanol bath and 0.7 g (18.5 mmol) of lithium aluminium hydride in powder form is added cautiously, in several portions. It is stirred at 0° C., under argon, for 15 minutes and the cold bath is removed. The reaction mixture is stirred for a further 2 h, at room temperature. Then 3 mL of saturated aqueous ammonium chloride solution is added very slowly, and it is stirred for 15 min. The precipitate formed is then filtered on Celite, and the Celite is rinsed with 3×50 mL of hot tetrahydrofuran. The filtrate is evaporated under reduced pressure and 2.38 g of yellow solid is obtained (raw yield 95%).

$^1$H NMR (300 MHz, DMSO $d_6$): 11.50 (br s, 1H), 10.46 (br s, 1H), 8.34 (d, 1H), 8.28 (d, 1H), 7.80-7.37 (m, 5H), 6.32 (s, 1H), 5.30 (m, 1H), 4.60 (m, 2H)

HPLC: 95%. MS (ESI): 345.8; 347.8 (M+1).

Stage 1: Preparation of 2-bromo-N-(2-(bromomethyl)-1H-pyrrolo[2,3-b]pyridin-5-yl)benzamide

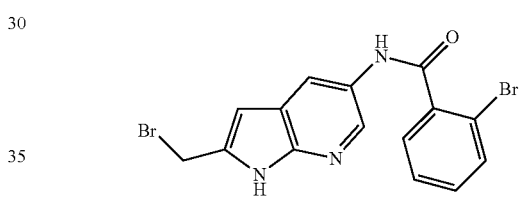

A flask is charged successively with 1 g (2.89 mmol) of 2-bromo-N-(2-(hydroxymethyl)-1H-pyrrolo[2,3-b]pyridin-5-yl)benzamide (Example 16), 100 mL of tetrahydrofuran and 408 μL (4.34 mmol) of phosphorus bromide (PBr$_3$) under argon atmosphere. It is stirred at room temperature for 18 hours. The solvent is then evaporated under reduced pressure, and the residue is taken up in 150 mL of ethyl acetate. The organic phase is washed with 3×50 mL of water, dried over sodium sulphate and evaporated under reduced pressure. The precipitate obtained is dried under vacuum for 1 h, finally obtaining 957 mg of a brown solid (raw yield 81%).

MS (ESI): 408.0; 410.0; 412.0 (M+1).

Stage 2: Preparation of the inhibitor from 2-bromo-N-(2-(bromomethyl)-1H-pyrrolo[2,3-b]pyridin-5-yl)benzamide A reactor is charged with 50 mg (0.12 mmol) of the 2-bromo-N-(2-(bromomethyl)-1H-pyrrolo[2,3-b]pyridin-5-yl)benzamide formed during the preceding stage, 0.5 mL of dimethylformamide (distilled on calcium hydride) and the reagent, under argon atmosphere. The solution is stirred at room temperature for 18 hours and then diluted in 30 mL of ethyl acetate, washed with 4×10 mL of water, dried over sodium sulphate and evaporated under reduced pressure. The raw product is then purified by silica gel chromatography (ethyl acetate/methanol eluent).

Table 5 shows the various inhibitors synthesized as a result of the second stage.

TABLE 5

Inhibitors obtained according to the synthesis scheme described in example B

| Example No. | Reagents used | Inhibitors synthesized (mass and analytical data) |
| --- | --- | --- |
| Example 17 ND0030 | 26 μL (0.24 mmol) of tert-butylamine | N-(2-((tert-butylamino)methyl)-1H-pyrrolo[2,3-b]pyridin-5-yl)-2-bromobenzamide<br>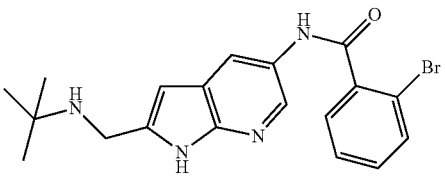<br>19 mg of a beige solid (49%).<br>$^1$H NMR (300 MHz, DMSO d$_6$): 11.44 (br s, 1H), 10.45 (br s, 1H), 8.32 (d, 1H), 8.24 (d, 1H), 7.74-7.40 (m, 4H), 6.30 (s, 1H), 3.82 (s, 2H), 1.11 (s, 9H).<br>HPLC: 97%.<br>MS (ESI): 401.1; 403.1 (M + 1). |
| Example 18 ND0023 | 22 μL of morpholine | 2-bromo-N-(2-(morpholinomethyl)-1H-pyrrolo[2,3-b]pyridin-5-yl)benzamide<br>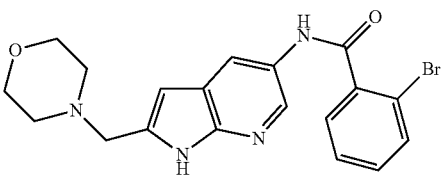<br>15 mg of white solid (57%).<br>$^1$H NMR (300 MHz, DMSO d$_6$): 11.56 (br s, 1H), 10.46 (br s, 1H), 8.35 (d, 1H), 8.27 (d, 1H), 7.75-7.40 (m, 4H), 6.33 (s, 1H), 3.62 (s, 2H), 3.61-3.58 (m, 4H), 2.44-2.42 (m, 4H).<br>HPLC: 95%.<br>MS (ESI): 415.1; 417.1 (M + 1). |
| Example 19 ND0024 | 36 μL of bis(2-methoxyethyl)amine | N-(2-((bis(2-methoxyethyl)amino)methyl)-1H-pyrrolo[2,3-b]pyridin-5-yl)-2-bromobenzamide<br>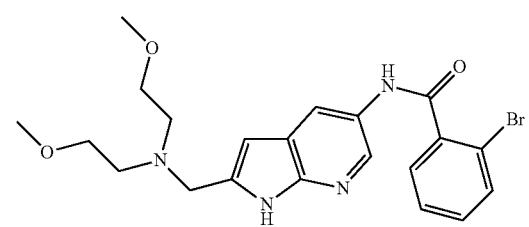<br>22 mg of white solid (55%).<br>$^1$H NMR (300 MHz, DMSO d$_6$): 11.42 (br s, 1H), 10.45 (br s, 1H), 8.34 (d, 1H), 8.25 (d, 1H), 7.75-7.40 (m, 4H), 6.32 (s, 1H), 3.81 (s, 2H), 3.44 (t, 4H), 3.23 (s, 6H), 2.70 (t, 4H).<br>HPLC: 97%.<br>MS (ESI): 461.2; 463.2 (M + 1). |

TABLE 5-continued

Inhibitors obtained according to the synthesis scheme described in example B

| Example No. | Reagents used | Inhibitors synthesized (mass and analytical data) |
|---|---|---|
| Example 20 ND0026 | 32 μL of 2-methyl cyclohexylamine (cis + trans mixture) | N-(2-((2-methylcyclohexylamino)methyl)-1H-pyrrolo[2,3-b]pyridin-5-yl)-2-bromobenzamide 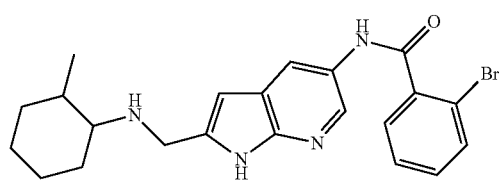<br>11 mg of beige solid (33%).<br>$^1$H NMR (300 MHz, DMSO d$_6$): 11.42 (br s, 1H), 10.44 (br s, 1H), 8.32 (d, 1H), 8.23 (d, 1H), 7.75-7.40 (m, 4H), 6.30 (s, 1H), 3.89-3.83 (m, 2H), 3.29-3.16 (m, 1H), 1.70-1.08 (m, 9H), 0.94-0.86 (m, 3H).<br>HPLC: 93%.<br>MS (ESI): 441.2; 443.2 (M + 1). |
| Example 21 ND0027 | 27 μL of 3-bromoaniline | N-(2-((3-bromophenylamino)methyl)-1H-pyrrolo[2,3-b]pyridin-5-yl)-2-bromobenzamide 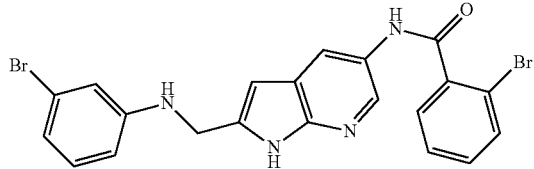<br>28 mg of beige solid (33%).<br>$^1$H NMR (300 MHz, DMSO d$_6$): 11.59 (br s, 1H), 10.46 (br s, 1H), 8.35 (d, 1H), 8.24 (d, 1H), 7.75-7.40 (m, 4H), 7.02 (br s, 1H), 6.82 (s, 1H), 6.70-6.63 (m, 2H), 6.46 (t, 1H), 6.34 (s, 1H), 4.40 (d, 2H).<br>HPLC: 96%.<br>MS (ESI): 499.0; 501.0; 503.0 (M + 1). |
| Example 22 ND0032 | 29 mg of 4-aminobenzonitrile | N-(2-((4-cyanophenylamino)methyl)-1H-pyrrolo[2,3-b]pyridin-5-yl)-2-bromobenzamide 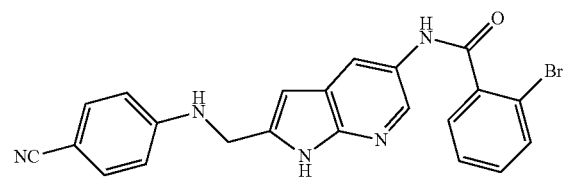<br>26 mg of white solid (49%).<br>$^1$H NMR (300 MHz, DMSO d$_6$): 11.64 (br s, 1H), 10.46 (br s, 1H), 8.36 (d, 1H), 8.25 (d, 1H), 7.74-7.39 (m, 6H), 7.17 (br s, 1H), 6.73 (d, 2H), 6.34 (s, 1H), 4.48 (d, 2H).<br>HPLC: 95%.<br>MS (ESI): 446.0; 448.1 (M + 1). |

TABLE 5-continued

Inhibitors obtained according to the synthesis scheme described in example B

| Example No. | Reagents used | Inhibitors synthesized (mass and analytical data) |
|---|---|---|
| Example 23 ND0036 | 29 mg of 2-aminobenzonitrile | N-(2-((2-cyanophenylamino)methyl)-1H-pyrrolo[2,3-b]pyridin-5-yl)-2-bromobenzamide 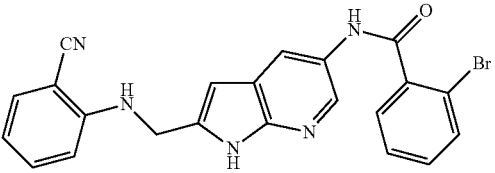 20 mg of white solid (44%). $^1$H NMR (300 MHz, DMSO $d_6$): 11.56 (br s, 1H), 10.45 (br s, 1H), 8.35 (d, 1H), 8.23 (d, 1H), 7.74-7.33 (m, 6H), 6.80 (m, 1H), 6.69-6.59 (m, 2H), 6.34 (s, 1H), 4.58 (d, 2H). HPLC: 95%. MS (ESI): 446.1; 448.1 (M + 1). |
| Example 24 ND0033 | 42 mg of 3-aminobenzene sulphonamide | N-(2-((3-sulphamidophenylamino)methyl)-1H-pyrrolo[2,3-b]pyridin-5-yl)-2-bromobenzamide  34 mg of white solid (66%). $^1$H NMR (300 MHz, DMSO $d_6$): 11.66 (br s, 1H), 10.52 (br s, 1H), 8.41 (d, 1H), 8.30 (d, 1H), 7.81-7.46 (m, 4H), 7.33-7.19 (m, 4H), 7.06 (d, 1H), 6.88 (m, 1H), 6.67 (br s, 1H), 6.40 (s, 1H), 4.51 (d, 2H). HPLC: 95%. MS (ESI): 500.1; 502.1 (M + 1). |
| Example 25 ND0034 | 34 mg of 3-nitroaniline | N-(2-((3-nitrophenylamino)methyl)-1H-pyrrolo[2,3-b]pyridin-5-yl)-2-bromobenzamide 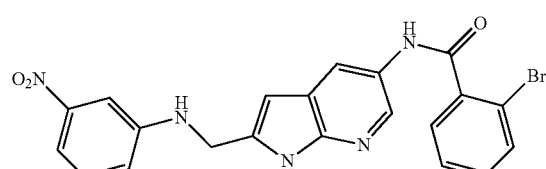 34 mg of yellow solid (69%). $^1$H NMR (300 MHz, DMSO $d_6$): 11.64 (br s, 1H), 10.46 (br s, 1H), 8.35 (d, 1H), 8.25 (d, 1H), 7.74-7.31 (m, 7H), 7.08 (m, 1H), 6.92 (br s, 1H), 6.36 (s, 1H), 4.50 (d, 2H). HPLC: 96%. MS (ESI): 466.1; 468.1 (M + 1). |

TABLE 5-continued

Inhibitors obtained according to the synthesis scheme described in example B

| Example No. | Reagents used | Inhibitors synthesized (mass and analytical data) |
|---|---|---|
| Example 26 ND0035 | 23 μL of aniline | N-(2-((phenylamino)methyl)-1H-pyrrolo[2,3-b]pyridin-5-yl)-2-bromobenzamide 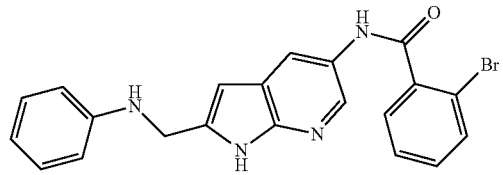 41 mg of white solid (87%). $^1$H NMR (300 MHz, DMSO d$_6$): 11.56 (br s, 1H), 10.44 (br s, 1H), 8.34 (d, 1H), 8.23 (d, 1H), 7.74-7.40 (m, 4H), 7.07 (t, 2H), 6.66 (d, 2H), 6.55 (t, 1H), 6.33 (s, 1H), 6.07 (br s, 1H), 4.39 (d, 2H). HPLC: 97%. MS (ESI): 421.1; 423.1 (M + 1). |
| Example 27 ND0040 | 26 μL of m-toluidine | N-(2-((m-toluidino)methyl)-1H-pyrrolo[2,3-b]pyridin-5-yl)-2-bromobenzamide 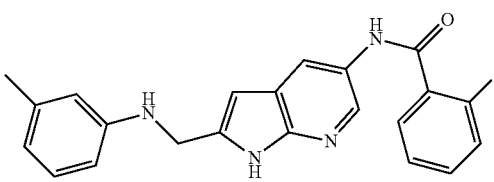 37 mg of yellow solid (79%). $^1$H NMR (300 MHz, DMSO d$_6$): 11.60 (br s, 1H), 10.50 (br s, 1H), 8.39 (d, 1H), 8.28 (d, 1H), 7.80-7.46 (m, 4H), 7.00 (t, 1H), 6.54-6.42 (m, 3H), 6.38 (s, 1H), 6.03 (br s, 1H), 4.44 (d, 2H), 2.23 (s, 3H). HPLC: 90%. MS (ESI): 435.1; 437.1 (M + 1). |
| Example 28 ND0038 | 27 mg of 4-aminophenol | N-(2-((4-hydroxyphenylamino)methyl)-1H-pyrrolo[2,3-b]pyridin-5-yl)-2-bromobenzamide 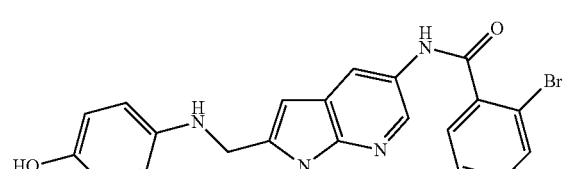 24 mg of brown solid (41%). $^1$H NMR (300 MHz, DMSO d$_6$): 11.51 (br s, 1H), 10.44 (br s, 1H), 8.44 (s, 1H), 8.33 (d, 1H), 8.22 (d, 1H), 7.74-7.40 (m, 4H), 6.53 (s, 4H), 6.32 (s, 1H), 5.43 (br s, 1H), 4.30 (d, 2H). HPLC: 81%. MS (ESI): 437.1; 439.1 (M + 1). |

TABLE 5-continued

Inhibitors obtained according to the synthesis scheme described in example B

| Example No. | Reagents used | Inhibitors synthesized (mass and analytical data) |
|---|---|---|
| Example 29 ND0041 | 27 µL of m-anisidine | N-(2-((3-methoxyphenylamino)methyl)-1H-pyrrolo[2,3-b]pyridin-5-yl)-2-bromobenzamide 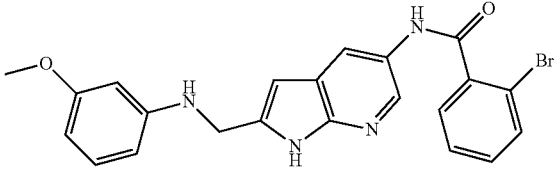 34 mg of beige solid (71%). $^1$H NMR (300 MHz, DMSO d$_6$): 11.55 (br s, 1H), 10.45 (br s, 1H), 8.34 (d, 1H), 8.23 (d, 1H), 7.74-7.40 (m, 4H), 6.97 (t, 1H), 6.33 (s, 1H), 6.28-6.08 (m, 4H), 4.38 (d, 2H), 3.65 (s, 3H). HPLC: 95%. MS (ESI): 451.1; 453.1 (M + 1) |
| Example 30 ND0029 | 23 mg of 4-aminopyridine | N-(2-((pyridin-4-ylamino)methyl)-1H-pyrrolo[2,3-b]pyridin-5-yl)-2-bromobenzamide 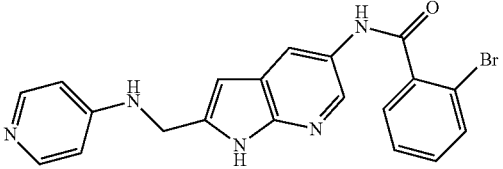 30 mg of brown solid (67%). HPLC: 100%. MS (ESI): 422.0; 424.1 (M + 1) |
| Example 31 ND0037 | 17 µL of pyrrole | N-(2-((1H-pyrrol-2-yl)methyl)-1H-pyrrolo[2,3-b]pyridin-5-yl)-2-bromobenzamide 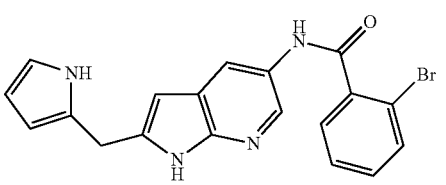 28 mg of black solid (66%). $^1$H NMR (300 MHz, DMSO d$_6$): 11.50 (br s, 1H), 10.66 (br s, 1H), 10.43 (br s, 1H), 8.32 (d, 1H), 8.20 (d, 1H), 7.74-7.40 (m, 4H), 6.64 (m, 1H), 6.11 (s, 1H), 5.93 (m, 1H), 5.85 (m, 1H), 4.02 (s, 2H). HPLC: 84%. MS (ESI): 395.1; 397.1 (M + 1). |

TABLE 5-continued

Inhibitors obtained according to the synthesis scheme described in example B

| Example No. | Reagents used | Inhibitors synthesized (mass and analytical data) |
|---|---|---|
| Example 32 ND0031 | 17 mg of imidazole | N-(2-((1H-imidazol-1-yl)methyl)-1H-pyrrolo[2,3-b]pyridin-5-yl)-2-bromobenzamide 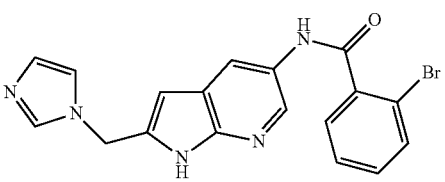 15 mg of yellow solid (42%). $^1$H NMR (300 MHz, DMSO d$_6$): 11.84 (br s, 1H), 10.50 (br s, 1H), 8.40 (d, 1H), 8.32 (d, 1H), 7.77-7.40 (m, 6H), 7.26 (s, 1H), 6.36 (s, 1H), 5.34 (s, 2H). HPLC: 80%. MS (ESI): 396.0; 398.1 (M + 1). |
| Example 33 ND0025 | 25 µL of (R)-tetrahydrofurfuryl amine | N-(2-((R)-tetrahydrofuran-2-yl)methyl)-1H-pyrrolo[2,3-b]pyridin-5-yl)-2-bromobenzamide 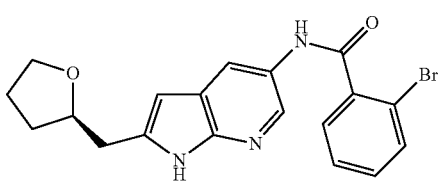 12 mg of yellow solid (32%). $^1$H NMR (300 MHz, DMSO d$_6$): 11.47 (br s, 1H), 10.46 (br s, 1H), 8.33 (d, 1H), 8.25 (d, 1H), 7.74-7.40 (m, 4H), 6.30 (s, 1H), 3.87 (m, 1H), 3.76-3.69 (m, 1H), 3.64-3.56 (m, 1H), 2.55 (d, 2H), 1.95-1.73 (m, 3H), 1.57-1.44 (m, 1H). HPLC: 93%. MS (ESI): 429.1; 431.1 (M + 1). |
| Example 34 ND0028 | 27 µL of benzylamine | N-(2-(benzylamino)methyl)-1H-pyrrolo[2,3-b]pyridin-5-yl)-2-bromobenzamide 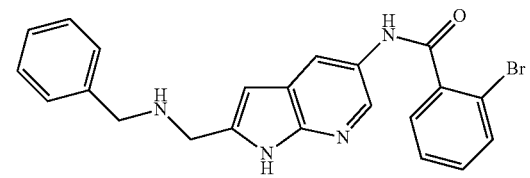 30 mg of white solid (57%). $^1$H NMR (300 MHz, DMSO d$_6$): 11.52 (br s, 1H), 10.51 (br s, 1H), 8.39 (d, 1H), 8.32 (d, 1H), 7.81-7.27 (m, 9H), 6.39 (s, 1H), 3.88 (s, 2H), 3.77 (s, 2H). HPLC: 98%. MS (ESI): 435.1; 437.1 (M + 1) |

EXAMPLE 35

Preparation of 2-bromo-N-(2-(methoxymethyl)-1H-pyrrolo[2,3-b]pyridin-5-yl)benzamide (ND0021)

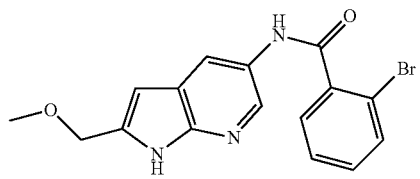 [SMILES: COCc1cc2cc(NC(=O)c3ccccc3Br)cnc2[nH]1]

A flask is charged with 200 mg (0.49 mmol) of 2-bromo-N-(2-(bromomethyl)-1H-pyrrolo[2,3-b]pyridin-5-yl)benzamide (stage 1) and 5 mL of methanol. The solution is stirred at room temperature for 18 hours and then diluted in 100 mL of ethyl acetate, washed with 3×30 mL of water, dried over sodium sulphate and evaporated under reduced pressure. The raw product is then purified by silica gel chromatography (ethyl acetate/petroleum ether eluent). 30 mg of a yellow solid is obtained (17%).

$^1$H NMR (300 MHz, DMSO $d_6$): 11.75 (br s, 1H), 10.54 (br s, 1H), 8.43 (d, 1H), 8.38 (d, 1H), 7.80-7.45 (m, 4H), 6.47 (s, 1H), 4.58 (s, 2H), 3.36 (s, 3H).

HPLC: 96%. MS (ESI): 360.1; 362.1 (M+1).

EXAMPLE 36

Preparation of (5-(2-bromobenzamido)-1H-pyrrolo[2,3-b]pyridin-2-yl)methyl quinoxaline-6-carboxylate (ND0022)

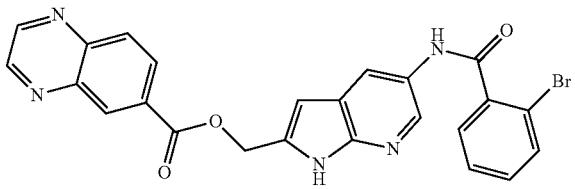 [SMILES: O=C(OCc1cc2cc(NC(=O)c3ccccc3Br)cnc2[nH]1)c1ccc2nccnc2c1]

A flask is charged successively with 50 mg (0.14 mmol) of 2-bromo-N-(2-(hydroxymethyl)-1H-pyrrolo[2,3-b]pyridin-5-yl)benzamide AT2-2BF2 (example 16), 5 mL of dichloromethane, 30 mg (0.15 mmol) of 6-quinoxalinecarbonyl chloride and 30 µL (0.22 mmol) of triethylamine. The solution is stirred at room temperature for 18 hours and then diluted in 60 mL of ethyl acetate, washed with 10 mL of saturated solution of sodium bicarbonate, 10 mL of water, and 10 mL of saturated solution of sodium chloride. The organic phase is then dried over sodium sulphate and evaporated under reduced pressure. The raw product is then purified by silica gel chromatography (ethyl acetate/petroleum ether eluent). 14 mg of a yellow solid is obtained (24%).

$^1$H NMR (300 MHz, DMSO $d_6$): 12.00 (br s, 1H), 10.53 (br s, 1H), 9.10 (s, 2H), 8.77 (s, 1H), 8.45-8.24 (m, 4H), 7.76-7.41 (m, 4H), 6.66 (s, 1H), 5.59 (s, 2H).

HPLC: 97%. MS (ESI): 502.1; 504.1 (M+1).

EXAMPLE C

Synthesis of inhibitors in 5 stages starting from methyl 5-nitro-1H-pyrrolo[2,3-b]pyridine-2-carboxylate (Scheme 13)

In the first stage, the ester is saponified with lithium hydroxide to give the corresponding carboxylic acid at a raw yield of 52% (Kanth, Sribhashyam R. et al., *Heterocycles*, 2005, 65 (6), 1415-1423). This carboxylic acid is then converted to amide by peptide coupling using N-(3-dimethylaminopropyl)-N'-ethylcarbodiimide (EDCl) hydrochloride and morpholine. The amide obtained is then hydrogenated with catalytic palladium, leading quantitatively to the corresponding aminoazaindole. The latter is then reacted with various acyl chlorides, in the presence of triethylamine in dimethylformamide, to obtain the desired 7-azaindoles.

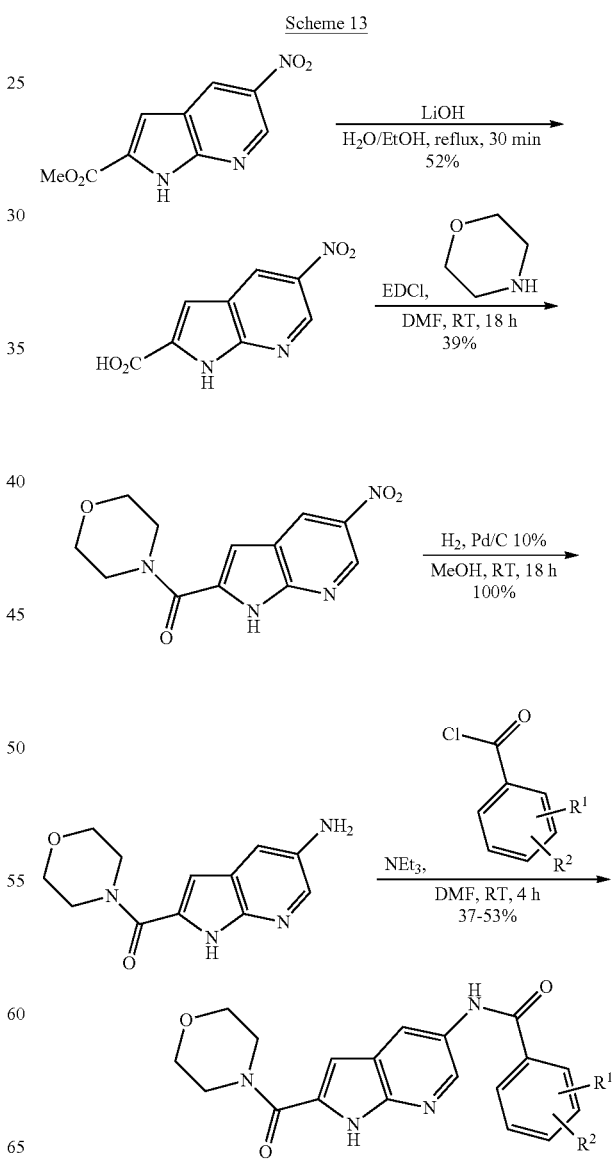

Scheme 13

EXAMPLE 37

Synthesis of 5-(2-fluoro-5-nitrobenzamido)-2-morpholinocarbonyl-1H-pyrrolo[2,3-b]pyridine (ND0010)

Stage 1: Preparation of 5-nitro-1H-pyrrolo[2,3-b]pyridine-2-carboxylic acid

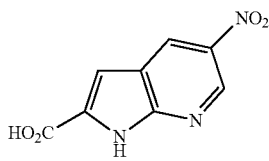 [SMILES: O=C(O)c1cc2cc([N+](=O)[O-])cnc2[nH]1]

A flask is charged successively with 5 g (22.62 mmol) of methyl 5-nitro-1H-pyrrolo[2,3-b]pyridine-2-carboxylate (Azasynth), 50 mL of 95% ethanol, 50 mL of water and 1.63 g (67.92 mmol) of lithium hydroxide. The reaction mixture is refluxed for 30 minutes and then left to return to room temperature. The solution is concentrated under reduced pressure and then diluted in 200 mL of water. The aqueous phase is extracted with 3×60 mL of ethyl acetate, then acidified with 32% hydrochloric acid until the pH is between 2 and 3. The precipitate formed is filtered, rinsed with 50 mL of ethyl acetate and then dried under vacuum for 6 h. 2.45 g of a white solid is obtained (52%).

$^1$H NMR (300 MHz, DMSO d$_6$): 13.60 (br s, 1H), 13.20 (br s, 1H), 9.25 (d, 1H), 9.26 (d, 1H), 7.38 (s, 1H).

Stage 2: Preparation of morpholino(5-nitro-1H-pyrrolo[2,3-b]pyridin-2-yl)methanone

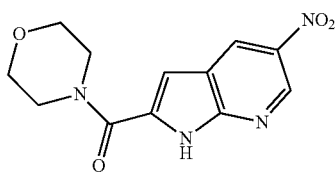 [SMILES: O=C(c1cc2cc([N+](=O)[O-])cnc2[nH]1)N1CCOCC1]

A flask is charged successively with 600 mg (2.90 mmol) of the 5-nitro-1H-pyrrolo[2,3-b]pyridine-2-carboxylic acid formed during the preceding stage, 10 mL of dimethylformamide (distilled on calcium hydride), 0.5 mL (5.80 mmol) of morpholine and 1.11 g (5.80 mmol) of N-(3-dimethylaminopropyl)-N'-ethylcarbodiimide (EDCl) hydrochloride under argon atmosphere. The solution is stirred at room temperature for 18 hours. The solvent is then evaporated under reduced pressure and the raw product is purified directly by silica gel chromatography (ethyl acetate/methanol eluent). 313 mg of a white solid is recovered (39%).

$^1$H NMR (300 MHz, DMSO d$_6$): 13.04 (br s, 1H), 9.20 (d, 1H), 8.97 (d, 1H), 7.05 (s, 1H), 3.70 (m, 8H).

Stage 3: Preparation of (5-amino-1H-pyrrolo[2,3-b]pyridin-2-yl)(morpholino)methanone

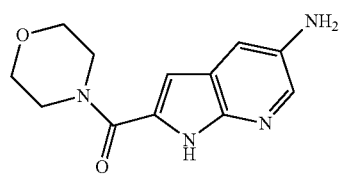 [SMILES: Nc1cnc2[nH]c(C(=O)N3CCOCC3)cc2c1]

An autoclave is charged with 313 mg (1.13 mmol) of the morpholino(5-nitro-1H-pyrrolo[2,3-b]pyridin-2-yl)methanone formed during the preceding stage, 100 mL of methanol and 31 mg of palladium on charcoal at 10%. The autoclave is placed under 20 bar of hydrogen and the solution is stirred at room temperature for 18 hours. The solution is then filtered on Celite, the Celite is rinsed with 50 mL of methanol and the filtrate is evaporated under reduced pressure. 280 mg of a white solid is recovered, and is used in the next stage without further purification (quantitative raw yield).

$^1$H NMR (300 MHz, DMSO d$_6$): 11.60 (br s, 1H), 7.86 (d, 1H), 7.13 (d, 1H), 6.52 (s, 1H), 4.84 (br s, 2H), 3.68 (m, 8H).

Stage 4: Preparation of 5-(2-fluoro-5-nitrobenzamido)-2-morpholinocarbonyl-1H-pyrrolo[2,3-b]pyridine ND0010)

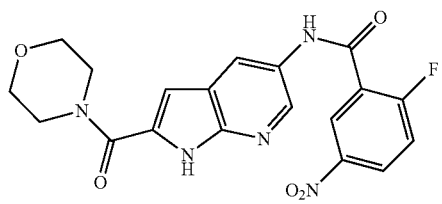 [SMILES: O=C(Nc1cnc2[nH]c(C(=O)N3CCOCC3)cc2c1)c1cc([N+](=O)[O-])ccc1F]

A flask is charged successively with 100 mg (0.40 mmol) of H-pyrrolo[2,3-b]pyridin-2-yl)(morpholino)methanone formed during the preceding stage, 5 mL of dimethylformamide (distilled on calcium hydride), 90 mg (0.44 mmol) of 2-fluoro-5-nitrobenzoyl chloride and 85 μL (0.60 mmol) of triethylamine under argon atmosphere. The solution is stirred at room temperature for 4 hours. The solvent is evaporated under reduced pressure and the residue is taken up in 100 mL of ethyl acetate. The organic phase is rinsed with 30 mL of saturated solution of sodium bicarbonate, 30 mL of water and 30 mL of saturated solution of sodium chloride. The organic phase is dried over sodium sulphate and evaporated under reduced pressure. The raw product obtained is purified by silica gel chromatography (ethyl acetate/methanol eluent), obtaining 90 mg of yellow solid (53%).

$^1$H NMR (300 MHz, DMSO d$_6$): 12.12 (br s, 1H), 10.30 (br s, 1H), 8.51-8.43 (m, 2H), 8.41 (d, 1H), 8.36 (d, 1H), 7.85 (m, 1H), 6.81 (s, 1H), 3.673 (m, 8H).

HPLC: 74%. MS (ESI): 414.3 (M+1).

EXAMPLE D

Synthesis of the inhibitor example 38 (ND0005)

5-(3-Fluorobenzamido)-1H-pyrrolo[2,3-b]pyridine-2-carboxamide (Scheme 12) was obtained in 3 stages (General scheme 14) starting from methyl 5-nitro-1H-pyrrolo[2,3-b]pyridine-2-carboxylate (Azasynth). The methyl ester of the azaindole is converted directly to primary amide by reaction of aqueous ammonia on the ester function (Ramasamy, K. et al., *Tetrahedron*, 1986, 42 (21), 5869-78). The reaction is conducted at room temperature for 24 h and the expected product is obtained at a yield of 10% after purification. The nitroazaindole thus obtained is hydrogenated, giving the corresponding aminoazaindole quantitatively. The latter leads to the compound of example 38 (ND0005) by reaction of the amine function on 3-fluorobenzoyl chloride, in dimethylformamide in the presence of triethylamine.

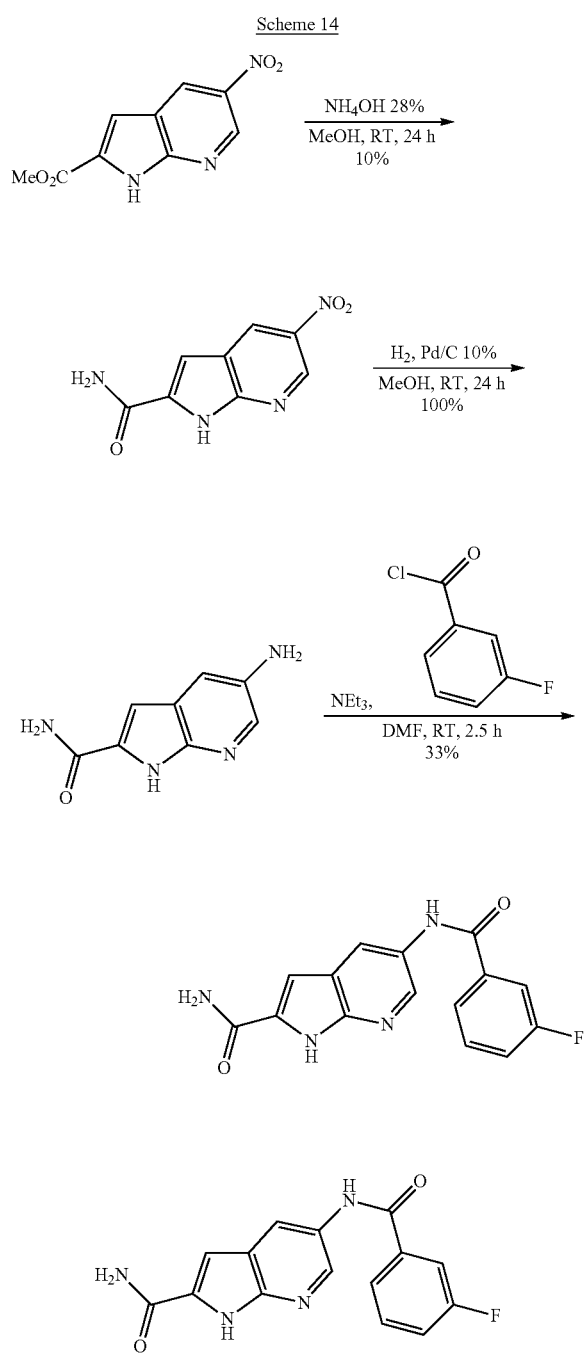

Scheme 14

A flask is charged with 300 mg (1.36 mmol) of methyl 5-nitro-1H-pyrrolo[2,3-b]pyridine-2-carboxylate (Azasynth), 7.5 mL of methanol and 15 mL of 28% ammonia solution. The reaction mixture is stirred at room temperature for 24 hours. The solution is concentrated under reduced pressure and then diluted with 100 mL of saturated solution of sodium chloride. The aqueous phase is extracted with 3×30 mL of ethyl acetate. The organic phases are combined, dried over sodium sulphate and evaporated under reduced pressure. The raw product obtained is purified by silica gel chromatography (ethyl acetate/petroleum ether eluent). 30 mg of a yellow solid is obtained (10%).

An autoclave is charged with 30 mg (0.14 mmol) of the 5-nitro-1H-pyrrolo[2,3-b]pyridine-2-carboxamide that formed previously, 100 mL of methanol and 10 mg of palladium on charcoal at 10%. The autoclave is placed under 20 bar of hydrogen and the solution is stirred at room temperature for 2 hours. The solution is then filtered on Celite. The Celite is rinsed with 50 mL of methanol and the filtrate is evaporated under reduced pressure. 25 mg of a yellow solid is recovered, and is used in the next stage without further purification (quantitative raw yield).

A flask is charged successively with 25 mg (0.14 mmol) of the 5-amino-1H-pyrrolo[2,3-b]pyridine-2-carboxamide that formed previously, 3 mL of dimethylformamide (distilled on calcium hydride), 19 μL (0.16 mmol) of 3-fluorobenzoyl chloride and 30 μL (0.21 mmol) of triethylamine under argon atmosphere. The solution is stirred at room temperature for 2.5 hours. The solvent is evaporated under reduced pressure and the residue is taken up in 100 mL of saturated solution of sodium bicarbonate. The aqueous phase is extracted with 3×30 mL of ethyl acetate. The organic phases are combined, dried over sodium sulphate and evaporated under reduced pressure. The raw product obtained is purified by silica gel chromatography (ethyl acetate eluent), obtaining 14 mg of beige solid (33%).

$^1$H NMR (300 MHz, DMSO $d_6$): 12.04 (br s, 1H), 10.44 (br s, 1H), 8.57 (d, 1H), 8.45 (d, 1H), 7.98 (br s, 2H), 7.89-7.43 (m, 4H), 7.12 (s, 1H).

HPLC: 56%. MS (ESI): 299.2 (M+1).

EXAMPLE E

Synthesis of inhibitors starting from methyl 5-amino-1H-pyrrolo[2,3-b]pyridine-2-carboxylate Scheme 15 shows the general synthesis scheme.

The aminoazaindole is converted to amides by reacting different acyl chlorides on the amine function. The amides thus obtained are saponified by the action of potassium hydroxide under reflux in a water-methanol mixture, and lead to the compounds described in examples 39 to 43 by reacting the acid function on various alcohols and amines.

Scheme 15

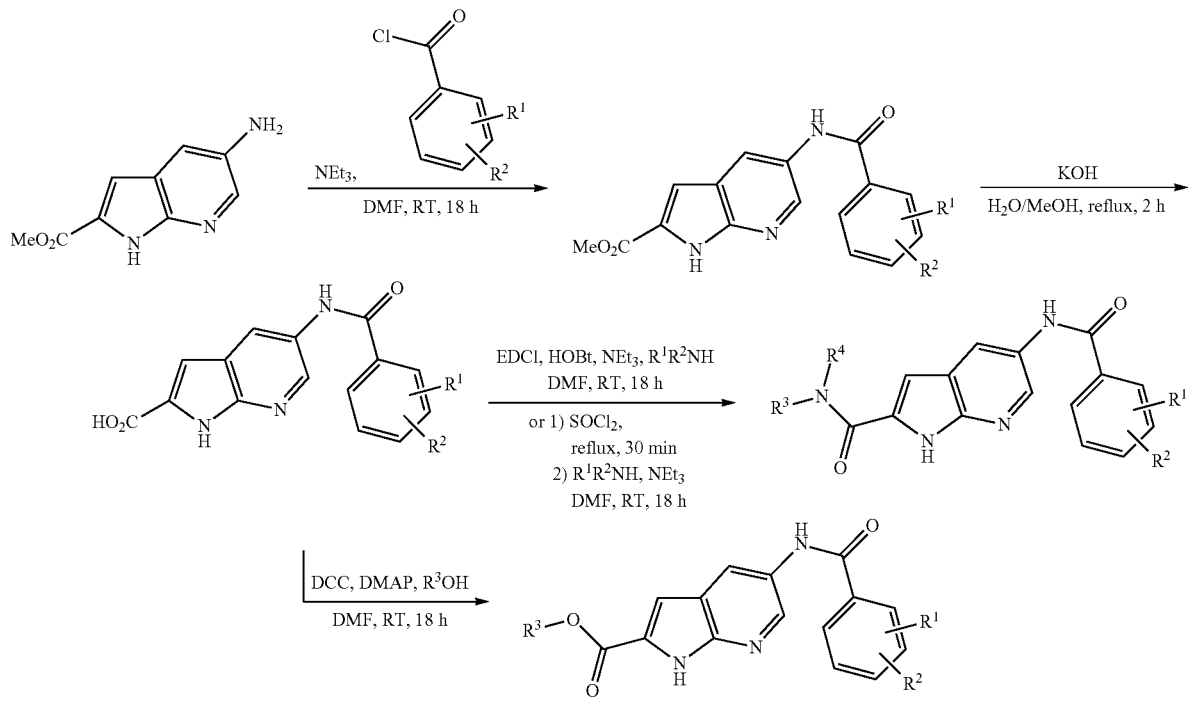

EXAMPLE 39

Preparation of 5-(2-bromobenzamido)-N-(3-(dimethylamino)propyl)-1H-pyrrolo[2,3-b]pyridine-2-carboxamide (ND0009)

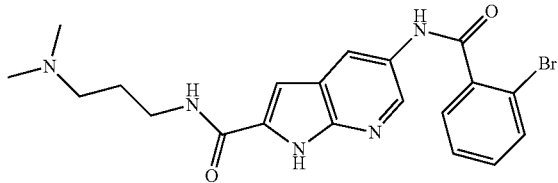 [SMILES: CN(C)CCCNC(=O)c1cc2cc(NC(=O)c3ccccc3Br)cnc2[nH]1]

A flask is charged successively with 425 mg (1.14 mmol) of methyl 5-(2-bromobenzamido)-1H-pyrrolo[2,3-b]pyridine-2-carboxylate (example 6), 20 mL of methanol, 20 mL of water and 127 mg of potassium hydroxide. The reaction mixture is refluxed for 2 hours and then left to return to room temperature. The solution is concentrated under reduced pressure and then diluted in 200 mL of water. The aqueous phase is extracted with 3×60 mL of ethyl acetate, and acidified with 32% hydrochloric acid, until the pH is between 2 and 3. The aqueous phase is extracted again with 3×60 mL of ethyl acetate. The organic phases are combined, dried over sodium sulphate and evaporated under reduced pressure. 250 mg of a beige solid is obtained, and is used directly without purification.

A flask is charged successively with 250 mg (0.70 mmol) of the solid formed previously, 25 mL of dimethylformamide (distilled on calcium hydride), 96 μL (0.76 mmol) of 3-(dimethylamino)-1-propylamine, 3.28 mL (23.05 mmol) of triethylamine and 94 mg (0.70 mmol) of hydroxybenzotriazole. It is stirred for 15 minutes at room temperature and then 160 mg (0.83 mmol) of N-(3-dimethylaminopropyl)-N'-ethylcarbodiimide (EDCl) hydrochloride is added. The reaction mixture is stirred for a further 18 h. The solvent is then evaporated under reduced pressure and the residue is taken up in 100 mL of water. The aqueous phase is extracted with 6×50 mL of dichloromethane, the organic phases are combined and are then dried over sodium sulphate and evaporated under reduced pressure. The raw product is purified by silica gel chromatography (ethyl acetate/methanol eluent). 98 mg of beige solid is obtained (20% from methyl 5-(2-bromobenzamido)-1H-pyrrolo[2,3-b]pyridine-2-carboxylate).

$^1$H NMR (300 MHz, CD$_3$OD): 8.40 (s, 7.62-7.27 (m, 4H), 6.97 (s, 1H), 3.34 (t, 2H), 2.33 (t, 2H), 2.17 (s, 6H), 1.74 (m, 2H).

HPLC: 95%. MS (ESI): 442.2; 446.2 (M+1).

EXAMPLE 40

Preparation of 5-(3-(2-methylthiazol-4-yl)benzamido)-N-(3-(dimethylamino)propyl)-1H-pyrrolo[2,3-b]pyridine-2-carboxamide (ND0011)

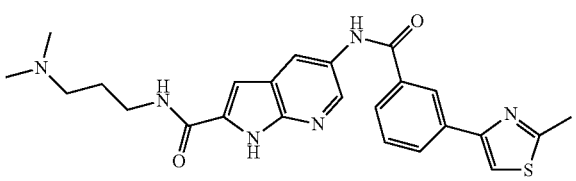

The compound is prepared according to the protocol described in example 39 using 150 mg of methyl 5-(4-(2-methylthiazol-4-yl)benzamido)-1H-pyrrolo[2,3-b]pyridine- 2-methyl carboxylate (example 8) instead of 5-(2-bromobenzamido)-1H-pyrrolo[2,3-b]pyridine-2-carboxylate AT10-3A. After treatment, 73 mg of beige solid is obtained (22% over 2 stages), ¹H NMR (300 MHz, CD₃OD): 8.50-8.39 (m, 2H), 7.97 (m, 4H), 7.74 (s, 1H), 7.01 (s, 1H), 3.40 (t, 2H), 2.69 (s, 3H), 2.60 (t, 2H), 2.06 (s, 6H), 1.85 (m, 2H).

HPLC: 80%. MS (ESI): 463.3 (M+1).

EXAMPLE 41

Preparation of N-(2-(3-(dimethylamino)propylcarbamoyl)-1H-pyrrolo[2,3-b]pyridin-5-yl)quinoxaline-6-carboxamide (ND0012)

Stage 1: Preparation of methyl 5-(quinoxaline-6-carboxamido)-1H-pyrrolo[2,3-b]pyridine-2-carboxylate

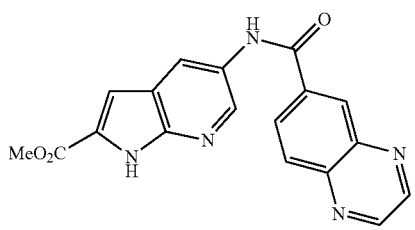 [SMILES: COC(=O)c1cc2cc(NC(=O)c3ccc4nccnc4c3)cnc2[nH]1]

The compound is prepared according to the protocol described in example 1 (stage 2) using 55 mg of quinoxaline-6-carbonyl chloride instead of cyclopropanecarbonyl chloride. After treatment, 42 mg of beige solid is obtained (60%).

Stage 2: Preparation of N-(2-(3-(dimethylamino)propylcarbamoyl)-1H-pyrrolo[2,3-b]pyridin-5-yl)quinoxaline-6-carboxamide

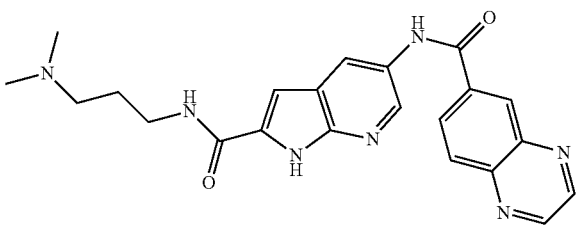 [SMILES: CN(C)CCCNC(=O)c1cc2cc(NC(=O)c3ccc4nccnc4c3)cnc2[nH]1]

The compound is prepared according to the protocol described in example 39 using 42 mg of methyl 5-(quinoxaline-6-carboxamido)-1H-pyrrolo[2,3-b]pyridine-2-carboxylate described previously instead of methyl 5-(2-bromobenzamido)-1H-pyrrolo[2,3-b]pyridine-2-carboxylate. After treatment, 7 mg of beige solid is obtained (15% over 2 stages).

¹H NMR (300 MHz, CD₃OD): 8.89 (m, 2H), 8.65 (s, 1H), 8.52 (m, 1H), 8.45 (m, 1H), 8.30 (d, 1H), 8.14 (d, 1H), 6.99 (s, 1H), 3.36 (t, 2H), 2.40 (t, 2H), 2.22 (s, 6H), 1.74 (m, 2H). HPLC: 83%. MS (ESI): 418.3 (M+1).

EXAMPLE 42

Preparation of 5-(benzamido)-1H-pyrrolo[2,3-b]pyridine-2-4-methoxyphenyl carboxylate (ND0004)

Stage 1: Preparation of methyl 5-(benzamido)-1H-pyrrolo[2,3-b]pyridine-2-carboxylate

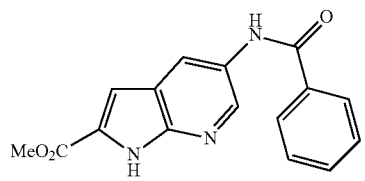 [SMILES: COC(=O)c1cc2cc(NC(=O)c3ccccc3)cnc2[nH]1]

The compound is prepared according to the protocol described in example A (stage 2) using 200 mg (1.04 mmol) of methyl 5-amino-1H-pyrrolo[2,3-b]pyridine-2-carboxylate and 121 μL (1.04 mmol) of benzoyl chloride instead of cyclopropanecarbonyl chloride. After treatment, 170 mg of beige solid is obtained (55%).

Stage 2: Preparation of 5-(benzamido)-1H-pyrrolo[2,3-b]pyridine-2 4-methoxyphenyl carboxylate

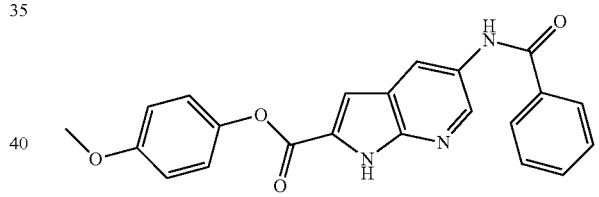

A flask is charged with 100 mg (0.34 mmol) of methyl 5-(benzamido)-1H-pyrrolo[2,3-b]pyridine-2-carboxylate described previously, 20 mL of methanol, 20 mL of water and 200 mg (3.40 mmol) of potassium hydroxide. The reaction mixture is heated to 60° C. for 30 minutes and then left to return to room temperature. The solution is concentrated under reduced pressure and then diluted in 100 mL of water. The aqueous phase is extracted with 3×30 mL of ethyl acetate, then acidified with 32% hydrochloric acid until the pH is between 2 and 3. The aqueous phase is extracted again with 3×30 mL of ethyl acetate. The organic phases are combined, dried over sodium sulphate and evaporated under reduced pressure. 85 mg of white solid is obtained, and is used directly without purification.

A flask is charged successively with 85 mg (0.30 mmol) of the solid formed previously, 20 mL of tetrahydrofuran, 68 mg (0.38 mmol) of p-methoxyphenol, 90 mg (0.30 mmol) of N,N'-dicyclohexylcarbodiimide (DCC) and 27 mg (0.15 mmol) of 4-dimethylaminopyridine (DMAP). It is stirred for 18 hours. The solvent is evaporated under reduced pressure and the residue is taken up in 100 mL of water. The aqueous phase is extracted with 3×30 mL of ethyl acetate, the organic phases are combined and are dried over sodium sulphate and evaporated under reduced pressure. The raw product is purified by silica gel chromatography (ethyl acetate/petroleum ether eluent). 17 mg of beige solid is obtained (10% starting from methyl 5-(benzamido)-1H-pyrrolo[2,3-b]pyridine-2-carboxylate).

$^1$H NMR (300 MHz, DMSO d$_6$): 12.40 (br s, 1H), 10.52 (br s, 1H), 8.77 (d, 1H), 8.67 (d, 1H), 8.08 (d, 2H), 7.68-7.60 (m, 3H), 7.49 (s, 1H), 7.32 (d, 2H), 7.08 (d, 2H).

EXAMPLE 43

Preparation of 5-(3-fluorobenzamido)-N-(2-morpholinoethyl)-1H-pyrrolo[2,3-b]pyridine-2-carboxamide (ND0006)

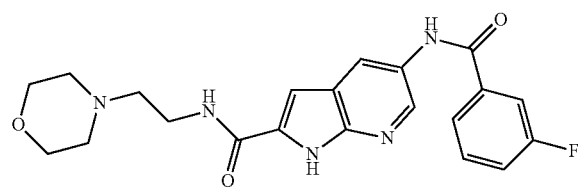 [SMILES: O=C(Nc1cnc2[nH]c(C(=O)NCCN3CCOCC3)cc2c1)c1cccc(F)c1]

A flask is charged with 865 mg (2.76 mmol) of methyl 5-(3-fluorobenzamido)-1H-pyrrolo[2,3-b]pyridine-2-carboxylate (example 5), 20 mL of ethanol, 20 mL of water and 464 mg (8.30 mmol) of potassium hydroxide. The reaction mixture is heated at 60° C. for 30 minutes and then left to return to room temperature. The solution is concentrated under reduced pressure and then diluted in 200 mL of water. The aqueous phase is extracted with 3×60 mL of ethyl acetate and acidified with 32% hydrochloric acid until the pH is between 2 and 3. The aqueous phase is extracted again with 5×50 mL of ethyl acetate. The organic phases are combined, dried over sodium sulphate and evaporated under reduced pressure. 590 mg of white solid is obtained, and is used directly without purification (raw yield of 71%).

A flask is charged with 280 mg (0.93 mmol) of the solid formed previously together with 5 mL of thionyl chloride under argon atmosphere. The reaction is carried out under reflux for 1 hour and then left to return to room temperature. The solvent is then evaporated under reduced pressure and 10 mL of dimethylformamide (distilled on calcium hydride), 0.2 mL (1.40 mmol) of triethylamine and 135 μL (1.03 mmol) of 4-(2-aminoethyl)morpholine are added to the mixture. It is stirred at room temperature for 2 hours and the solvent is evaporated under reduced pressure. The residue is taken up in 100 mL of ethyl acetate. The organic phase is rinsed with 30 mL of saturated solution of sodium bicarbonate, then with 3×30 mL of water. The organic phase is dried over sodium sulphate and the solvent is evaporated under reduced pressure. 48 mg of yellow solid is obtained (13%).

$^1$H NMR (300 MHz, DMSO d$_6$): 12.09 (br s, 1H), 10.43 (br s, 1H), 8.55 (d, 1H), 8.46 (d, 1H), 8.44 (br s, 1H), 7.87-7.78 (m, 2H), 7.65-7.58 (m, 1H), 7.50-7.43 (m, 1H), 7.09 (s, 1H), 3.58 (t, 4H), 3.42 (m, 2H), 3.31 (m, 2H), 2.42 (t, 4H).

HPLC: 85%. MS (ESI): 412.2 (M+1).

EXAMPLE F

Synthesis of Inhibitor Starting from Substituted Aromatic Amines

The Inhibitors of Example F are Obtained as Represented in Scheme 16.

Scheme 16

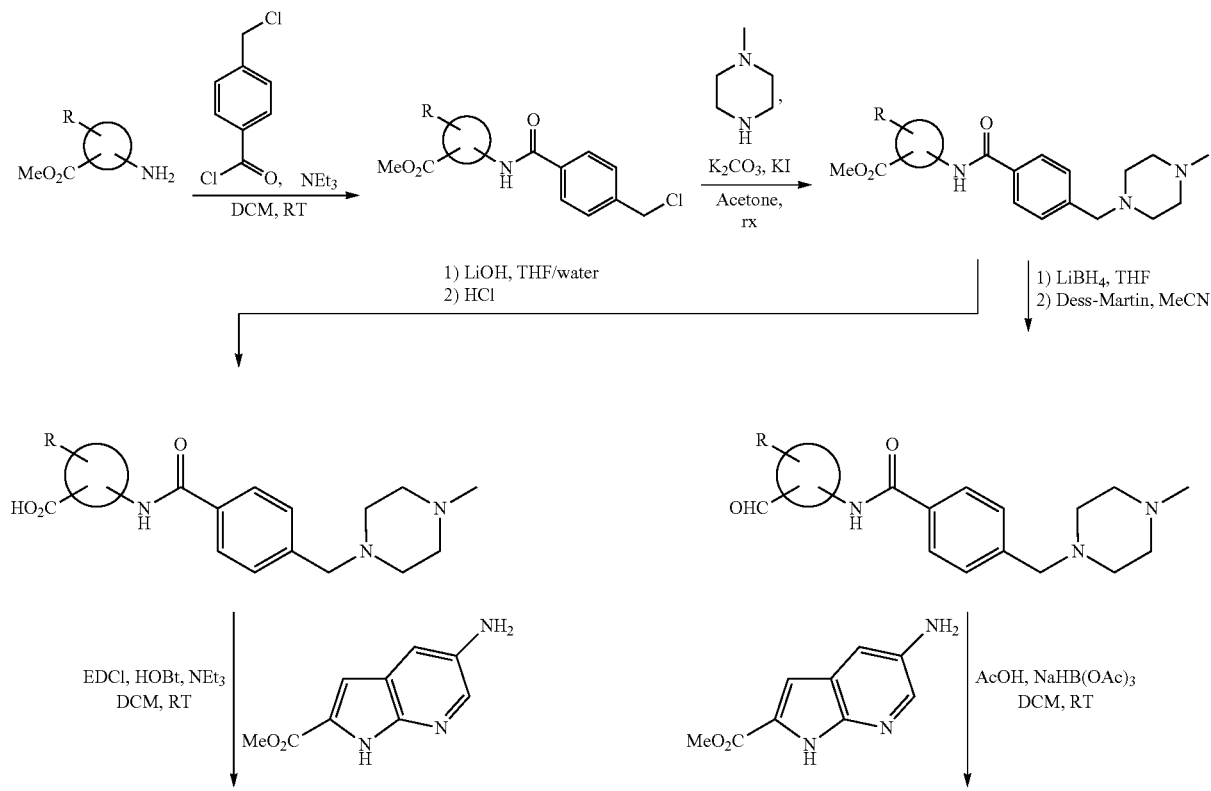

101

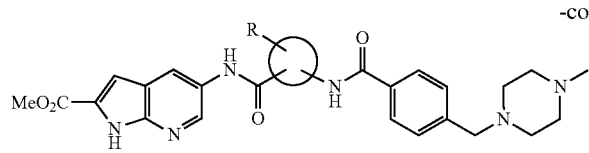

102

-continued

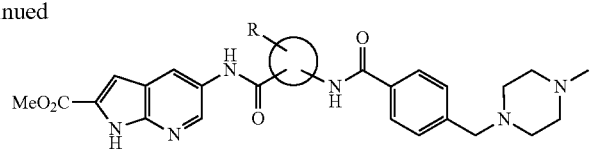

Wherein

represents various aromatic amines carrying an ester function on the aromatic ring.

In one embodiment

represents:

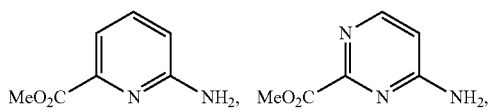

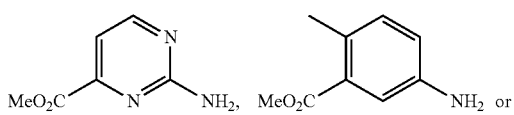

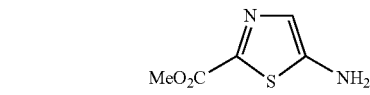

The synthesis starts with the use of various aromatic amines carrying an ester methylic or ethylic function (Liu, Y., Wang, C et al, *Organic Process Resarch & Development*, 2008, 12(3), 490-495). This amine reacts with 4-chloromethylbenzoyle chloride to give an intermediate amide. The amide obtained is substituted with N-methylpiperazine in acetone at reflux. The intermediate ester obtained is saponified and then coupling with methyl 5-amino-1H-pyrrolo[2,3-b]pyridine-2-carboxylate or reduced into aldehyde to then undergo a reductive amination with methyl 5-amino-1H-pyrrolo[2,3-b]pyridine-2-carboxylate. Some examples are given below to illustrate the present invention.

EXAMPLE 82

Preparation of inhibitor methyl 5-(4-(5-(4-((4-methylpiperazin-1-yl)methyl)-benzamido)-2-methylbenzamido-1H-pyrrolo[2,3-b]pyridine-2-carboxylate (ND0117)

Step 1: Preparation of methyl5-(4-(chloromethyl)benzamido)-2-methylbenzoate

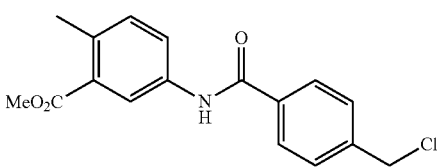 [SMILES: COC(=O)c1cc(NC(=O)c2ccc(CCl)cc2)ccc1C]

A reactor is charged with 1 g (6.06 mmol) of methyl 3-amino-6-methylbenzoate and 1.2 g (11.9 mmol) of triethylamine in 25 ml of dichloromethane. 1.145 g (6.05 mmol) of 4-chloromethylbenzoyle chloride is then added and the mixture is stirred at room temperature for 2 hours. The reacting medium is then washed with 10 ml of a saturated NaHCO$_3$ solution, 10 ml of water and 10 ml of a saturated NaCl solution. The organic phase is dried, evaporated and the obtained residue is triturated in ethylic ether and then in pentane to give a white solid (1.2 g, 66%).

Step 2: preparation of methyl 5-(4-((4-methylpiperazin-1-yl)methyl)benzamido)-2-methylbenzoate

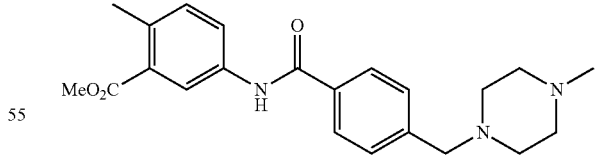

A reactor is charged with 1 g (3.3 mmol) of the solid obtained in step 1, 2.28 g (16.5 mmol) of potassium carbonate, 30 ml of acetone, 0.39 g (3.96 mmol) of N-methylpiperazine and 55 mg (0.33 mmol) of potassium iodide. The mixture is heated at reflux for 6 hours. The solvent is then evaporated under reduce pressure and the residue is taken off into 100 ml of a saturated sodium bicarbonate solution. The aqueous phase is extracted by 3*30 ml ethyl acetate. The organic phases are then combined, dried on sodium sulphate and evaporated under reduced pressure. The obtained product is triturated in ethylic ester and then dried to give a white solid (700 mg, 56%).

Step 3: Preparation of 5-(4-((4-methylpiperazin-1-yl)methyl)benzamido)-2-methylbenzoic acid

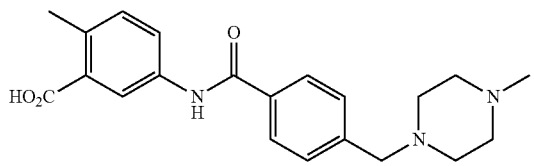

A reactor is charged with 0.5 g (1.3 mmol) of the solid obtained in step 2, 20 ml of a mixture water/THF (1/1) and 0.55 g (13 mmol) of lithium hydroxide. The mixture is stirred at room temperature for 6 hours. The solution is concentrated under reduced pressure and then diluted in 100 ml of water. The aqueous phase is extracted by 3*30 ml of ethyl acetate and acidified with chlorhydric acid 32% until pH comprised between 2 and 3. the aqueous phase is extracted with 3*30 ml ethyl acetate. The organic phases are combined, dried on sodium sulphate and evaporated under reduced pressure. 250 mg of a solid is obtained (52%).

Step 4: Preparation of methyl 5-(5-(4-((4-methylpiperazin-1-yl)methyl)benzamido)-2-methylbenzamido)-1H-pyrrolo[2,3-b]pyridine-2-carboxylate (ND0117)

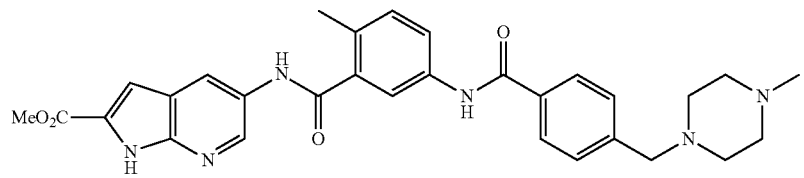 [SMILES: COC(=O)c1cc2cc(NC(=O)c3cc(NC(=O)c4ccc(CN5CCN(C)CC5)cc4)ccc3C)cnc2[nH]1]

A reactor is charged successively with 150 mg (0.4 mmol) of the solid obtained in step 3, 15 ml of anhydrous dichloromethane, 90 mg (0.4 mmol) of methyl 5-amino-1H-pyrrolo[2,3-b]pyridine-2-carboxylate, 0.12 g (0.49 mmol) of triethylamine and 93 mg (0.61 mmol) of hydroxybenzotriazole. The mixture is stirred at room temperature for 15 min and then 90 mg (0.49 mmol) of N-(3-dimethylaminopropyl)-N'-ethylcarbodiimide hydrogen carbonate (EDCl) is added. The mixture is stirred for 16 hours. The solvent is then evaporated under reduced pressure and the residue is taken off in 100 ml of water. The aqueous phase is extracted by 6*50 ml dichloromethane. The aqueous phases are combined, dried on sodium sulphate and then evaporated under reduced pressure. The raw product obtained is purified by preparative HPLC and 18 mg (8%) of a solid is obtained.

$^1$H NMR (400 MHz, CD$_3$OD): 8.63 (d, 1H), 8.57 (d, 1H), 7.98 (d, 2H), 7.96 (m, 1H), 7.70 (m, 1H), 7.56 (d, 2H), 7.36 (m, 1H), 7.23 (s, 1H), 3.98 (s, 3H), 3.80 (s, 2H), 3.60-3.00 (m, 8H), 2.95 (s, 3H), 2.55 (s, 3H); HPLC: 95%. MS: 541.4 (M+1).

EXAMPLE 83

Preparation of inhibitor methyl 5-(5-(4-((4-methylpiperazin-1-yl)methyl)-benzamido)-2-methylbenzamido)-1H-pyrrolo[2,3-b]pyridine-carboxylate (ND0118)

Step 1: preparation of N-(3-(hydroxymethyl)-4-methylphenyl)-4-((4-methylpiperazine-1-yl)-methyl)benzamide

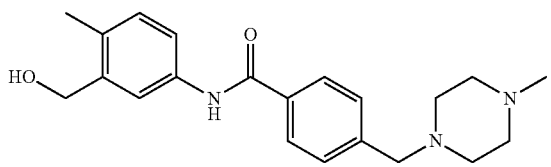 [SMILES: Cc1ccc(NC(=O)c2ccc(CN3CCN(C)CC3)cc2)cc1CO]

A reactor is charged with 100 mg (0.26 mmol) of methyl 5-(4-((4-methylpiperazin-1-yl)methyl)benzamido)-2-methylbenzoate (example 82, step 2) in 5 ml anhydrous tetrahydrofuran and 38 mg (1.75 mmol) of lithium borohydride is added. The mixture is stirred at room temperature for 16 hours. The mixture is then concentrated under reduced pressure, taken off into 60 ml of ethyl acetate, washed with 20 ml of a saturated NaHCO$_3$ solution, 20 ml of water and 20 ml of a saturated NaCl solution. The organic phase is dried, evaporated and the residue is taken off and triturated into ethylic ester to give a solid (80 mg, 86%)

Step 2: preparation of N-(3-formyl-4-methylphenyl)-4-((4-methylpiperazin-1-yl)methyl)-benzamide

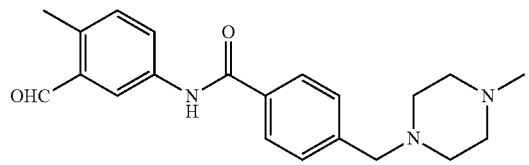

A reactor is charged with 150 mg (0.42 mmol) of the solid obtained in step 1 and 216 mg (0.5 mmol) of the Dess-Martin reagent in 5 ml acetonitrile. The mixture is stirred at room temperature for 16 hours. The insoluble compounds are filtered and the filtrate is concentrated under reduced pressure. The obtained solid is washed with ethylic ether and pentane to give the required aldehyde (120 mg, 82%).

Step 3: Preparation of methyl 5-(5-(4-((4-methylpiperazin-1-yl)methyl)benzamido)-2-methyl-benzylamino)-1H-pyrrolo[2,3-b]pyridine-2-carboxylate (ND0118)

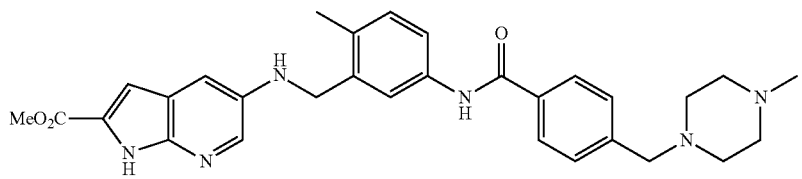 [SMILES: COC(=O)c1cc2cc(NCc3cc(NC(=O)c4ccc(CN5CCN(C)CC5)cc4)ccc3C)cnc2[nH]1]

A reactor is charged with 120 mg (0.34 mmol) of the solid obtained in step 2, 15 ml of anhydrous dichloromethane, 78 mg (0.41 mmol) of methyl 5-amino-1H-pyrrolo[2,3-b]pyridine-2-carboxylate, 216 mg (1.02 mmol) of sodium acetoxyborohydride and a catalytic amount of acetic acid. The mixture is stirred at room temperature for 24 hours. The solvent is then evaporated under reduced pressure and the residue is taken off in 100 ml of water. The aqueous phase is extracted by 3*30 ml ethyl acetate. The aqueous phases are combined, dried on sodium sulphate and then evaporated under reduced pressure. The raw product obtained is purified by preparative HPLC and 18 mg of a solid is obtained (10%).

$^1$H NMR (400 MHz, DMSO d$^6$): 12.02 (br s, 1H), 10.10 (br s, 1H), 8.10 (d, 1H), 7.86 (d, 2H), 7.69 (d, 1H), 7.64 (d, 1H), 7.39 (d, 2H), 7.18 (d, 1H), 6.95 (s, 1H), 6.90 (s, 1H), 6.05 (br s, 1H), 4.21 (s, 2H), 3.82 (s, 3H), 3.45 (s, 2H), 2.38 (m, 8H), 2.08 (s, 3H); HPLC: 95%. MS: 527.4 (M+1).

EXAMPLE 84

Preparation of methyl 5-(5-(4-((4-methylpiperazin-1-yl)methyl)benzamido)thiazol-2-yl)methylamino-1H-pyrrolo[2,3-b]pyridine-2-carboxylate (ND0127)

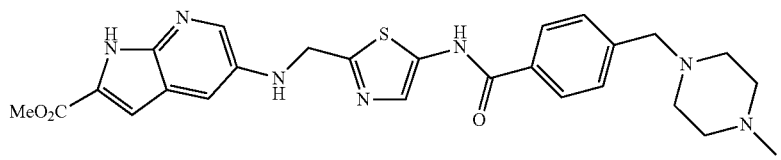 [SMILES: COC(=O)c1cc2cc(NCc3ncc(NC(=O)c4ccc(CN5CCN(C)CC5)cc4)s3)cnc2[nH]1]

The compound is obtained by using the procedure of example 83 replacing methyl 3-amino-6-methylbenzoate by ethyl 5-aminothiazole-2-carboxylate.

EXAMPLE 85

Preparation of methyl 5-(6-(4-((4-methylpiperazin-1-yl)methyl)benzamido)pyridine-2-carbonylamino)-1H-pyrrolo[2,3-b]pyridine-2-carboxylate (ND0128)

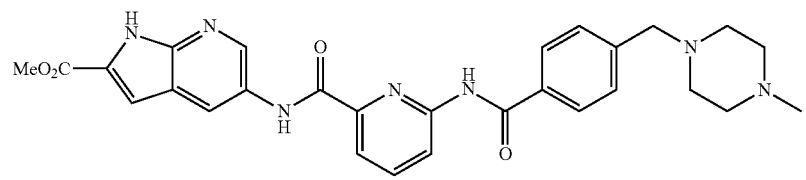 [SMILES: COC(=O)c1cc2cc(NC(=O)c3cccc(NC(=O)c4ccc(CN5CCN(C)CC5)cc4)n3)cnc2[nH]1]

The compound is obtained by using the procedures of example 82 replacing methyl 3-amino-6-methylbenzoate by methyl 6-aminopyridine-2-carboxylate.

EXAMPLE 86

Préparation du methyl 5-(2-(4-((4-methylpiperazin-1-yl)methyl)benzamido)pyrimidine-4-aminomethyl)-1H-pyrrolo[2,3-b]pyridine-2-carboxylate (ND0129)

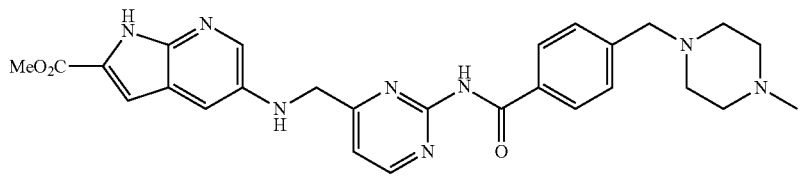 [SMILES: COC(=O)c1cc2cc(NCc3ccnc(NC(=O)c4ccc(CN5CCN(C)CC5)cc4)n3)cnc2[nH]1]

The compound is obtained by using the procedures of example 83 replacing methyl 3-amino-6-methylbenzoate by methyl 2-aminopyrimidine-4-carboxylate.

EXAMPLE 87

Preparation of Préparation du methyl 5-(4-(4-((4-methylpiperazin-1-yl)methyl)benzamido)pyrimidine-2-carbonylamino)-1H-pyrrolo[2,3-b]pyridine-2-carboxylate (ND0130)

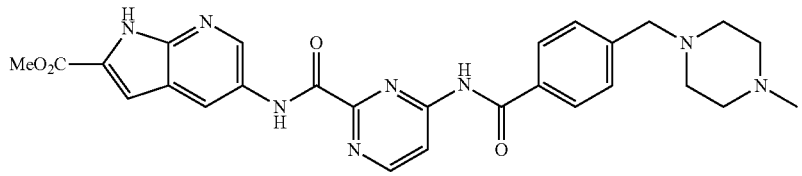 [SMILES: COC(=O)c1cc2cc(NC(=O)c3nccc(NC(=O)c4ccc(CN5CCN(C)CC5)cc4)n3)cnc2[nH]1]

The compound is obtained by using the procedures of example 82 replacing 3-amino-6-methylbenzoate by methyl 4-aminopyrimidine-2-carboxylate.

EXAMPLE G

Synthesis of inhibitor starting from 3-(trifluoromethyl)-4-methylbenzoic acid

The synthesis of example G is represented by the general scheme 17.

Scheme 17

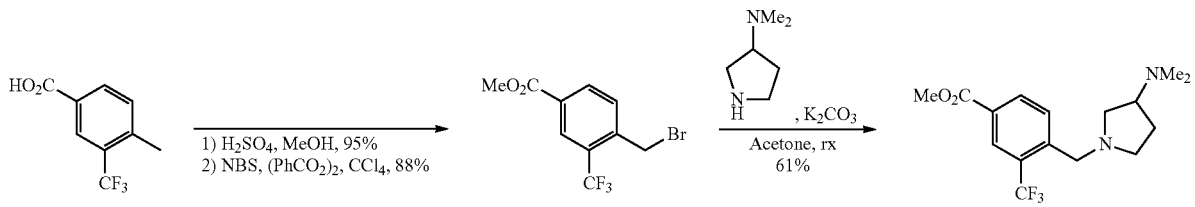

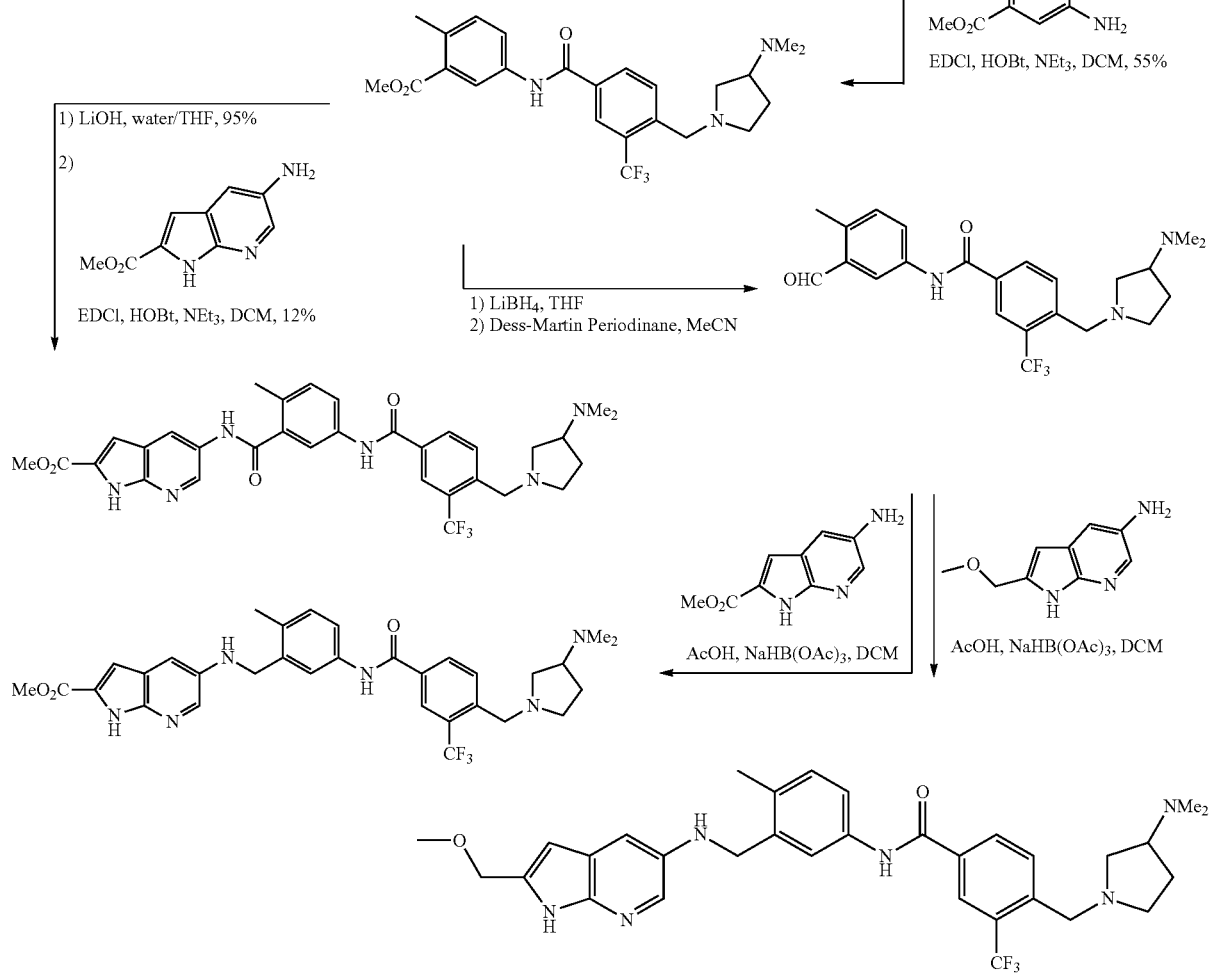

The 3-(trifluoromethyl)-4-methylbenzoic acid is transformed into methylic ester in methanol in the presence of sulfuric acid and then functionalized with bromine by the action of NBS in the presence of benzoic peroxide (Asaki, T. et al, *Bioorg. Chem. Med. Lett,* 2006, 16, 1421-1425). The halogenated compound is then substituted by 3-(N,N-dimethyl)pyrrolidine with acetone at reflux to give the expected product with a yield of 61%. The obtained compound is saponified and coupled to methyl 5-amino-2-methylbenzoate in the presence of EDCl, hydroxybenzotriazole and triethylamine. The intermediate amide obtained can be used in two different manner: it can be saponified and coupled with azaindolic compound (e.g: methyl 5-amino-1H-pyrrolo[2,3-b]pyridine-2-carboxylate or 5-amino-2-methoxymethyl-1H-pyrrolo[2,3-b]pyridine) or it can be reduced in aldehyde and then transformed in amine via a reductive amination. The following examples enable to well understand the invention.

EXAMPLE 88

Preparation of methyl 5-(5-(4-((3-(dimethylamino)pyrrolidin-1-yl-methyl)-3-(trifluoro-methyl)benzamido)-2-methylbenzamido)-1H-pyrrolo[2,3-b]pyridine-2-carboxylate (ND0119)

Step 1: preparation of methyl 3-(trifluoromethyl)-4-methylbenzoate

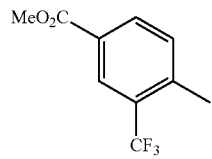

A reactor is charged with 1 g (4.9 mmol) of 3-(trifluoromethyl)-4-methylbenzoic acid in 10 ml methanol in the presence of a catalytic amount of sulphuric acid. The mixture is heated for 6 hours at reflux. The solvent is then evaporated under reduced pressure and 100 ml of a saturated sodium bicarbonate solution is added to the mixture. The solution is extracted by 3*30 ml ethyl acetate. The organic phases are combined, dried on sodium sulphate and evaporated under reduced pressure to give the expected product (1 g, 95%).

Step 2: Preparation of methyl 4-(bromomethyl)-3-(trifluoromethyl)benzoate

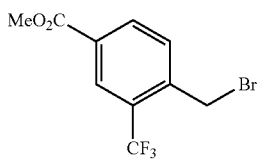

A reactor is charged with 1 g (4.6 mmol) of the compound obtained in step 1, 0.97 g (5.5 mmol) of N-bromosuccinimide, 133 mg (0.55 mmol) of benzyl peroxide and 25 ml of carbon tetrachloride. The mixture is heated for 4 hours at reflux. The solvent is evaporated under reduced pressure and 100 ml of a saturated sodium bicarbonate solution is added. The solution obtained is extracted with 3*30 ml ethyl acetate. The organic phases are combined, dried on sodium sulphate and evaporated under reduced pressure to give the expected product (1.2 g, 88%).

Step 3: preparation of methyl 4-((3-(dimethylamino)pyrrolidin-1-yl)methyl)-3-(trifluoromethyl)-benzoate

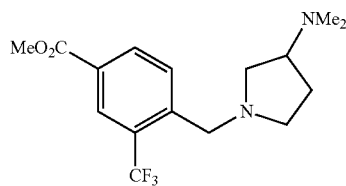 [SMILES: COC(=O)c1ccc(CN2CCC(N(C)C)C2)c(C(F)(F)F)c1]

A reactor is charged with 1.2 g (4.06 mmol) of the compound obtained in step 2, 0.55 g (4.88 mmol) of 3-dimethylaminopyrrolidine, 2.8 g (20.3 mmol) of potassium carbonate and 25 ml acetone. The mixture is heated for 6 hours at reflux. The solvent is evaporated under reduced pressure and 100 ml of water is then added. The obtained solution is extracted with 3*30 ml ethyl acetate. The organic phases are combined, dried on sodium sulphate and then evaporated under reduced pressure to give the expected product (0.8 g, 61%), Step 4: Preparation of methyl 5-(4-((3-(dimethylamino)pyrrolidin-1-yl)methyl)-3-(trifluoromethyl)-benzamido)-2-methylbenzoate

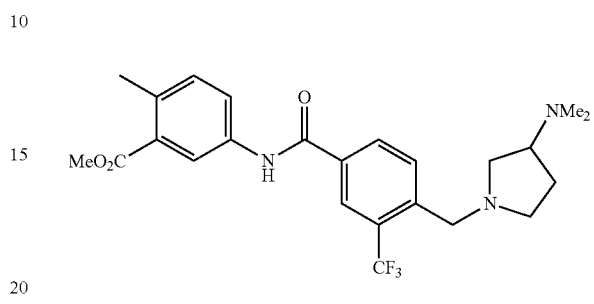

A reactor is charged with 0.8 g (2.42 mmol) of the compound obtained in step 3, 0.5 g (12.12 mmol) of lithium hydroxide and 20 ml of a mixture water/THF (1/1). The mixture is stirred at room temperature for 16 hours. The solution is concentrated under reduced pressure and then diluted in 100 ml water. The aqueous phase is extracted with 3*30 ml ethyl acetate, and acidified with chlorhydric acid 32% until a pH of between 2 and 3. The aqueous phase is extracted with 3*30 ml ethyl acetate. The organic phases are combined, dried on sodium sulphate and evaporated under reduced pressure. 750 mg of a solid is obtained which is charged in a reactor and 25 ml anhydrous dichloromethane, 460 mg (2.84 mmol) of methyl 3-amino-6-methylbenzoate, 0.71 g (7.02 mmol) of triethylamine and 540 mg (3.52 mmol) of hydroxybenzotriazole are successively added. The mixture is stirred at room temperature for 15 minutes and then 540 mg (2.82 mmol) of EDCl are added. The reaction is stirred for 16 hours. The solvent is then evaporated under reduced pressure and the residue is taken off in 100 ml ethyl acetate. The organic phase is washed with 30 ml of a saturated sodium bicarbonate solution and 2*30 ml water. The organic phase is dried on sodium sulphate and evaporated under reduced pressure. After purification on a silica column 620 mg (52%) of the expected compound are obtained.

Step 5: Preparation of methyl 5-(5-(4-((3-(dimethylamino)pyrrolidin-1-yl)methyl)-3-(trifluoro-methyl)benzamido)-2-methylbenzamido)-1H-pyrrolo[2,3-b]pyridine-2-carboxylate (ND0119)

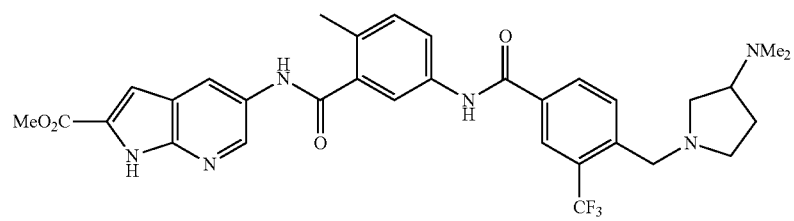 [SMILES: COC(=O)c1cc2cc(NC(=O)c3cc(NC(=O)c4ccc(CN5CCC(N(C)C)C5)c(C(F)(F)F)c4)ccc3C)cnc2[nH]1]

A reactor is charged with 620 mg (1.52 mmol) of the compound obtained in step 4, 180 mg (7.6 mmol) of lithium hydroxide and 20 ml of a mixture water/THF (1/1). The mixture is stirred at room temperature for 16 hours. The solution is concentrated under reduced pressure and then diluted in 100 ml water. The aqueous phase is extracted with 3*30 ml ethyl acetate and acidified with chlorohydric acid 32% until a pH of between 2 and 3. The aqueous phase is extracted again with 3*30 ml ethyl acetate. The organic phases are combined, dried on sodium sulphate and then evaporated under reduced pressure. 600 mg of a solid is obtained which is charged in a reactor and 25 ml of anhydrous dichloromethane, 350 mg (1.83 mmol) of methyl 5-amino-1H-pyrrolo[2,3-b]pyridine-2-carboxylate, 0.46 g (4.56 mmol) of triethylamine and 350 mg (2.28 mmol) of hydroxybenzotriazole are successively added, The mixture is stirred for 15 minutes at room temperature and then 540 mg (350 mmol) of EDCl are added. The reaction is stirred for 16 hours. The solvent is evaporated under reduced pressure and the residue is taken off in 100 ml ethyl acetate. The organic phase is washed with 30 ml of a saturated sodium bicarbonate solution and then with 2*30 ml of water. The organic phase is dried on sodium sulphate and evaporated under reduced pressure. After purification by preparative HPLC 110 mg of the expected compound are obtained (12%).

$^1$H NMR (400 MHz, CD$_3$OD): 8.59 (d, 1H), 8.53 (s, 1H), 8.26 (s, 1H), 8.18 (d, 1H), 7.95 (m, 2H), 7.70 (d, 1H), 7.34 (d, 1H), 7.21 (s, 1H), 3.95 (s, 3H), 3.87 (m, 2H), 3.49 (m, 1H), 2.95 (m, 1H), 2.79 (m, 2H), 2.53 (m, 1H), 2.48 (s, 3H), 2.25 (s, 6H), 2.06 (m, 1H), 1.78 (m, HPLC: 95%. MS: 623.4 (M+1).

EXAMPLE 89

Preparation of methyl 5-(5-(4-((3-(dimethylamino) pyrrolidin-1-yl)methyl)-3-(trifluoro-methyl)benzamido)-2-methylbenzylamino)-1H-pyrrolo[2,3-b] pyridine-2-carboxylate (ND0120)

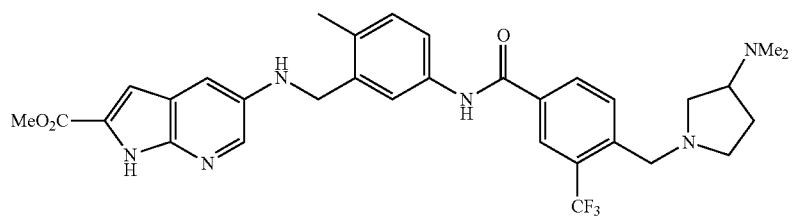 [SMILES: COC(=O)c1cc2cc(NCc3cc(NC(=O)c4ccc(CN5CCC(N(C)C)C5)c(C(F)(F)F)c4)ccc3C)cnc2[nH]1]

The compound is obtained by using the procedures of example 83 (step 3) replacing the methyl 5-(4-((4-methylpiperazin-1-yl)methyl)benzamido)-2-methylbenzoate with the methyl 5-(4-((3-(dimethylamino)pyrrolidin-1-yl)methyl)-3-(trifluoromethyl)-benzamido)-2-methylbenzoate.

EXAMPLE 90

Preparation of 2-(methoxymethyl)-5-(5-(4-((3-(dimethylamino)pyrrolidin-1-yl)methyl)-3-trifluoro-methyl)benzamido-2-methylbenzylamino-1H-pyrrolo[2,3-b]pyridine (ND0131)

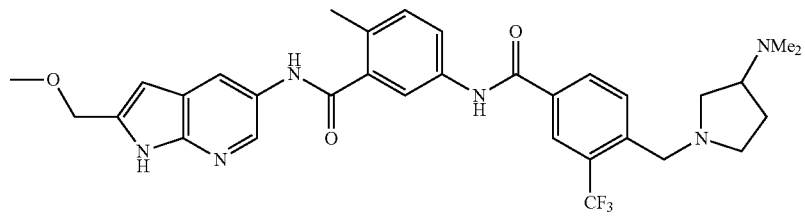 [SMILES: COCc1cc2cc(NC(=O)c3cc(NC(=O)c4ccc(CN5CCC(N(C)C)C5)c(C(F)(F)F)c4)ccc3C)cnc2[nH]1]

The compound is obtained by using the procedures of example 88 (step 5) replacing the methyl 5-amino-1H-pyrrolo[2,3-b]pyridine-2-carboxylate with the 5-amino-2-methoxymethyl-1H-pyrrolo[2,3-b]pyridine which is obtained according to the example 35.

EXAMPLE H

Synthesis of inhibitor starting from methyl 5-amino-2-methylbenzoate

The synthesis according to example H are represented in scheme 18.

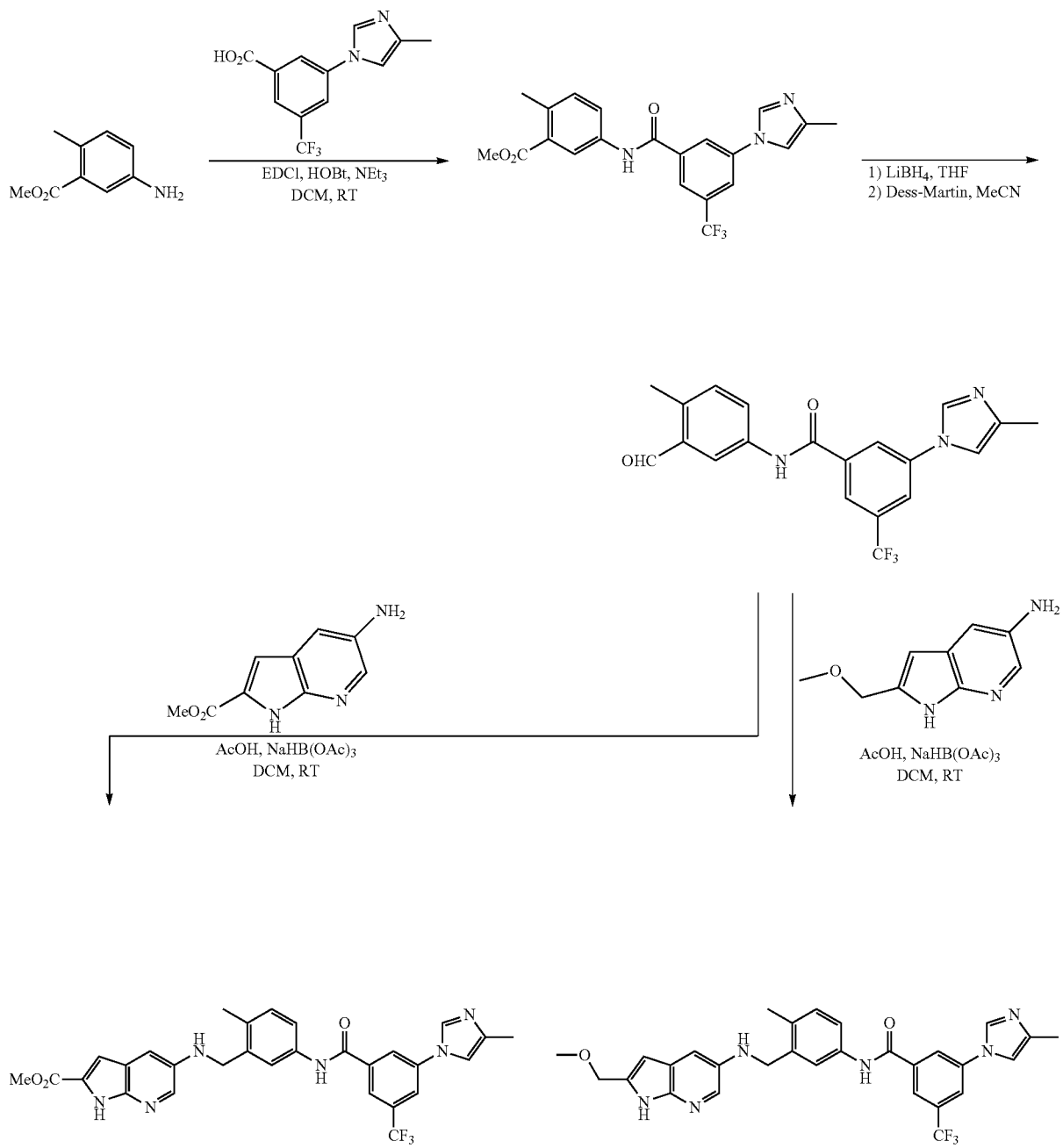

Scheme 18

The 3-(trifluoromethyl)-5-(4-methyl-1H-imidazol-1-yl)benzoic acid is coupled with the methyl 5-amino-2-methylbenzoate in the presence of EDCl, hydroxybenzotriazole and triethylamine (Shakespeare W. C, WO2007133562). The intermediate amide obtained is then reduced into aldehyde in 2 steps and then transformed into amine via a reductive amination reaction with aminoazaindoles. The following examples will enable to better understand the invention.

EXAMPLE 91

Preparation of methyl 5-(5-(3-(trifluoromethyl)-5-(4-methyl-1H-imidazol-1-yl)benzamido)-2-methylbenzylamino)-1H-pyrrolo[2,3-b]pyridine-2-carboxylate (ND0126)

Step 1: preparation of methyl 5-(3-(trifluoromethyl)-5-(4-methyl-1H-imidazol-1-yl)benzamido)-2-methylbenzoate

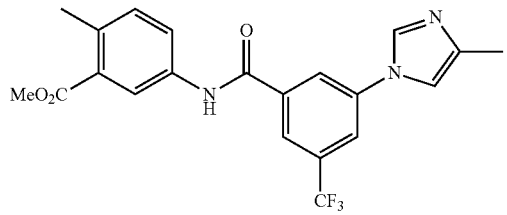

The compound is obtained using the procedures of example 88 (step 4) replacing the 4-((3-(dimethylamino)pyrrolidin-1-yl)methyl)-3-(trifluoromethyl)-benzoic acid (Shakespeare W. C, WO2007133562) by the 3-(trifluoromethyl)-5-(4-methyl-1H-imidazol-1-yl)benzoic acid.

Step 2: preparation of 3-(trifluoromethyl)-N-(3-formyl-4-methylphenyl)-5-(4-methyl-1H-imidazol-1-yl)benzamide

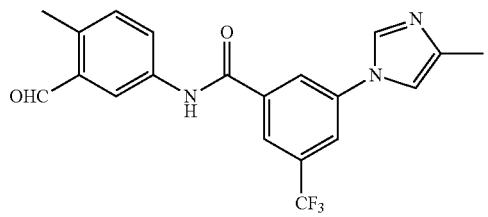

The compound is obtained by using the procedures of examples 83 (steps 1 and 2) replacing the methyl 5-(4-((4-methylpiperazin-1-yl)methyl)benzamido)-2-methylbenzoate with the methyl 5-(3-(trifluoromethyl)-5-(4-methyl-1H-imidazol-1-yl)benzamido)-2-methylbenzoate.

Step 3: preparation of methyl 5-(5-(3-(trifluoromethyl)-5-(4-methyl-1H-imidazol-1-yl)benzamido)-2-methylbenzylamino)-1H-pyrrolo[2,3-b]pyridine-2-carboxylate (ND0126)

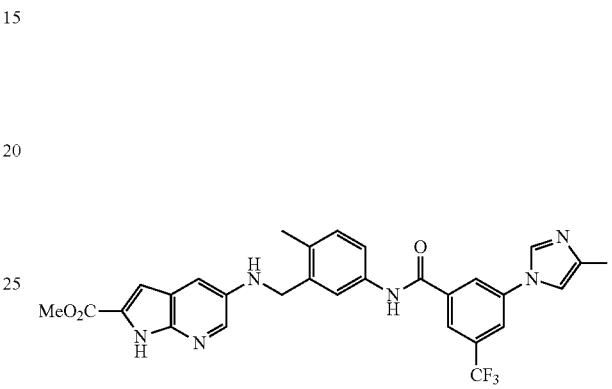

The composed is obtained according to example 83 (step 3) replacing N-(3-formyl-4-methylphenyl)-4-((4-methylpiperazin-1-yl)methyl)-benzamide with the 3-(trifluoromethyl)-N-(3-formyl-4-methylphenyl)-5-(4-methyl-1H-imidazol-1-yl)benzamide.

EXAMPLE 92

Preparation of 2-methoxymethyl-5-(5-(3-(trifluoromethyl)-5-(4-methyl-1H-imidazol-1-yl)benzamido)-2-methylbenzylamino-1H-pyrrolo[2,3-b]pyridine (ND0132)

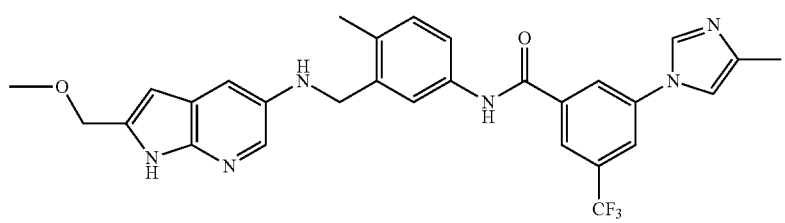

The compound is obtained according to example 91 (step 3) replacing 5-amino-1H-pyrrolo[2,3-b]pyridine-2-methyl carboxylate with 5-amino-2-methoxymethyl-1H-pyrrolo[2,3-b]pyridine

EXAMPLE I

Tests In Vitro of Inhibition of Kinases

Figure 1:
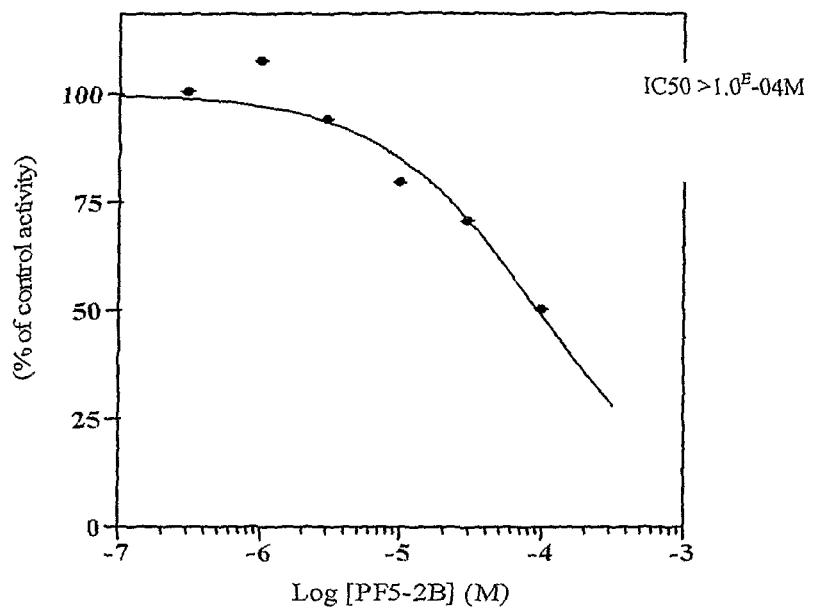
FIG. 1 shows the effects of compound ND0006 on the activity of human kinase AbI.
Figure 2:
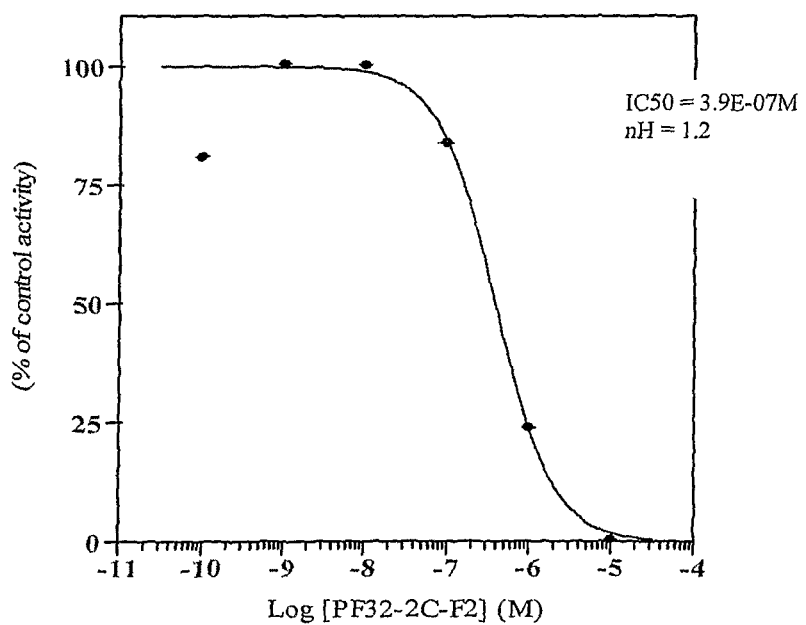
FIG. 2 shows the effects of compound ND0009 on the activity of human kinase AbI.
Figure 3:
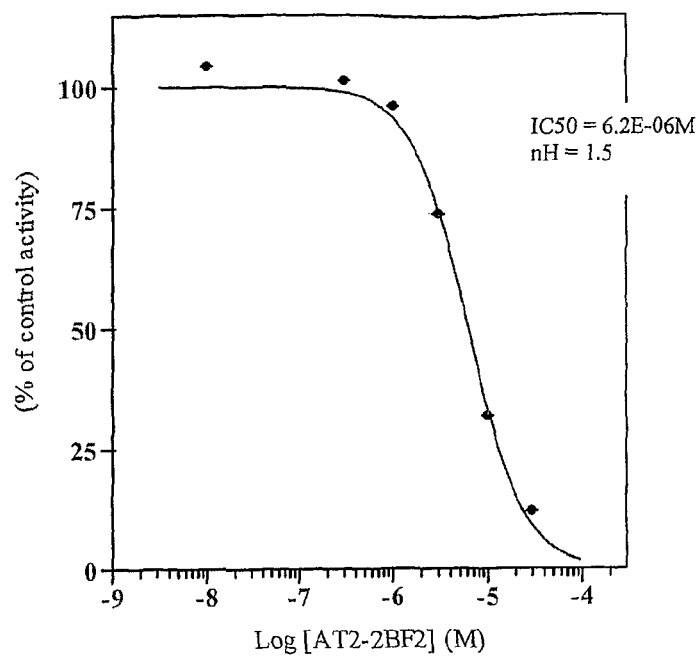
FIG. 3 shows the effects of compound ND0019 on the activity of human kinase AbI.
Figure 4:
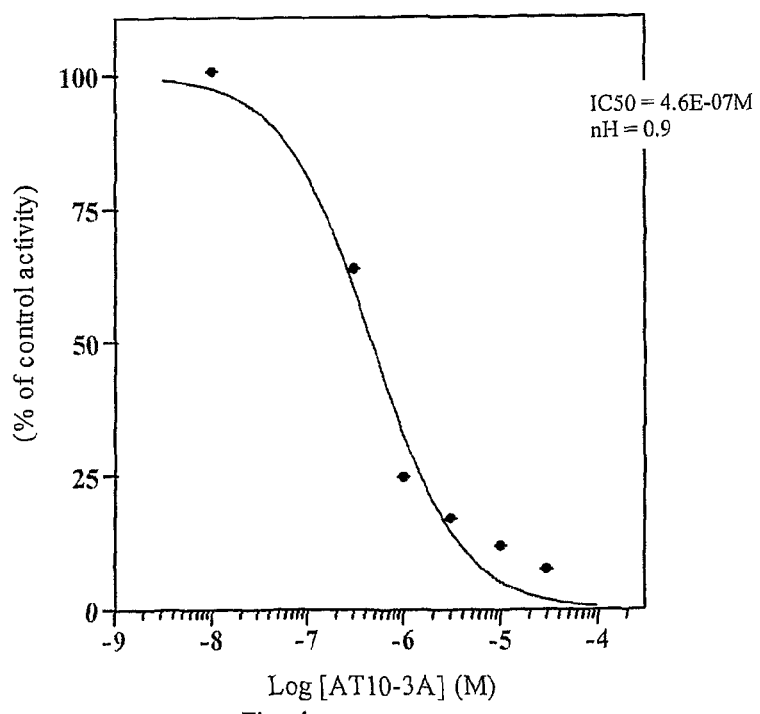
FIG. 4 shows the effects of compound ND0020 on the activity of human kinase AbI.
Figure 5:
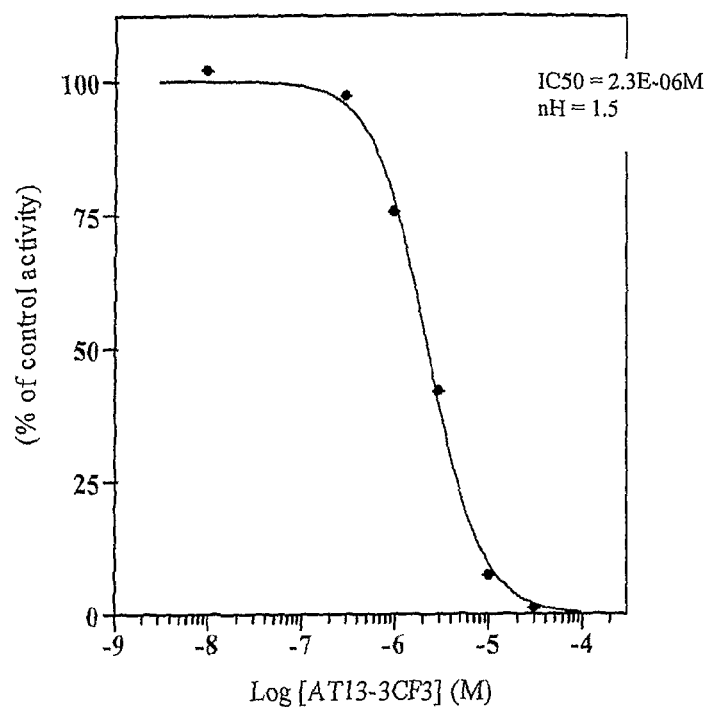
FIG. 5 shows the effects of compound ND0021 on the activity of human kinase AbI.
Figure 6:
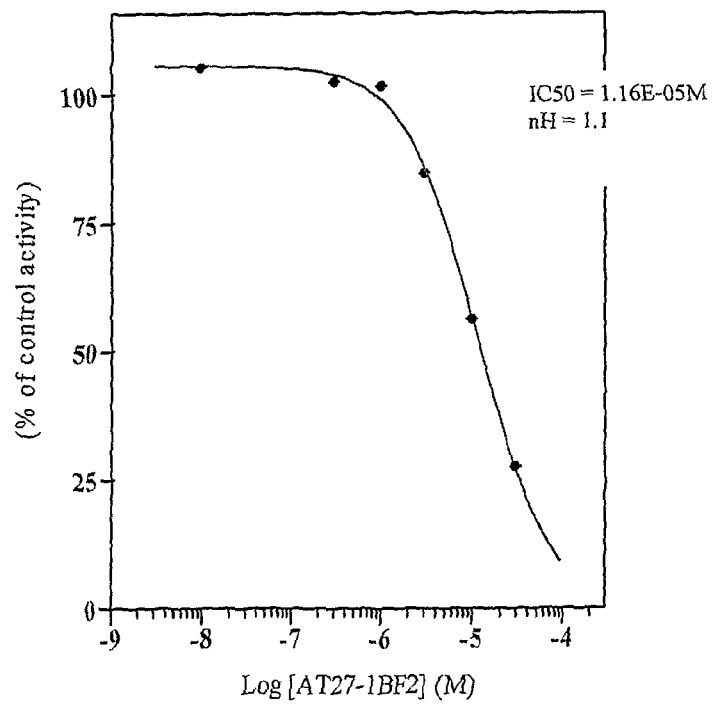
FIG. 6 shows the effects of compound ND0029 on the activity of human kinase AbI.
Figure 7:
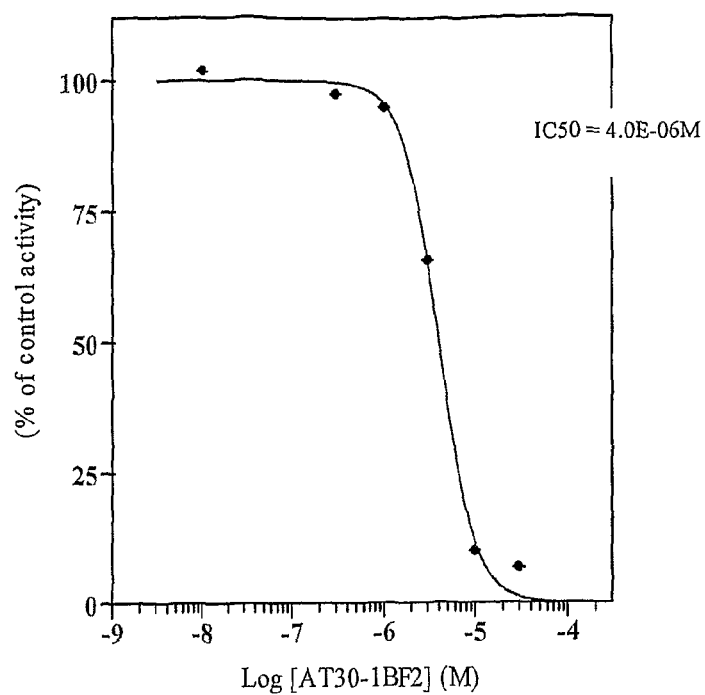
FIG. 7 shows the effects of compound ND0031 on the activity of human kinase AbI.
Figure 8:
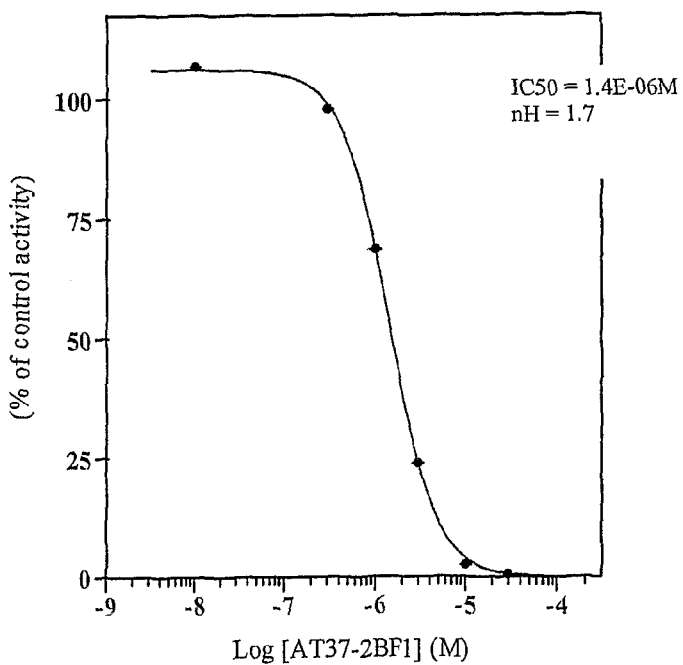
FIG. 8 shows the effects of compound ND0037 on the activity of human kinase AbI.
Figure 9:
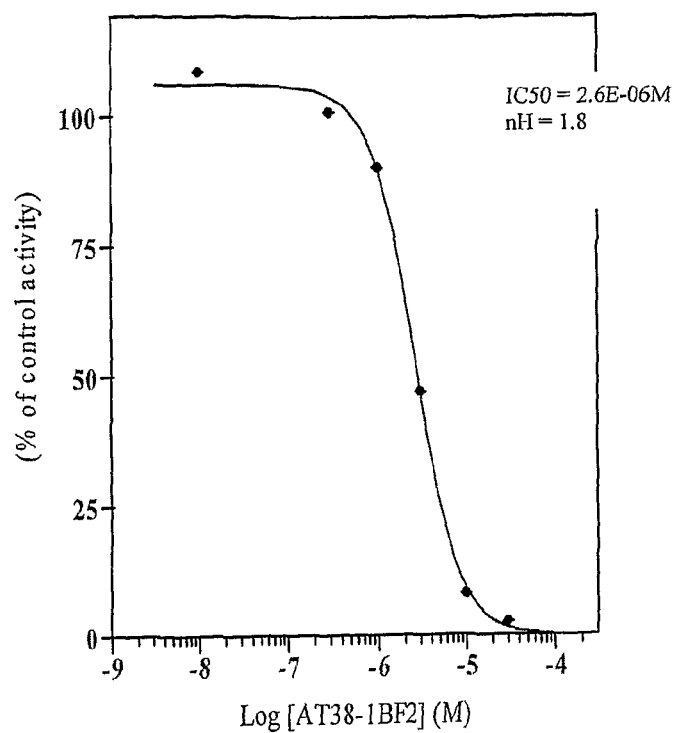
FIG. 9 shows the effects of compound ND0038 on the activity of human kinase AbI.
Figure 10:
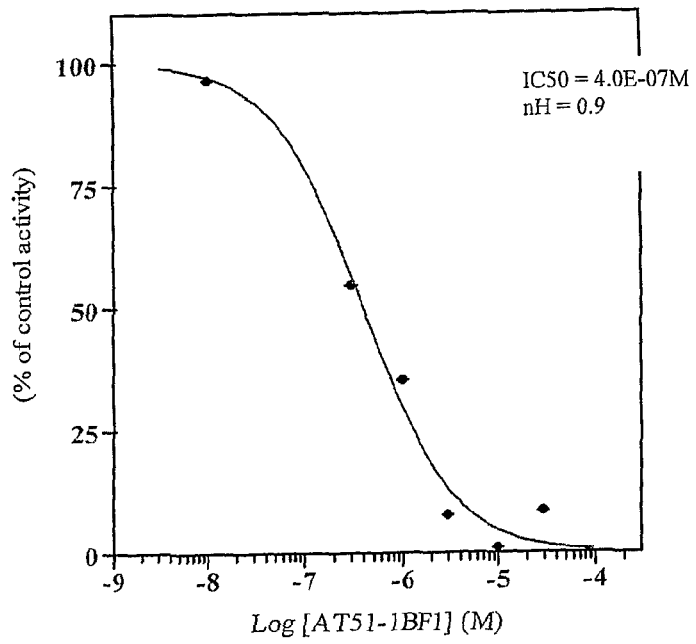
FIG. 10 shows the effects of compound ND0047 on the activity of human kinase AbI.
Figure 11:
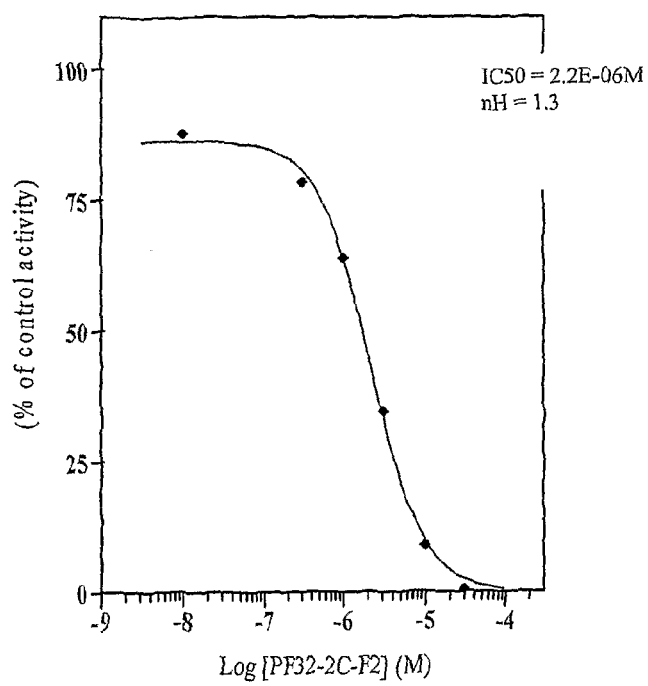
FIG. 11 shows the effects of compound ND0009 on the activity of human kinase Src.

FIGS. 1 to 10 show the curves of inhibition of kinase AbI activity for the compounds. FIG. 1 shows the effects of compound ND0006 on the activity of human kinase AbI. FIG. 2 shows the effects of compound ND0009 on the activity of human kinase AbI. FIG. 3 shows the effects of compound ND0019 on the activity of human kinase AbI. FIG. 4 shows the effects of compound ND0020 on the activity of human kinase AbI. FIG. 5 shows the effects of compound ND0021 on the activity of human kinase AbI. FIG. 6 shows the effects of compound ND0029 on the activity of human kinase AbI. FIG. 7 shows the effects of compound ND0031 on the activity of human kinase AbI. FIG. 8 shows the effects of compound ND0037 on the activity of human kinase AbI. FIG. 9 shows the effects of compound ND0038 on the activity of human kinase AbI. FIG. 10 shows the effects of compound ND0047 on the activity of human kinase AbI. FIG. 11 shows the effects of compound ND0009 on the activity of human kinase Src. The results are expressed as percentage of the specific activity of the control obtained in the presence of the tested compound. The $IC_{50}$ and Hill coefficient (nH) obtained are noted above each curve.

Figure 12:
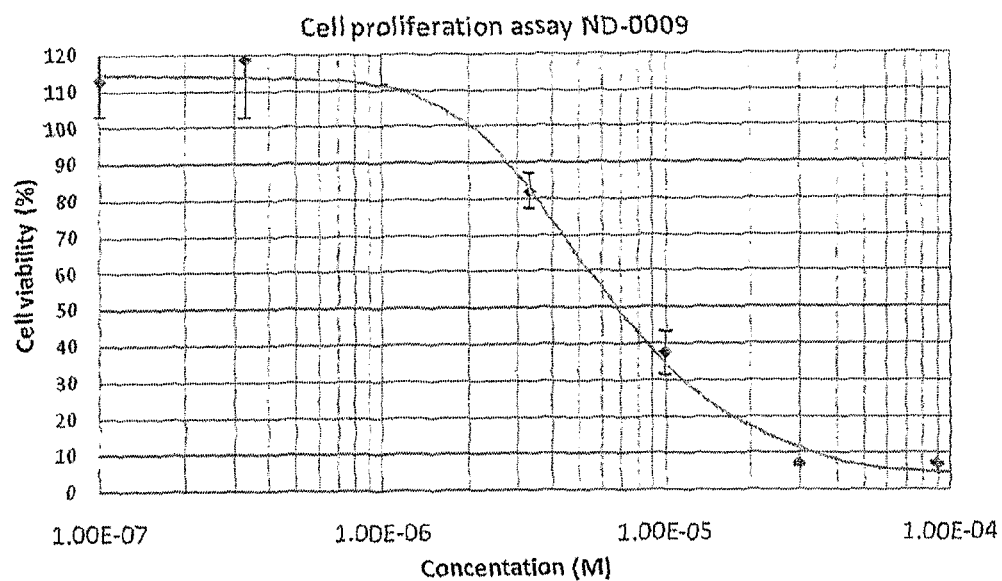
FIG. 12 shows the curve of inhibition of cellular proliferation on K562 cells expressing kinase Bcr-AbI.

FIG. 12 shows the curve of inhibition of cellular proliferation on K562 cells expressing kinase Bcr-AbI. The results are expressed as percentage of viable cells (MTT analysis) after 72 h of treatment with compound ND0009 at different concentrations expressed in mol/L.

The inhibitory activity of the compounds of the chemical series on different protein kinases was evaluated by Cerep (Cerep Kinase Profiling Service; www.cerep.com). The kinases used in the tests in vitro are human recombinant proteins expressed in human cells, insect cells or in bacteria. The references of the kinases tested are given in the following table.

| Test | Origin | Reference compound | Bibliography |
|---|---|---|---|
| AbI kinase (h) | Human recombinant (insect cells) | Staurosporin | 1 |
| AurA/Aur2 kinase (h) | Human recombinant (Sf21 cells) | Staurosporin | 2 |
| c-kit kinase (h) | Human recombinant (insect cells) | Staurosporin | 3 |
| PDGFRα kinase (h) | Human recombinant (insect cells) | Staurosporin | 4 |
| Src kinase (h) | Human recombinant (insect cells) | Staurosporin | 5 |

(1. Park, Y. W. et al., Homogeneous proximity tyrosine kinase assays: scintillation proximity assay versus homogeneous time-resolved fluorescence. Anal Biochem, 269, 94-104(1999),
2. Sun, C. et al., High-throughput screening assay for identification of small molecule inhibitors of Aurora2/STK15 kinase. J Biomol Screen 9, 391-7(2004),
3. Blume-Jensen, P. et al., Identification of the major phosphorylation sites for protein kinase C in kit/stem cell factor receptor in vitro and in intact cells. J Biol Chem 270, 14192-200 (1995);
4. Songyang, Z. et al., Catalytic specificity of protein-tyrosine kinases is critical for selective signalling. Nature 373, 536-9(1995);
5. Cheng, H. C. et al., A synthetic peptide derived from p34cdc2 is a specific and efficient substrate of src-family tyrosine kinases. J Biol Chem 267, 9248-56(1992)).

Each recombinant protein kinase was incubated with its appropriate biotinylated substrate in the presence of 0.05-20 μM of ATP (0.3 to 3 times the Km of the individual kinase) at 22° C. for 15 to 90 minutes depending on the kinase tested. The activity of the kinase was then detected by an HTRF assay.

The HTRF assay (CisBio International) is based on fluorescence transfer, using Europium (Eu3+) cryptate and XL665 respectively as donor and acceptor. When the biotinylated or tagged substrate is phosphorylated by the kinase, it reacts with a cryptate-labelled phosphospecific antibody. Addition of Streptavidin-XL665, SA-XL665, (or anti-tag antibody XL665) leads to juxtaposition of the cryptate and of the fluorophore XL665, which is reflected in fluorescence resonance energy transfer (FRET). The intensity of FRET depends on the quantity of cryptate-labelled antibody bound to the substrate, which is proportional to the quantity of phosphorylated substrate (Mathis, G. Probing molecular interactions with homogeneous techniques based on rare earth cryptates and fluorescence energy transfer. Clin Chem 41, 1391-7 (1995)).

To determine the inhibitory capacity of a compound on a kinase, the compound was incubated at a concentration of 10 μM with the kinase activity to be evaluated. The results obtained (Tables 6 and 7) therefore show the inhibitory power of a compound, at 10 μM on the kinase, expressed as percentage inhibition.

The evaluation of the activity of compounds ND0057, ND0058, ND0072, ND0073, ND0074, ND0075, ND0076, ND0077, ND0078, ND0079, ND0082, ND0085, ND0086, ND0087, ND0088, ND0089, ND0090, ND0091, ND0092, ND0093, ND0094, ND0095, ND0096, ND0098, ND0101, ND0102, ND0103, ND0104, ND0107, ND0108, ND0109, ND0117, ND0118, ND0119 at the concentration of 10 μM in kinase trial on AbI WT, AbI T315I or Src as well as the 1050 determination were carried out by the Reaction Biology Corp. (USA) society.

In Vitro Kinase Assays on Mutated AbI:

IC50 values (concentration of the compound inhibiting 50% of the kinase activity) of compound ND0006, ND0009, ND0010, ND0011, ND0019, ND0020, ND0021, ND0029, ND0031, ND0037, ND0038 et ND0047 were determined by Cerep incubating 5 increasing concentrations between $10^{-10}$ M and $10^{-4}$ M of the compound, The results are presented in Table 6 and in FIGS. 1 to 11.

IC50 values of compounds ND0057, ND0072, ND0074, ND0076, ND0077, ND0082, ND0085, ND0087, ND0088, ND0089, ND0090, ND0091, ND0093, ND0094, ND0096, ND0098, ND0117, ND0118 et ND0119 were determined by the company Reaction Biology Corp. (USA) on savage kinase AbI, mutants of kinase AbI (Q252H, Y253F and T315I) and/or Src kinase. Five increasing concentrations between $10^{-8}$ M and $10^{-4}$ M of each compound were incubated with one of the kinases in the presence of ATP at 10 µM according to the protocol of the company Reaction Biology Corp. The results are presented in Table 7.

In Vitro Assays of Inhibition of Cellular Proliferation

Cellular tests were carried out at the Montpellier Cancer Research Centre. The inhibition of proliferation by our compounds was analysed on 2 cell lines (U937 and K562) by calculating the IC50, testing 6 concentrations in triplicate for each of the compounds and for each line.

Imatinib, the known activity of which is described in the following table, was used as positive control in the tests.

| Cell line | Characteristics | Origin of the cells | Action of Imatinib |
|---|---|---|---|
| U937 | BCR-AbI⁻ | Myeloid precursors | No effect |
| K562 | BCR-AbI⁺ | Patient with CML | Sensitive |

The compounds (Imatinib and compound(s) of the present invention) were diluted at 10 mM in DMSO. Cells in exponential phase were seeded in 96-well plates at a concentration of $10^4$ cells/100 µL/well. The final concentrations of compound in the well in contact with the cells were 0.1; 0.3; 0.9; 3.3; 10; 30; 90 µM. The negative and positive controls were DMSO (whose final concentration must not exceed 5% of the final volume of the well) and Imatinib, respectively. The cells were treated with the compound for 72 h (the cells are treated 3 times, once every 24 h) before being washed and analysed using an MTT kit (3-[4,5-dimethylthiazol-2-yl]-2,5-diphenyl tetrazolium bromide) for determining cellular proliferation.

Biological Results

Percentage Inhibition of Kinase AbI by Different Compounds of the Chemical Class Invented The results, presented in Table 6, show the percentage inhibition of kinase AbI activity as a function of the compound incubated.

TABLE 6

Kinase tests in vitro. Each compound was incubated at 10 µM.
The percentage inhibition of kinase activity is stated.

| Designation of the compound | Percentage inhibition of kinase AbI |
|---|---|
| ND0004 | 31 |
| ND0005 | 10 |
| ND0006 | 33 |
| ND0009 | 100 |

TABLE 6-continued

Kinase tests in vitro. Each compound was incubated at 10 µM.
The percentage inhibition of kinase activity is stated.

| Designation of the compound | Percentage inhibition of kinase AbI |
|---|---|
| ND0010 | 1 |
| ND0011 | 6 |
| ND0012 | 8 |
| ND0019 | 82 |
| ND0020 | 85 |
| ND0021 | 94 |
| ND0022 | 5 |
| ND0023 | 36 |
| ND0024 | 18 |
| ND0025 | 39 |
| ND0026 | 8 |
| ND0027 | 29 |
| ND0028 | 14 |
| ND0029 | 77 |
| ND0030 | 26 |
| ND0031 | 86 |
| ND0032 | 27 |
| ND0033 | 53 |
| ND0034 | 17 |
| ND0035 | 16 |
| ND0036 | 47 |
| ND0037 | 97 |
| ND0038 | 94 |
| ND0040 | 21 |
| ND0041 | 14 |
| ND0044 | 6 |
| ND0045 | 58 |
| ND0046 | 49 |
| ND0047 | 94 |
| ND0050 | 27 |
| ND0051 | 20 |
| ND0053 | 33 |
| ND0054 | 15 |
| ND0059 | 5 |
| ND0060 | 16 |
| ND0061 | 46 |
| ND0062 | 6 |
| ND0063 | 8 |
| ND0064 | 12 |

The tests of kinase inhibition in vitro reveal several kinase-inhibiting molecular structures: 11 compounds inhibit kinase AbI activity at a level of at least 50%. It should be noted that 11 compounds also display inhibitory activity on kinase between 25 and 50% at a concentration of 10 µM.

The inhibition percentages of the kinase activity of savage AbI, mutated AbI T315I or Src kinase are classified in 3 categories according to table 7

TABLE 7

In-vitro kinase trial. Each compound was incubated at 10 μM.
The compound was divided in 3 categories according to the inhibition percentage of the kinase (inhibition of the kinase activity less than 10%, inhibition of the kinase activity between 10 and 50% and inhibition of the kinase activity greater than 50%)

| % inhibition < 10% | 10 ≤ % inhibition < 50% | % inhibition ≥ 50% |
|---|---|---|
| ND0010, ND0011, ND0012, ND0022, ND0026, ND0044, ND0059, ND0062, ND0063, ND0109 | ND0004, ND0005, ND0006, ND0023, ND0024, ND0025, ND0027, ND0028, ND0030, ND0032, ND0034, ND0035, ND0036, ND0040, ND0041, ND0046, ND0050, ND0051, ND0053, ND0054, ND0060, ND0061, ND0064, ND0058, ND0073, ND0074, ND0075, ND0078, ND0079, ND0086, ND0092, ND0095, ND0102, ND0103, ND0104, ND0107 ND0108 | ND0009, ND0019, ND0020, ND0021, ND0029, ND0031, ND0033, ND0037, ND0038, ND0045, ND0047, ND0057, ND0072, ND0074, ND0076, ND0077, ND0082, ND0085, ND0087, ND0088, ND0089, ND0090, ND0091, ND0093, ND0094, ND0096, ND0098, ND0101, ND0117, ND0118, ND0119 |
| ND0057, ND0058, ND0072, ND0073, ND0074, ND0076, ND0077, ND0078, ND0079, ND0082, ND0085, ND0086, ND0088, ND0089, ND0091, ND0092, ND0095, ND0098, ND0101, ND0103, ND0104, ND0107, ND0082, ND0086, ND0092, ND0104 | ND0075, ND0087, ND0090, ND0093, ND0094, ND0102, ND0108, ND0109, ND0117 | ND0118, ND0119, ND0096 |
| | ND0058, ND0073, ND0075, ND0078, ND0079, ND0085, ND0095, ND0101, ND0102, ND0103, ND0107, ND0108 ND0109 | ND009, ND0020, ND0021, ND0037, ND0038, ND0047, ND0057, ND0072, ND0074, ND0076, ND0077, ND0087, ND0088, ND0089, ND0090, ND0091, ND0093, ND0094, ND0096, ND0098, ND0117, ND0118, ND0119 |

The reference product for the treatment of CML, ALL and GISTs, imatininib, is capable of inhibiting, in addition to Bcr-AbI, the kinases c-kit and PDGFRα. The second and third generation compounds (Dasatinib, Nilotinib, Bosutinib) are, for their part, capable of inhibiting, in addition to Bcr-AbI, the kinases Aurora-A and/or c-Src. An analysis was performed for several of the compounds of the invention concerning their capacity for inhibiting one or more of these kinases. The results are presented in the following Table 8.

TABLE 8

Tests on kinases in vitro. Each compound was incubated at 10 μM.
The percentage inhibition of the kinase activity is indicated as a function of the kinase tested.

| | Percentage inhibition of kinase | | | | |
|---|---|---|---|---|---|
| | Abl | c-kit | c-Src | Aurora-A | PDGFR-α |
| ND0009 | 100 | 44 | 90 | 5 | 11 |
| ND0020 | 85 | 10 | 50 | 5 | 0 |
| ND0021 | 94 | ND | 59 | ND | ND |
| ND0037 | 97 | ND | 72 | ND | ND |
| ND0038 | 94 | ND | 71 | ND | ND |
| ND0047 | 94 | ND | 74 | ND | ND |

ND = Not determined.

These tests show a strong activity of some compounds towards the kinases AbI and c-Src.

Determination of the IC50 Values of the Compounds of Interest in Kinase Tests In Vitro Evaluation of IC50 was carried out for each compound having a molecular structure as well as an inhibitory activity of interest. The results obtained are presented in the form of tables (Tables 9 and 10) and of curves presented in FIGS. 1 to 11,

TABLE 9

IC50 values obtained in M (tests in vitro) on kinase Abl.

| IC50 in M | Abl | c-Src |
|---|---|---|
| ND-0006 | $>1 \cdot 10^{-4}$ | NT |
| ND-0009 | $3.9 \cdot 10^{-7}$ | $2.2 \cdot 10^{-6}$ |
| ND-0010 | $>1 \cdot 10^{-4}$ | NT |
| ND-0011 | $>1 \cdot 10^{-4}$ | NT |
| ND-0019 | $6.2 \cdot 10^{-6}$ | NT |
| ND-0020 | $4.6 \cdot 10^{-7}$ | NT |
| ND-0021 | $2.3 \cdot 10^{-6}$ | NT |
| ND-0029 | $1.1 \cdot 10^{-5}$ | NT |
| ND-0031 | $4 \cdot 10^{-6}$ | NT |
| ND-0037 | $1.4 \cdot 10^{-6}$ | NT |
| ND-0038 | $2.6 \cdot 10^{-6}$ | NT |
| ND-0047 | $4 \cdot 10^{-7}$ | NT |

(NT = not tested).

TABLE 10

IC50 obtained on kinases Abl WT, T315I and Src. The compound are classified in 4 categories of IC50: IC50 less than $1 \cdot 10^{-9}$ M; IC50 comprised between 1 and 100 nM; IC50 comprised between 100 nM and 10 μcromolaires and IC50 greater than 10 μM.

| IC50 < $1 \cdot 10^{-9}$ M | $1 \cdot 10^{-9}$ M ≤ IC50 < $1 \cdot 10^{-7}$ M | $1 \cdot 10^{-7}$ M ≤ IC50 < $1 \cdot 10^{-5}$ M | IC50 > $1 \cdot 10^{-5}$ M |
|---|---|---|---|
| ND0117, ND0118, ND0119 | ND0072, ND0074, ND0077, ND0087, ND0089, ND0090, ND0096 | ND0009, ND0019, ND0020, ND0021, ND0031, ND0037, ND0038, ND0047, ND0057, ND0076, ND0082, ND0085, ND0088, ND0091, ND0093, ND0094, ND0098, ND0096, ND0118, ND0119 | ND0006, ND0010, ND0011, ND0029 |
| ND0118 | ND0072, ND0074, ND0077, ND0087, ND0089, ND0090, ND0117, ND0119 | ND0009, ND0057, ND0077, ND0088, ND0091, ND0093, ND0094, ND0096, ND0098 | |

These results confirm the results previously obtained and reveal the inhibitory potential of several compounds of this chemical class.

Kinase Tests In Vitro on Mutated Abl 4 compounds were tested for their capacity to inhibit various mutated kinases Abl (American company, Reaction Biology Corp.).

TABLE 11

IC50 values obtained in nM (tests in vitro) on wild-type (WT) or mutated kinase Abl (Q252H, Y253F and T315I).

| IC50 in nM | Abl WT | Abl Q252H | Abl Y253F | Abl T315I |
|---|---|---|---|---|
| ND-0009 | 709.2 | 21.81 | 28.01 | >100 000 |
| ND-0020 | 44.56 | <10 | <10 | >100 000 |
| ND-0037 | 654.5 | 68.13 | 84.96 | 63330 |
| ND-0047 | 381.7 | 18.28 | 18.43 | >100 000 |

Determination of the IC50 Values of the Compounds of Interest in Tests of Cellular Proliferation The capacity of compound ND0009 for inhibiting the proliferation of malignant cells expressing kinase Bcr-Abl (K562), or not (U937), was analysed by determining the IC50 corresponding to the concentration of compound inhibiting cell growth at a level of 50%.

The results obtained are presented in Table 12 below and in FIG. 12.

TABLE 12

IC50 values obtained in μM (cell tests) on the cell lines K562 and U937.

| | IC50 (μM) | |
|---|---|---|
| | K562 | U937 |
| ND0009 | 6 | >100 |
| Imatinib | 0.1 | 9 |

Compound ND0009 is active on the Bcr-Abl+ cells (K562) and not on the Bcr-Abl− cells (U937), and it displays cellular specificity similar to that of Imatinib.

Another trial was carried out: increasing concentrations of compound ND0009, ND0072, ND0074, ND0076, ND0087, ND0089, ND0090, ND0096, ND0117, ND0118, ND0119 were incubated for 24 h and/or 72 h on K562 and on U937 cells in order to determine their IC50. Imatinib was tested as a positive control. (table 13)

TABLE 13

IC50 obtained on K562 and U937 cell lines

| | IC50 < $1 \cdot 10^{-8}$ M | $1 \cdot 10^{-8}$ ≤ IC50 < $1 \cdot 10^{-6}$ M | $1 \cdot 10^{-6}$ M ≤ IC50 < $1 \cdot 10^{-5}$ M | IC50 ≥ $1 \cdot 10^{-5}$ M |
|---|---|---|---|---|
| IC50 at 24 h on K562 | | ND0117, ND0119 | ND0020, ND0076, ND0087, ND0090, ND0096, ND0118 | Imatinib, ND0072, ND0074, ND0089 |
| IC50 at 72 h on K562 | ND0117, ND0118, ND0119 | Imatinib, ND0076, ND0087, ND0090, ND0096, ND0072, ND0074, ND0089 | ND0020 | ND0009 |
| IC50 at 72 h on U937 | | | Imatinib | ND0009 |

Most of the compounds tested are more active than the reference product (Imatinib).

The invention claimed is:
1. Compounds of general formula I:

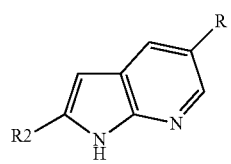

Formula I in which R represents:
a group NHCOR¹, or
a group NR³R⁴
where
R¹ represents:
a phenyl group optionally mono- or polysubstituted with:

a halogen atom,
a nitro group,
a cyano group,
a methylthiazyl group,
an alkoxy group,
a trifluoroalkoxy group,
an aryloxy group,
a trifluoroalkylgroup,
a substituted or unsubstituted sulphonamide group,
a heteroaryl group optionally mono- or poly-substituted with a halogen atom,
a linear or branched $C_1$-$C_6$ alkyl group,
or a group selected from the groups A, B, C, D or E as defined below:

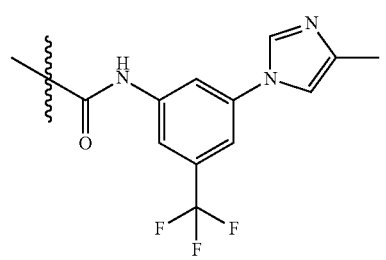

A

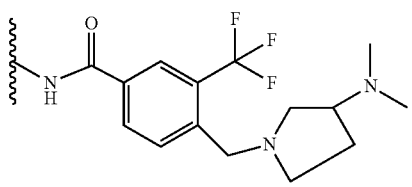

B

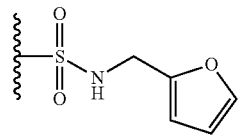

C

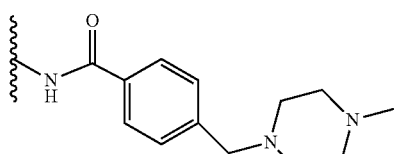

D

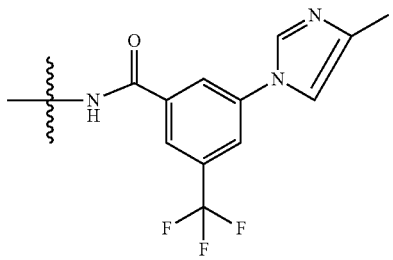

E a pyridyl group optionally mono- or poly-substituted with a propylsulphanyl group,
a thiophenyl group,
a thiazyl group,
an imidazyl group,
a pyrazyl group optionally mono- or polysubstituted with a C1-C6 alkyl group,
a quinoxaline group,
a dihydrobenzofuranyl group,
an indyl group,
a cyclopropyl group,
a linear or branched $C_1$-$C_6$ alkyl group, or
a $C_1$-$C_6$ phenylalkyl group, optionally mono- or poly-substituted with an alkoxy group, and/or a halogen atom, $R^2$ represents:
an ester group $COOR^{14}$,
an alkyl group $CH_2R^9$, $CH_2OCOR^{10}$, $CH_2NR^{11}R^{12}$,
an amide group $CONR^7R^8$, or
a group $COR^{13}$, $R^7$ and $R^8$, which may be identical or different, represent:
a hydrogen atom,
N,N-dimethylaminopropyl, or
N-morpholinoethyl, $R^9$ represents:
an imidazyl or pyrryl group,
a N-morpholinyl or tetrahydrofuranyl group, $R^{10}$ represents:
a quinoxaline group, $R^{11}$ and $R^{12}$, which may be identical or different, represent:
a hydrogen atom,
a linear or branched $C_1$-$C_6$ alkyl group,
a phenylalky group,
a $C_1$-$C_6$ alkoxyalkyl group,
a cyclohexyl, optionally mono- or polysubstituted with a $C_1$-$C_6$ alkyl group,
a phenyl group, optionally mono- or polysubstituted with:
    a halogen atom,
    a cyano group,
    a sulphonamide group,
    a nitro group,
    a $C_1$-$C_6$ alkyl group,
    an alkoxy group, or
    a hydroxyl group,
or a pyridyl ring, $R^{13}$ represents an N-morpholyl group, $R^{14}$ represents:
a linear or branched $C_1$-$C_6$ alkyl group, or
a phenyl group, optionally substituted with an alkoxy group, $R^3$, $R^4$, which may be identical or different, represent:
a hydrogen atom,
a group $CH_2R^{15}$,
a pyridyl, indyl, benzimidazyl, or pyrazyl, optionally substituted with a $C_1$-$C_6$ alkyl group, or
a phenyl group optionally mono- or polysubstituted with:
    an alkoxy group,
    a trifluoroalkoxy group,
    a halogen atom,
    a trifluoroalkyl group,
    a CONHalkyl group,
    an NHCOalkyl group,
    a sulphonamide group,
    a linear or branched $C_1$-$C_6$ alkyl group, or
    a methanesulphonamide group, $R^{15}$ represents:
a phenyl group optionally mono- or poly-substituted with:
    a halogen atom,
    an alkoxy group, a trifluoroalkoxy group, a linear or branched $C_1$-$C_6$ alkyl group, a $C_1$-$C_6$ trifluoroalkyl group, a pyridazinyl group, optionally mono- or poly-substituted with a halogen atom, a sulphonamide group, a methanesulphonamide group, or a group selected from the group consisting of groups A, B, C, D and E as defined above, a thiophenyl group, a thiazyl group, optionally mono- or polysubstituted with a group selected from the groups A, B, C, D or E as defined above, an imidazyl group, an indyl group, optionally mono- or polysubstituted with a linear or branched C1-C6 alkyl group, a pyrazyl group, optionally mono- or polysubstituted with a linear or branched C1-C6 alkyl group, or with a group selected from A, B, C, D or E groups as defined above, a pyridyl group optionally mono- or polysubstituted with an alkoxy, group, or a group selected from the groups A, B, C, D or E as defined above, a group selected from the groups A, B, C, D or E as defined above, a pyrimidinyl group optionally mono- or polysubstituted with a group selected from the groups A, B, C, D or E as defined above, a benzimidazyl group, optionally mono- or polysubstituted with a linear or branched C1-C6 alkyl group, or a 1-H pyrrolo[2,3-b]pyridyl group.

2. Compound according to claim 1 of general formula II

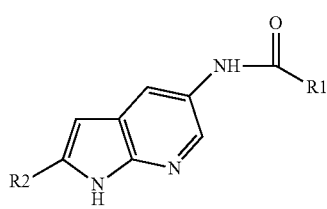

Formula II

R1 and R2 as previously defined.

3. Compound according to claim 1 of general formula III

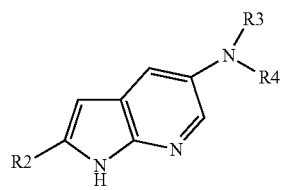

Formula III

R2, R3 and R4 as previously defined.

4. Compound according to claim 1 of general formula XIV

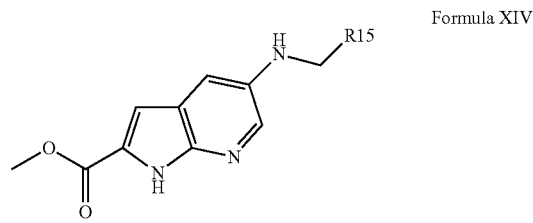

Formula XIV in which R15 represents:
  a phenyl group, optionally mono- or polysubstituted, with:
    a halogen atom,
    an alkoxyl group,
    a linear or branched alkyl group,
    a C1-C6 trifluoroalkyl group,
    a trifluoroalkoxy group,
    a sulphonamide group,
    a methylsulphonamide group,
    a group selected from the group consisting of groups A, B, C, D and E,
  a thiazyl group, substituted or not by a group selected from the group consisting of groups A, B, C, D and E
  a thiophenyl group,
  an imidazyl group,
  an indyl group, optionally mono- or polysubstituted, with a linear or branched C1-C6 alkyl group,
  a pyrazyl group, optionally mono- or polysubstituted, with a group selected from the group consisting of groups A, B, C, D and E, or by a linear or branched C1-C6 alkyl,
  a benzimidazyl group, optionally mono- or polysubstituted with a C1-C6 alkyl group,
  a pyridyl group, optionally mono- or polysubstituted, with a group selected from the group consisting of groups A, B, C, D and E, or
  a pyrimidinyl group, optionally mono- or polysubstituted, with a group selected from the group consisting of groups A, B, C, D and E,
  a 1-H pyrrolo[2,3-b]pyridyl group.

5. Compound according to claim 1 of general formula XV

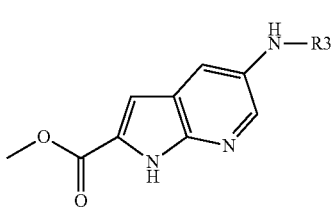

Formula XV in which R3 represents:
  a pyridyl group,
  a phenyl group, optionally mono- or polysubstituted, with
    an alkoxyl group,
    a halogen atom,
    a —CONH alkyl group, or
    a C1-C6 alkyl group.

6. Compound of general formula XVI

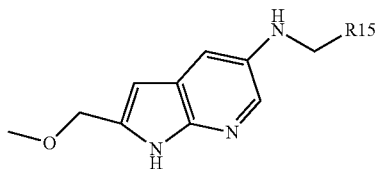

Formula XVI in which R15 represents:
  a phenyl group, optionally mono- or poly substituted, with:
    B—a linear or branched C1-C6 alkyl group, or
  a group selected from the group consisting of groups A, B, C, D and E as defined below:

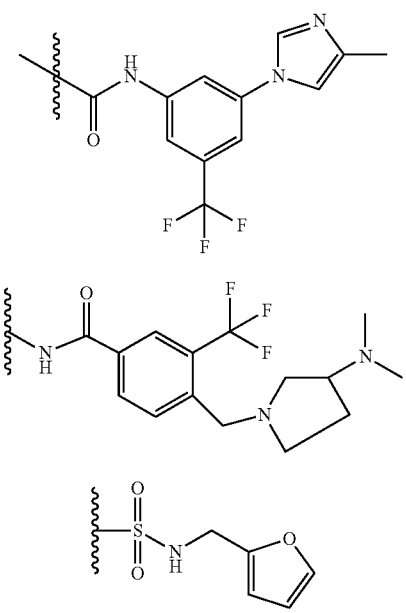

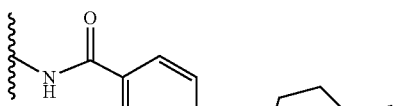

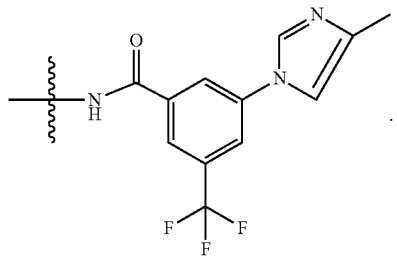

7. Method for inhibiting the AbI and Src protein kinases comprising administering a compound according to claim 1.

8. Compound according to claim 1, wherein the compound is selected from the group consisting of methyl 5-(2-bromobenzamido)-1H-pyrrolo[2,3-b]pyridine-2-carboxylate, methyl 5-(2-fluoro-6-methoxybenzamido)-1H-pyrrolo[2,3-b]pyridine-2-carboxylate, N-(2-((4-hydroxyphenylamino)methyl)-1H-pyrrolo[2,3-b]pyridin-5-yl)-2-bromobenzamide, N-(2-((1H-pyrrol-2-yl)methyl)-1H-pyrrolo[2,3-b]pyridin-5-yl)-2-bromobenzamide, 2-bromo-N-(2-(methoxymethyl)-1H-pyrrolo[2,3-b]pyridin-5-yl) benzamide, and 5-(2-bromobenzamido)-N-(3-(dimethylamino) propyl)-1H-pyrrolo[2,3-b]pyridine-2-carboxamide.

9. Pharmaceutical composition comprising, as active principal, a compound according to claim 1 and a pharmaceutically acceptable excipient.

10. Method for inhibiting the AbI and Src protein kinases comprising administering a compound according to claim 6.

\* \* \* \* \*